US011854682B2

(12) United States Patent
Lin et al.

(10) Patent No.: US 11,854,682 B2
(45) Date of Patent: Dec. 26, 2023

(54) SYSTEM AND METHOD FOR IMPLEMENTING PHYSICAL STIMULATION SERVICE

(71) Applicant: Chuan Chung Wang, Sacramento, CA (US)

(72) Inventors: Shaw Yueh Lin, San Diego, CA (US); Wei-Cheng Wang, Taipei (TW)

(73) Assignee: Chuan Chung Wang, Sacramento, CA (US)

( * ) Notice: Subject to any disclaimer, the term of this patent is extended or adjusted under 35 U.S.C. 154(b) by 703 days.

(21) Appl. No.: 16/497,932

(22) PCT Filed: Mar. 27, 2018

(86) PCT No.: PCT/CN2018/080640
§ 371 (c)(1),
(2) Date: Sep. 26, 2019

(87) PCT Pub. No.: WO2018/177280
PCT Pub. Date: Oct. 4, 2018

(65) Prior Publication Data
US 2021/0104310 A1    Apr. 8, 2021

Related U.S. Application Data

(60) Provisional application No. 62/476,869, filed on Mar. 27, 2017.

(51) Int. Cl.
*G16H 20/30* (2018.01)
*G16H 40/67* (2018.01)
(Continued)

(52) U.S. Cl.
CPC .......... *G16H 20/30* (2018.01); *A61H 39/002* (2013.01); *A61H 39/02* (2013.01); *A61H 39/08* (2013.01);
(Continued)

(58) Field of Classification Search
CPC .......... G16H 20/30; G16H 40/67; A61H 39/02
(Continued)

(56) References Cited

U.S. PATENT DOCUMENTS 6,520,903 B1 *   2/2003   Yamashiro .............. A61N 2/002
                                                                600/9
8,170,656 B2    5/2012   Tan et al.
(Continued)

FOREIGN PATENT DOCUMENTS

| CN | 102349037 A | 2/2012 |
| CN | 104225784 A | 12/2014 |
| CN | 105854184 A | 8/2016 |

*Primary Examiner* — Christopher A Flory

(57) ABSTRACT

The present system combines, on a host server, clinician software for accessing a case history database of past results/feedback from users seeking stimulation therapy, other users within a member network and other users outside the member network and pharmacy software for generating, in the form of a database, an expert system/artificial intelligence program and signal processing software, stimulation waveforms required by the users according to prescriptions from clinicians (completed by clinical experts/server knowledge software) and/or pain points indicated by the users, wherein an innovative open terminal data format and file format and an innovative high-efficiency frequency band waveform compression technique are used. The present method and system embed innovative software tools into an innovative stimulation controller in a wired or wireless connection and a client device of an innovative skin carrier set related thereto so as to assist users in using imaging, sensing, augmented reality and software technology to identify stimulation points, and measure skin impedance, and provide other innovative tool solutions.

11 Claims, 25 Drawing Sheets

(51) Int. Cl.
  *G16H 10/60* (2018.01)
  *G16H 50/30* (2018.01)
  *G16H 20/10* (2018.01)
  *G16H 80/00* (2018.01)
  *A61H 39/00* (2006.01)
  *A61H 39/08* (2006.01)
  *G06F 3/01* (2006.01)
  *G06F 3/16* (2006.01)
  *A61H 39/02* (2006.01)

(52) U.S. Cl.
  CPC .............. *G06F 3/011* (2013.01); *G06F 3/167* (2013.01); *G16H 10/60* (2018.01); *G16H 20/10* (2018.01); *G16H 40/67* (2018.01); *G16H 50/30* (2018.01); *G16H 80/00* (2018.01)

(58) Field of Classification Search
  USPC ........................................................ 600/548
  See application file for complete search history.

(56) References Cited

U.S. PATENT DOCUMENTS

| | | | |
|---|---|---|---|
| 2009/0326406 A1 | 12/2009 | Tan et al. | |
| 2012/0245409 A1* | 9/2012 | Liang | A61M 21/02 600/27 |
| 2013/0253613 A1 | 9/2013 | Salahovic et al. | |
| 2015/0012060 A1* | 1/2015 | Liu | G16H 40/67 607/59 |
| 2017/0156662 A1* | 6/2017 | Goodall | A61N 2/002 |
| 2017/0164876 A1* | 6/2017 | Hyde | A61B 5/1118 |

* cited by examiner clinical trial waveform
$V_b = 0.35 V_p$    $T_1 / (T_1+T_2) = 33\%$

SYSTEM AND METHOD FOR IMPLEMENTING PHYSICAL STIMULATION SERVICE

BACKGROUND OF THE INVENTION

1. Field of the Invention

The present invention relates to a system and method for physical stimulation services, and more particularly to a system and method for improving the effectiveness and personalization of physical stimulation treatment.

2. Description of the Prior Arts

When someone is not feeling well, a physician, dentist, chiropractor, physical therapist or trainer, sports medicine specialists, acupuncturist or doctors in the Traditional Chinese Medicine (TCM), together called clinicians herein, usually shall examine the patient, use needed lab or physical tests and clinical diagnostic tools to help decide the cause or source of ailments, and then proceed to prescribe a combination of drug, physical, surgical and psychological treatment modalities to try to help cure the ailments for the patient.

Individuals nowadays also seek to maintain health and wellness and prevent diseases from happening by exercising, nutrition management, taking vitamins and herbal supplements, and using spas or yoga classes to reduce physical and psychological stress.

Yet there are also increasing amount of people nowadays, probably due to the prolonged life span and/or increased or lack of physical activities in one's daily life, who have to deal with chronic or long term ailments such as sleep disorder, arthritis, migraines, hypertension, diabetes, various muscle and nerve pain such as back pain, tennis elbow, carpal tunnel syndromes, etc, with drugs taken over a very long period of time.

We believe that knowledge and experiences in physical stimulation modalities, both non invasively or invasively, from electrical, magnetic, sound, laser, heat to pressure, have advanced so much in the past 70 years that, aided by transformational connectivity and technological breakthroughs, we can now offer personalized, cost effective, 24-7 physical stimulation treatment modalities that may, on its own or in combination with drugs and other physical or psychological therapies, help to bring better results of disease prevention and treatment, and to bring better quality of life through wellness regiments.

Physical non drug stimulation such as electrical, magnetic, ultrasound, laser, heat and others to treat acute and chronic diseases and to help train and treat muscle activities is an industry of over US$5B globally, with over $4B in invasive stimulation modalities and about $1B in non invasive external physical stimulation treatments. Both markets are expected to continue to grow.

Physical stimulation routines such as reflexology, foot and body massage, magnetic therapies, acupuncture, acupressure and others for both wellness and chronic pain and disease management, is an even bigger industry from a wide selection of consumer and professional products to services such as the fast growing service providers for foot and whole body massage in places like spas and retail service stores, is probably another big market.

Invasive implanted physical stimulation treatments usually require minor surgeries for implants but one s done more surgeries, though less involved than those needs in the original implant, are needed only to replace either the controller or battery. Since these implants are treatment specific, such as implanted electro-stimulation of Vagus nerve to treat depression, the stimulation signals of all current treatment modalities are fixed, just like prescribed drugs for disease treatments, and may be adjusted only at the care of a physician, requiring thus an office visit. While the challenge to personalize the stimulation treatment with invasively implanted physical stimulation treatment modality remains very high due to the many constraints of implanted controller devices and due to the critical safety and liability considerations, the need for inventive ways to bring personalized or customized physical stimulation treatment modality to this way of physical stimulation treatments remains.

Non invasive physical stimulation is intended for disease treatment, disease prevention and wellness purposes. The controller is not implanted inside the body and therefore, it may be programmed with greater ease for personalized or customized treatments. However, controllers of all current physical stimulation devices include fixed choices of the stimulation waveform and usually what may be adjusted by the user/patient are the intensity and duration of each stimulation waveform.

As needs and conditions of a user change, and when and where visiting the doctor's office or even calling the doctor is not possible, there is still a need for the user, for example, to be able to reprogram the device and/or to stimulate different parts of the body, and/or use a different type of carrier on the body, etc, to better treat the condition.

Treatment efficacy is also a challenge facing physical stimulation device manufacturers, as different types of waveform other than those built into each device may be used to treat conditions with better results, depending on where the stimulation is applied on the body and depending on the particular conditions of each patient/user. But usually these waveform are created electronically by a microprocessor or a digital signal processor in each controller and therefore are fixed. Sophisticated professional devices for clinicians or clinical uses may offer a broader selections of waveform and allow clinicians to adjust parameters such as frequency of the pulse train, pulse width of each pulse, etc. But these devices are usually expensive. Adding any waveform on demand outside of the library of basic waveform stored in a device is usually not allowed in current physical stimulation devices.

Adaptation of our nerve and muscle systems to the same physical stimulation waveform, just like adaptation of our body organs to the same drug taken repetitively for a long time, is also a challenge for physical stimulation treatment modalities. A cost effective digital solution is needed to arrange the stimulation waveform, just like change of drugs for a patient over the long course of treatment, in such a way that adaptation may be reduced or eliminated without a very complicated controller design or without the very expensive human interventions.

With the smart phones and high speed connectivity to the Internet fast becoming ubiquitous in recent years, many new devices for health and wellness purposes that interact with an App in a companion smartphone for connections to an Internet based cloud server for data storage and analysis have been brought to the market. Almost all of these so far are for vital sign measurement and tracking purposes—blood pressure, blood glucose, heart rate, pulse oximeter, body tempera. Only one recent device, called iTENS, is an App based transcutaneous electrical nerve stimulation device (TENS). One may use the App in one's smart phone to remotely control the controller that sits on top of the pair of electro-pads. The main purpose of this App is so that a user may place the controller/pad combo on, for example, his or her lower back and can control the stimulation with fiddling blindly the control knobs on the controller to adjust the intensity and to select the stimulation programs built into the controller. The App may send certain data related to the date and time of the treatment etc to the cloud server for future references. Unlike vital signs the storage and long term tracking of which are meaningful, electrical stimulation, in the current way it is used, does not have any meaningful data for storage and long term tracking.

SUMMARY OF THE INVENTION

In order to solve the deficiencies summarized in the background of invention section, the present invention provides a system and method for improving the effectiveness and personalization of physical stimulation treatment by setting a server side service subsystem, a client service subsystem, a stimulation controller, and a skin carrier, etc., to achieve the purpose of improving the effectiveness and personalization of physical stimulation treatment.

In order to achieve the above-mentioned objectives, a method and a system for effecting physical stimulation as a Service are provided.

The system includes:
a server side service subsystem,
a client service subsystem,
at least one stimulation controller, and,
at least one skin carrier; wherein the client service subsystem requests the server side service subsystem in response to a request, the server side service subsystem responds to the request of the client service subsystem to provide a prescription packet and/or waveform dose for physical stimulation to the client service subsystem, and after the waveform dose is prepared, the client service subsystem provides the waveform dose to the stimulation controller, and the stimulation controller controls the skin carrier to apply physical stimulation corresponding to the waveform dose to skin.

The method includes:
providing a client service subsystem, at least one stimulation controller, and at least one skin carrier;
preparing a waveform dose for physical stimulation by the client service subsystem;
transmitting the waveform dose for physical stimulation to the stimulation controller;
controlling the skin carrier applied to the skin by the stimulation controller and applying physical stimulation corresponding to the waveform dose to the skin;
wherein the physical stimulation corresponding to the waveform dose has a composite stimulation waveform with medium carrier frequency that goes deeper than epidermal layer and further into the dermal area and creates the same effect as a deep massage type pressure on reflex zones and vital points used by acupressure.

According to the above system and method, the present invention, by setting a server side service subsystem, a client service subsystem, a stimulation controller, and a skin carrier, etc., can achieve the purpose of improving the effectiveness and personalization of physical stimulation treatment.

DETAILED DESCRIPTION OF THE PREFERRED EMBODIMENTS

Figure 1:
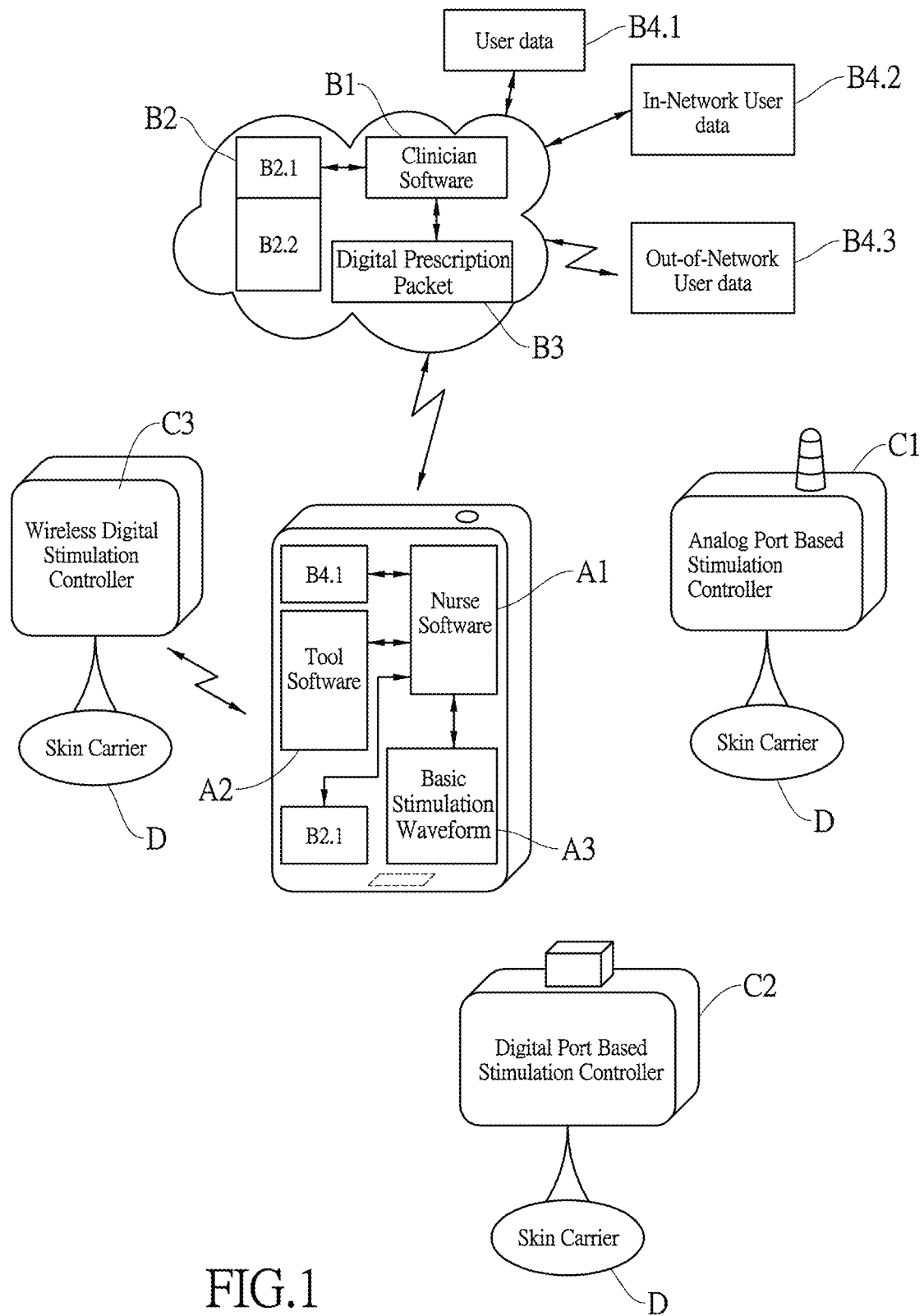
FIG. 1 shows an overall system of our inventive system of Physical Stimulation as a Service (PSaaS)

FIG. 1 shows our overall system to effect physical stimulation as a service (PSaaS).

A is our proposed client side service subsystem, which we will call it "Client" throughout our this patent application.

B is our proposed server side service subsystem, which we will call it "Host" throughout our this patent application.

C is our proposed hardware stimulation controller that is connected to a Client, which we will call it "Stimulation Controller" throughout this patent application.

D is our proposed hardware skin carrier that is connected to the Stimulation Controller to deliver stimulation to selected parts of a user's body and to transmit back to the Stimulation Controller any information collected from an active skin carrier. We will call it "Carrier" throughout our article.

Additionally, throughout this patent application, we use "User" for the person receiving prescribed physical stimulation. User is selected instead of "patient" to emphasize our inventive system is intended for both wellness as well as health related disease prevention or treatments.

We use "Clinician(s)" for the professional(s) including doctor(s), chiropractor(s), physical therapist(s), physical trainers( ), sports medicine therapist(s), Traditional Chinese Medicine(TCM) doctor(s), acupuncturist(s), reflexologist (s), massage professional(s) and other professional(s) who prescribe physical stimulation to Users.

We use "impedance" which includes resistance.

We use "transcutaneous" which includes "transcranial"

When a User is seeking a physical stimulation treatment from a Clinician, the first step is to check in with a nurse or a trained clinical office assistant, together called "Nurse" throughout our article.

In our system, that is A1—Nurse Software.

Before the office visit for physical treatments, Nurse Software will do just what a nurse may do—check in the User, take vital signs, ask the User reason of the visit and any symptoms and then provide these information to the Clinician.

Once the Clinician examines the User and determine the stimulation modalities for the User, Nurse Software, once it receives the "stimulation prescription packet" from the "pharmacy software" (please see explanations later in this section), Nurse Software shall be responsible to guide the User to administer the stimulation modalities with selected Controller(s) and Carrier(s). Nurse Software is also responsible for monitoring the stimulation status during the course of the stimulation treatment to handle any emergency conditions. After the stimulation treatment, the Nurse Software shall assist User to make post treatment reports, provide treatment feedback for future references and to schedule if needed the next appointment. These steps shall be implemented software wise. See FIG. 5 for a description of an embodiment of A1.

A2 is Tool Software which Nurse Software will work with to fulfill its responsibilities in the three stages of pre-treatment, during-treatment and post-treatment processes. Software Tool includes, but not limited to, the following:

Pre-Treatment Tool Software:
  A2-1 imaging and/or sensing software to verify Controller and Carrier type to be used in the physical stimulation treatment.
  A2-2 imaging and sensing software to verify the identification of a User, as multiple Users may use the same Client device and Software for physical stimulation treatments.
  A2-2 imaging and sensing software to assist the correct placement of Carrier(s) on User's body based on the prescribed treatment modality by the Clinician Software. (See FIGS. 6A and 6B and 6C)
  A2-3 skin impedance/resistance measurement tool in order to aid, for example, step A2-2. See FIG. 15 A-15D.

During-Treatment Tool Software
  monitoring the status of the stimulation from sensors built into the Carrier(s) used for the stimulation, such as current level of an electrical stimulation (see FIG. 15 for an embodiment), pressure level of the rubber bladder used for applying compression and/or pressure of a pressure stimulation, temperature level of a heat stimulation, etc.
  responding to User intervention such as stopping a stimulation session requirement, etc.
  responding to other tasks such as an incoming phone call wherein the Nurse Software has to react based on the pre-programmed protocols of task handling. For example, Nurse Software may suspend the stimulation treatment when the User decides to take the call, may suspend the stimulation using real time streamed waveform but continue the stimulation with a waveform pre-stored in the Controller, in order for the User to take the call, or may direct the call to voice mail if the stimulation may not be disrupted in the middle of the treatment which is agreed to by the User, or the User chooses not to answer calls during the course of the stimulation treatment.

Post-Treatment Tool Software
Post treatment report generation
Post treatment feedback collection and forwarding to Clinician Software for immediate attention, followups and storage as part of the User record and part of the overall big data database.
Post treatment future appointment scheduling A3 is a library of basic stimulation waveform dosage digital files so that, in the event Host server B is not accessible, a standard stimulation treatment may still be performed by the Nurse Software for the User.

The library may contain both standard stimulation waveform, such as, using TENS as an example, fixed set of waveform available in a typical consumer TENS treatment device, and digital stimulation waveform file the User used in the past treatment. The content of A3 is connected to the Host server software in two ways:
  parameters describing each stimulation waveform, such as category (electrical, magnetic, infrared heat, ultrasound, pulsed pressure, etc.), type (periodic, rhythm, random, etc), parameters (frequency, pulse width, duty cycle, rhythm type, etc ay be stored on the Host Server software, which may be used by the Clinician Software B1 on the Host server to decide where the stimulation waveform dosage may come from this library A3 of the stimulation waveform in the Client Software or from the centralized Pharmacy Software B2. This allows more efficient use of data bandwidth between Host software A and Client software B. This becomes important when a large amount of stimulation treatments may happen at the same time.

No information of the content of A3 is saved in the Host server and the Clinician Software shall access A3 saved on the Client Software A at the time the Clinician Software is finalizing the prescription for the stimulation treatment.

Another software function in the Client Software A is User information, history and post treatment feedback, together called B4.1, as it is also replicated on the Host Software B.

Depending on the processing power of the Client device, the stimulation waveform synthesizer B2, or a portion of it, may also reside in the Client Software A. Apps for simple tone frequency generation are already available even for smart phones and tablets, which may have less processing power and storage than a conventional desktop or laptop PC has. Therefore, at least portion of our full stimulation waveform synthesizer B2 may be replicated on Client software A. The advantage to have all or part of B2 on Client Software A is that, workload of B2 may be better distributed among the Host server and Client devices, especially when there is a large number of concurrent stimulation treatments.

Host Software B is composed of the followings:

B1: Clinician Software

Clinician Software includes an expert prescription system that uses software algorithms, or a collaborative communication platform where a clinician or a group of clinicians from multiple disciplines, may interact with one other and/or with the User, to determine the full prescription for the stimulation treatment (see FIG. 4 for more explanations) based on symptoms and user related information Nurse Software A1 collected when the User checks in, plus history and feedback of the patient (B4.1), and accessible history, feedback and relevant statistics of other Users within this network or membership group (B4.2), and accessible history, feedback and relevant statistics of other third party Users outside of the network and membership group (B4.3)

B4.1 and B4.2 may reside inside the cloud Host server B and B4.3 usually reside remotely inside other servers.

B2: Pharmacy Software

For physical stimulation treatments, stimulation waveform is just like the pharmaceutical dosage in a drug centric treatment. For example, a pulse train waveform of a pre selected frequency may apply to a target body part a therapeutically effective pulsating local pressure through an inflated bladder cuff. Another common example is a well tuned pulse train waveform for microcurrent Electro-Neuro Stimulation (MENS) stimulation that may be particularly useful for the User.

B2 is further composed of B2-1, a real time digital signal processor (DSP) based stimulation waveform synthesizer and B2-2, a stimulation waveform library created off line and stored for immediate uses. All stimulation waveform dosages will be digital and saved or streamed in either standard file formats such as .mp3, .wav, .midi, .jpg, .mov etc or in proprietary data file formats.

Please see FIGS. 3A-3H for more detailed explanations wherein many inventive methods, subsystems and processes we put together in order to efficiently and cost effectively provide a personalized or customized PsaaS will be made clear.

B3: Digital Prescription Packet

Each digital prescription packet contains the prescription data packet and stimulation waveform dosage data file that the Nurse software in the Client device will be able to use to prepare the User and administer the stimulation treatment. Please see FIGS. 3A-3H for detailed information on stimulation waveform dosage and its file formats. Please see FIG. 4 for a more in depth explanation of an embodiment of a prescription data packet.

C: Stimulation Controllers

Shown in FIG. 1 are three examples of stimulation controller embodiment:

C1 is a stimulation controller that is connected to and interact with the Client device and software in an analog way. Please see FIG. 7 for a detailed explanation of its many inventive features, methods and system implementations.

C2 is a stimulation controller that is connected to and interact with the Client device and software in a digital way. Please see FIG. 8 for a detailed explanation of its many inventive features, methods and system implementations.

C3 is a stimulation controller that is connected to and interact with the Client device and software digitally in a wireless way. Please see FIG. 9 for a detailed explanation of its many inventive features, methods and system implementations D: Skin Carriers Skin carriers are connected to its associated stimulation controller, applied and attached to the body of the User, and deliver the planned physical stimulation treatment to the User. Please see FIGS. 10A to 15D for several different inventive carrier designs that work effectively without inventive stimulation controllers to make possible inventive physical stimulation modalities several of which will be described in FIGS. 16A-16B and in later sections.

Note that, other than B4.3, Host software B and Client software A may co-locate on a powerful and networked computer to effect all functions, services and stimulation treatments for multiple Users in a hospital, rehab center, spa or even in a large massage retail service outlet.

Figure 2:
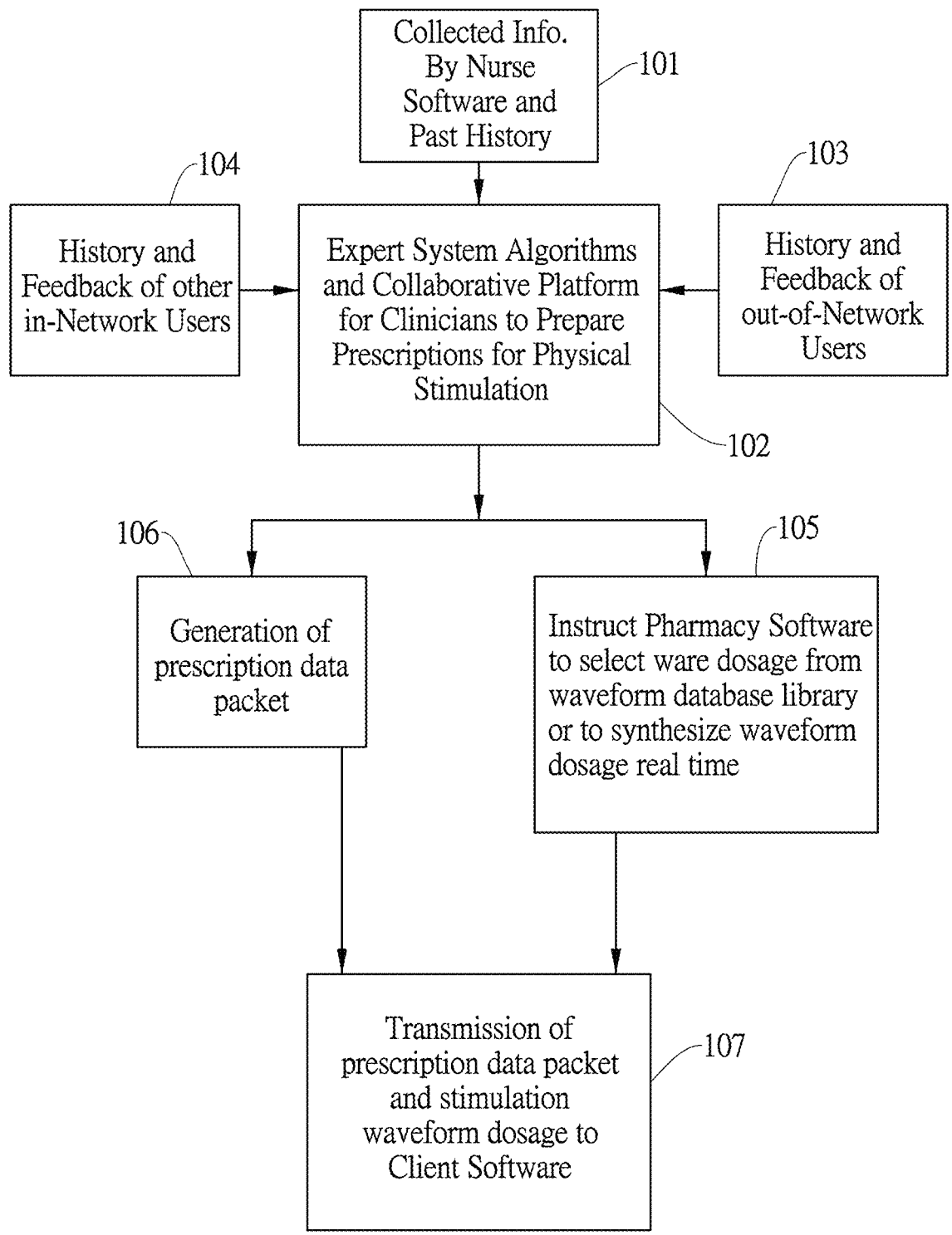
FIG. 2 shows the flow chart of an embodiment of our Clinician Software.

FIG. 2 shows a flow chart for the Clinician Software (B1 in FIG. 1)

102 includes an expert prescription software module and a collaboration communication module. The expert prescription software is a rule and knowledge based expert prescription software algorithm that, based on 101, the patient and symptom information collected by the Nurse Software (A1 in FIG. 1), 104, history and feedback of Users within the membership network (B4.2 in FIG. 1), and 103, history and feedback of Users outside of the membership network (B4.3 in FIG. 1), shall generate a prescription packet including instructions to the Pharmacy Software for preparing stimulation waveform dosage.

The collaborative communication module may support group online chat, group voice or video calls, or group conference calls incorporating additional filing sharing capabilities, so one clinician or a group of clinicians from different disciplines may interact among themselves and/or with the User, along with information from 101, 103 and 104, to finalize the physical treatment prescription for the User.

Access to a central database of all Users in order for the Clinician software or Clinicians to use not only specific history and treatment outcome data from one User, but from statistically and clinically significant data analysis from a broad range of Users.

The Clinician expert system uses these data to decide the prescription for a User. The detailed implementation of such a Clinician Software system may vary but all are designed following rigorous medical and clinical treatment modalities.

The diagnosis and prescription will be passed to the Nurse Software on the Client device for the User to accept or make adjustments. The simplest process shall not involve the two way communications which may require such semi human intervention such as online chat. But for certain paid services, this human intervention may be provided to finalize the physical stimulation treatment prescription.

Figure 3A:
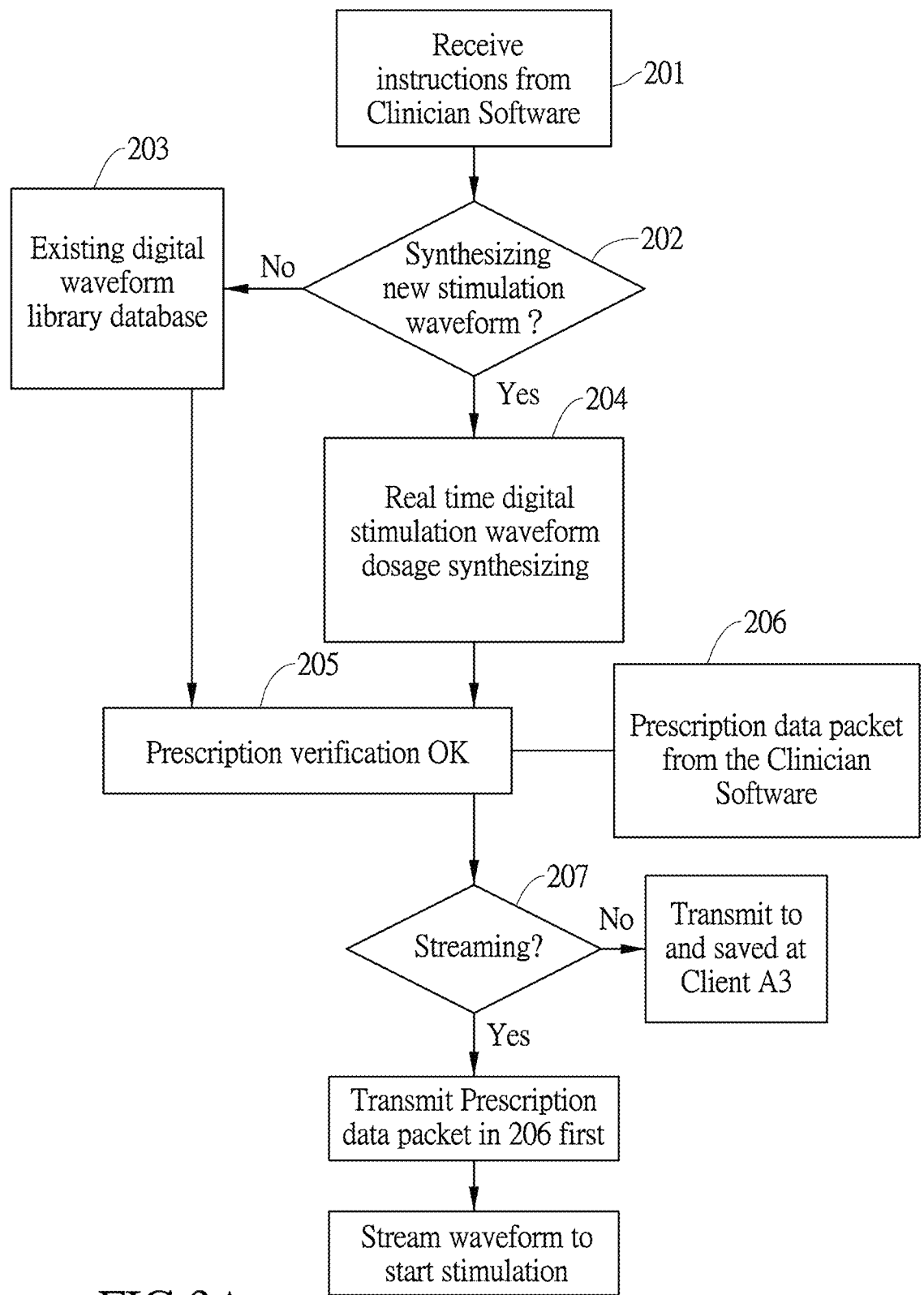
FIG. 3A shows the flow chart of an embodiment of our Pharmacy Software.
Figure 3B:
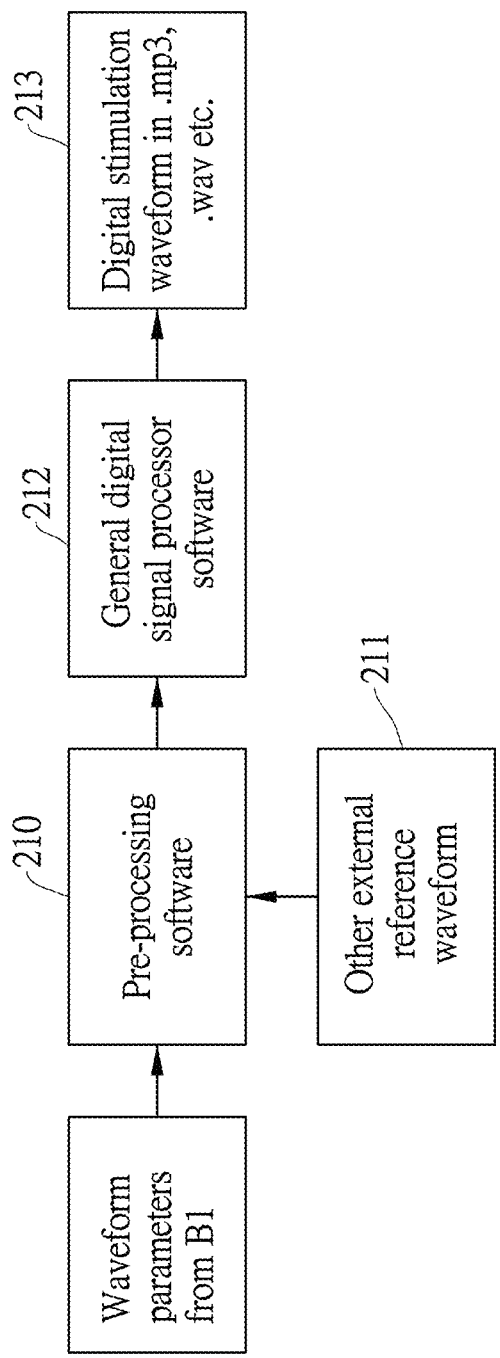
FIG. 3B shows B2.1 in FIG. 1—stimulation waveform synthesizer.
Figure 3C:
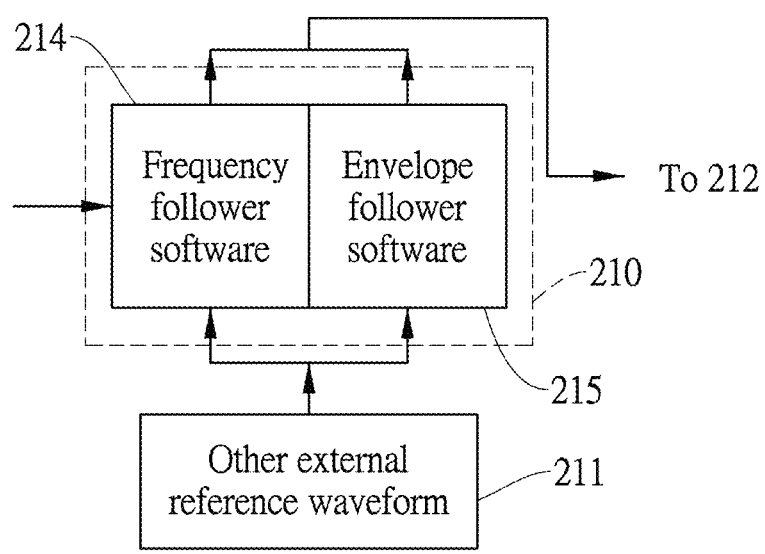
FIG. 3C shows pre-processor Software 210 in FIG. 3B.
Figure 3E:
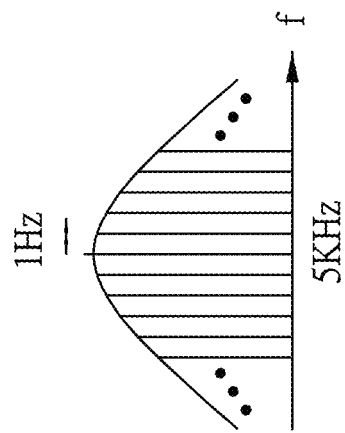
FIG. 3E shows the waveform obtained by amplitude modulation of a 5 kHz intermediate frequency carrier from a 1 Hz square wave train.
Figure 3D:
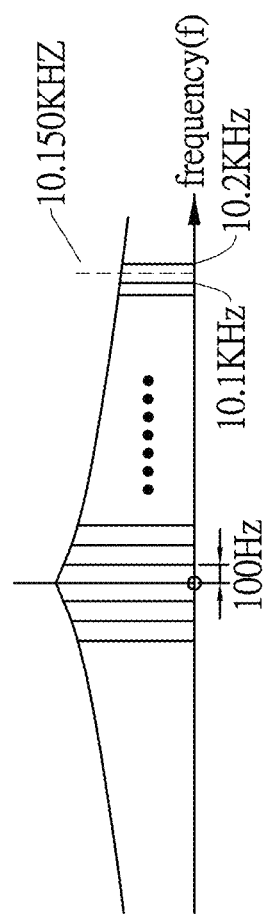
FIG. 3D shows that the frequency of the ID sinusoidal waveform and the periodic stimulus waveform do not overlap.
Figure 3F:
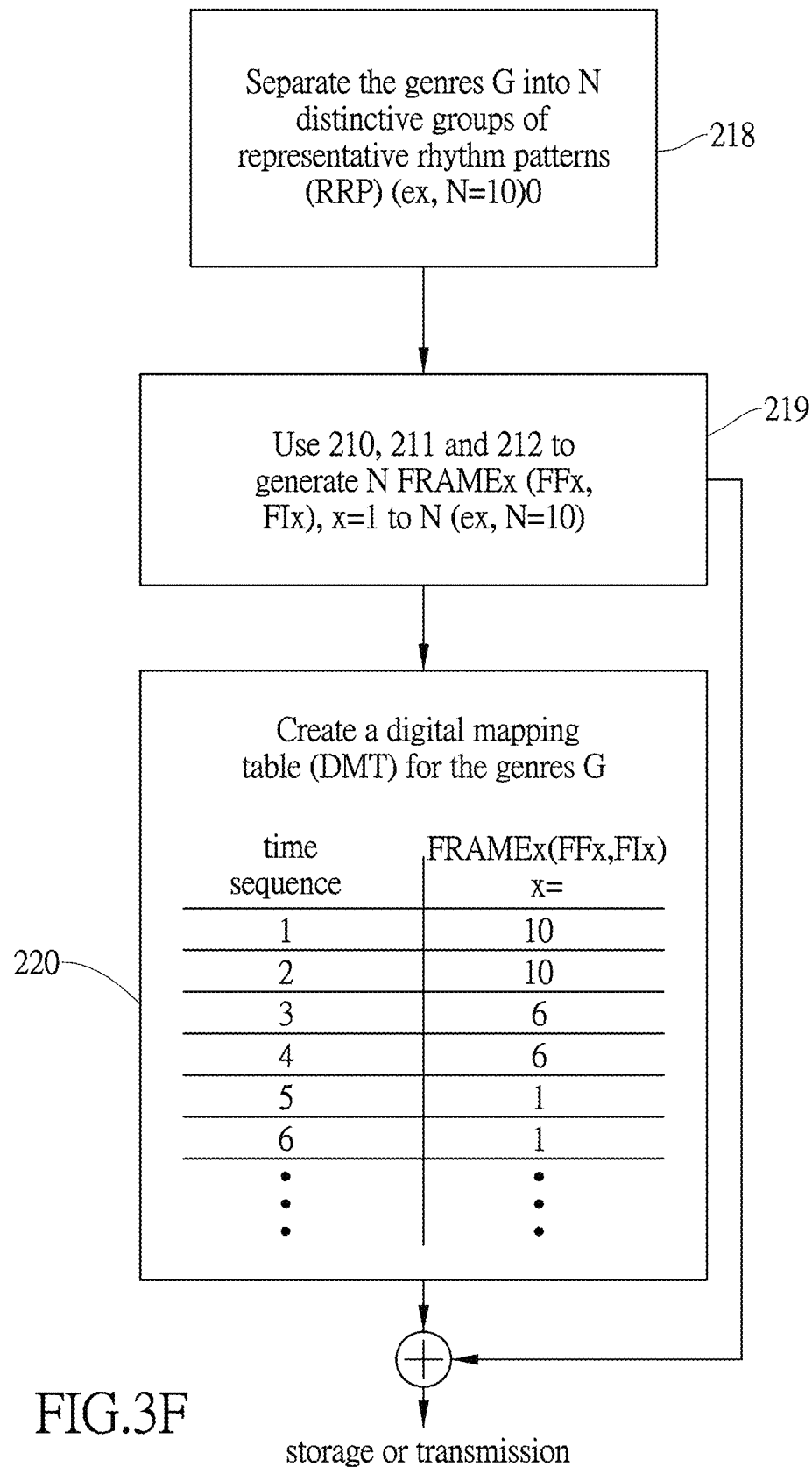
FIG. 3F shows B2.2 in FIG. 1—pre-synthesized stimulus waveform database.
Figure 3G:
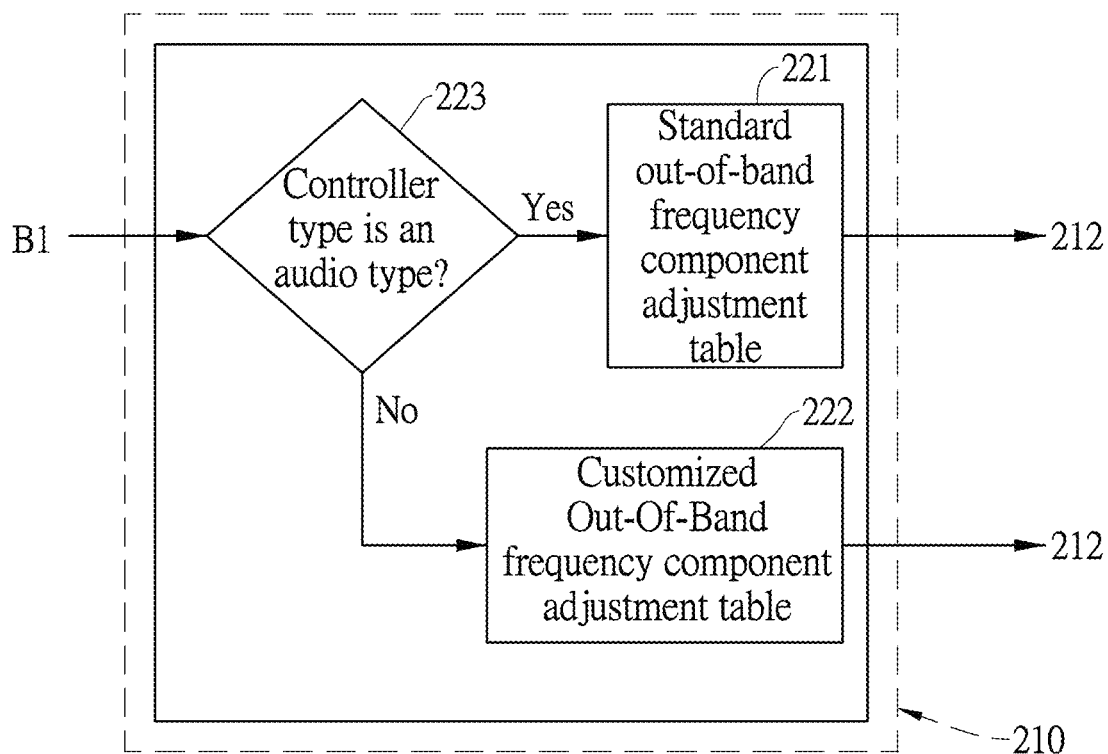
FIG. 3G shows another embodiment of the stimulation waveform synthesizer B2.1 of FIG. 1.
Figure 3H:
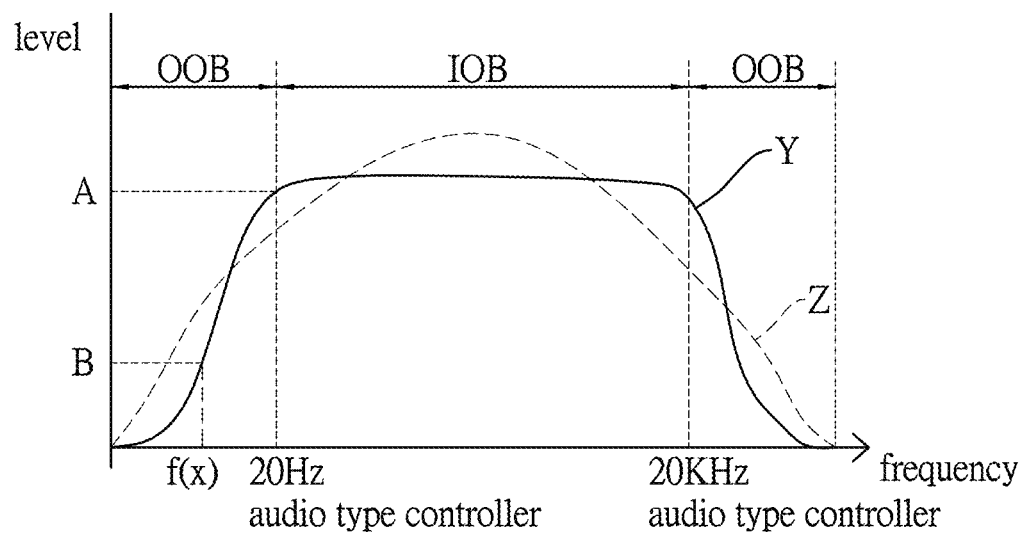
FIG. 3H shows the in-band and out-of-band (IOB, OOB) components of the bandwidth relative to a stimulus controller.
Figure 4:
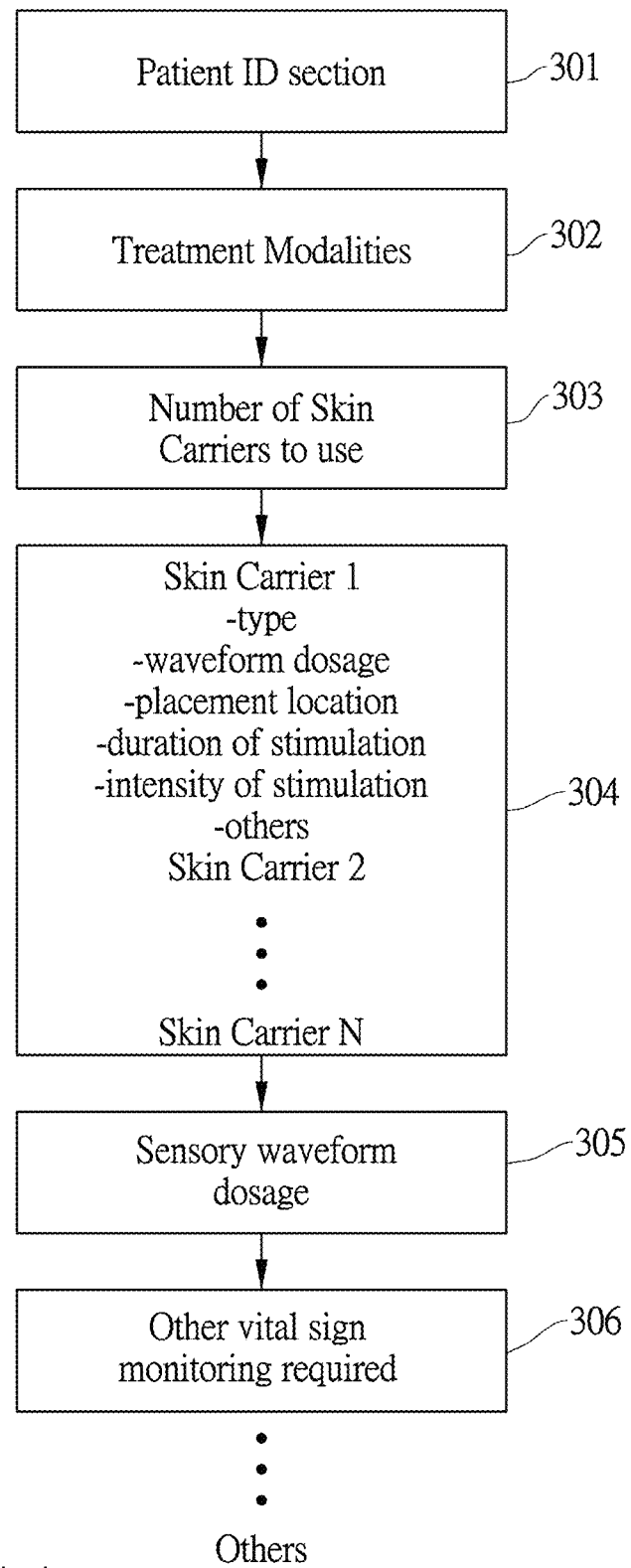
FIG. 4 shows an embodiment of the prescription data packet.

Physical Stimulation prescription includes a digital prescription packet 106, an example embodiment of which is shown in FIG. 4, and 105, a digital stimulation waveform dosage generated by the Pharmacy Software, certain embodiments of which are shown in FIGS. 3A-3H.

FIG. 3A shows an embodiment of the flow chart of the overall Pharmacy Software.

After the Pharmacy Software receives a prescription script from the Clinician Software 201, it will first decide in 202 if the prescribed waveform dosage may be available from the library.

If yes, then the waveform dosage is searched in and retrieved from the waveform library 203.

If no, then the prescribed waveform parameters are passed to the real time stimulation waveform synthesizer software 204 to generate the digital waveform dosage in a specified file format.

The Pharmacy software module 205 uses digital prescription packet 206 as part of the instructions from the Clinician Software to verify the waveform dosage from either 203 or from 204. Once verified, the pharmacy dispatch software module 207 checks if the waveform dosage is to be streamed real time to the Client software when the treatment starts, or is to be streamed and saved in the Client waveform library A3. For the latter, the complete digital prescription set will be immediately transmitted to the Nurse software. For the former, the digital prescription packet 206 will be first transmitted to the Nurse software so the Nurse software may begin to assist the User to select and place the carrier(s) per the prescription and once it is ready, inform 207 to start streaming the stimulation waveform dosage from 203 or 204 and the stimulation treatment session begins. Streamed stimulation waveform shall not be saved on the Client device.

Using Pharmacy Software (B2 in FIG. 1) to synthesize on demand in real time digital stimulation waveform (B2.1 in FIG. 1) or to synthesize off-line customized stimulation waveform dosages and store them in a database library (B2.2 in FIG. 1) is a major inventive method and system in our overall PSaaS service architecture.

To better explain these inventive methods and systems under the Pharmacy Software module, without limiting its broad applicability, we will use electrical stimulation embodiment to explain the inventive framework and methods and systems of software implementations.

Waveform approved by FDA and found effective for electrical stimulation falls into mainly:

a: baseband stimulation waveform containing pulse trains of various pulse widths and frequencies. The pulse width may be made different from one pulse to the next or from one segment to the next segment, each segment length may be varying, each pulse in a pulse train can have a different shape from one another, from square pulse to trapezoidal to sawtooth, mono phase or biphase, etc. Popular TENS, ENMS/EMS (Electrical Neural Muscular Stimulation or Electrical Muscular Stimulation), MENS (Microcurrent Electrical Nerve Stimulation), tDCS (Transcranial Direct Current Stimulation), tACS(Transcranial Alternating Current Stimulation) devices use these types of waveform.

b: amplitude modulated medium carrier frequency waveform such as BMAC (Burst Modulated Alternating Current) and IFC (Inferential Frequency Current). The frequency and intensity of the carrier waveform may vary for different treatment regiments. Baseband signal that is used to amplitude modulate the carrier frequency may vary, like a above, in its pulse shape, pulse duration and frequency of the pulse train.

Other than the pulse duration, shape of each pulse and frequency of a carrier waveform, the frequency of the pulse train may also vary depending on the planned treatment (for example, in commonly used TENS (Transcutaneous Electrical Neural Stimulation), a pulse train of low frequency with higher intensity for each pulse may result in slower onset of pain relief but the analgesia effect lasts longer, while a higher frequency of lower intensity pulses may result in faster pain relief onset but the analgesia effect does not last as long after the treatment session ends).

In addition to treatment efficacy consideration, adaptation reduction is also a consideration when the doctor software sends the prescription to the pharmacist software. For example, the history of this patient may indicate that its previous treatment was not as effective as expected and a low frequency high intensity pulse train waveform was used. So this time, the Clinician software may prescribe a waveform dosage consisting of a segment of low intensity pulse of higher frequency mixed with another segment of higher intensity pulse trains with lower frequency.

For efficacy consideration, another example is that it has been discovered by us that, as part of our inventive process, in many our internal clinical studies, for certain types of pain or chronic or acute ailments such as sudden or prolonged sleep disorder, a stimulation with pulse intensity and frequency of the pulse train rhythmed with music types favored by that patient may add to efficacy and reduce greatly adaptation and fatigue to the stimulation There are commercial products such as a music massage chair that synchronizes the rhythm of massaging rollers with the music rhythm. However, there was not any proposal to apply the rhythm to electrical stimulation waveform. We tested amplitude limited (for safety reason) direct baseband music signal, from 10 Hz to 4 KHz, to body stimulation. We also tested TENS pulse train of varying intensity and pulse frequency synchronized with the music for body stimulation. All these produce pronounced treatment efficacy improvement and fatigue reduction.

The architecture of stimulation waveform pharmacy software is based on the following two system premises:

1: all digital stimulation waveform dosage will be stored in commonly used digital audio file format such as .mp3, .wav, .midi and possible other commonly used audio formats used in voice communications, video and movies. This is due to our careful analysis of the waveform and signaling that enable today's various physical stimulation and, other than laser stimulation, they are inside the high fidelity audio bandwidth of 48 Khz. This is the case for all electrical stimulation, for magnetic stimulation and even for dynamic pressure (acupressure, reflexology, massaging, etc) and compression stimulation, the waveform used to control the varying pressure and compression is inside the audio bandwidth. A 10 Hz dynamic compression has a pulsed pressure change every 0.1 sec, which may already be so fast that our sensory nerves may have trouble following to produce beneficial therapeutic effects.

By standardizing our digital stimulation waveform format on these commonly used audio formats, the stimulation controllers may embrace an open ended design and not the close ended designs used in all today's stimulation controllers. Waveform inputs for stimulation controllers come from a connected Client device, or wirelessly from a Client device and are no longer limited by the basic digital stimulation waveform generated from a microprocessor and/or digital signal processor of each controller 2: All periodic digital stimulation waveform shall be saved in a short segment, called Snippet, throughout this patent application, that may be repetitively played back by a controller to provide a continuous physical stimulation lasting much longer than the duration of the Snippet. Since many proven physical stimulation waveform is of periodic nature, this file/data compression design will minimize the amount of data bandwidth required between the Host cloud server and the Client device.

For example, if the period of the waveform is 10 msec (or the frequency of the periodic waveform is 100 Hz), then the segment duration (called SD) may be of duration of 10 seconds, containing thus 1000 periods of the waveform dosage. How to choose SD depends on the waveform and its period, so that when the segment is loop play-backed, the stimulation waveform artifact from the end of one loop to the beginning of a new loop is minimized. If the period is 10 msec and we use a SD of 100 ms, the audio circuit may lag in response creating excessive artifact between the loop playback.

With these two important inventive designs as a basis, we will provide a couple detailed explanation of certain embodiment of the inventive methods and systems used in our Pharmacy Software.

FIG. 3B for Stimulation waveform synthesizer (B2.1 in FIG. 1)

Our pharmacy laboratory software is actually digital signal processing software that will take the waveform para e s from the Clinician software and synthesize a waveform into commonly used formats such as .mp3, .wav, .midi and others, depending on the fidelity of the waveform required and the frequency bandwidth of the waveform. This parallels how the drug may come in—pills, capsules, liquid and our stimulation waveform dosage may be delivered in these various file formats, for example, from common .mp3 file, to .wav where a more demanding treatment may require that the drug comes in more "purified (in our case, higher resolution)" form. In certain clinical applications or where a lot of wireless signals may be present, or for privacy or security reasons, the dosage of stimulation waveform may come in a proprietary or encrypted file format and not the commonly used file format.

We need to note that, our dosage may be delivered in such a common file format .mp3, .wav, .midi is due to the fact that the frequency spectrum of the most commonly used stimulation waveform classes, baseband ones and medium frequency ones, all fall with the high fidelity audio bandwidth of up to 44 KHz. For voice, the bandwidth is much lower at around 4 KHz, so is the lower fidelity music but for most today's audio encoder and decoder, it is capable of reproducing digital audio files into electrical audio signal up to 44 KHz bandwidth, which is more than sufficient for almost all our stimulation waveform that have proven treatment results.

For example, for a baseband TENS waveform, with a 100 micro second pulse width and pulse train frequency of 100 Hz, the frequency bandwidth needed is up to 10 Khz (see FIG. 3D), well within a modern day audio codec (encoder and decoder).

For a medium frequency carrier waveform of 5 KHz amplitude modulated by a 1 Hz square pulse train of 50% duty cycle, the bandwidth requirement is up to around 5 KHz, well with the bandwidth of the modern day audio codec too. See FIG. 3E.

This type of inventive way to deliver waveform dosage in common audio formats and use high fidelity low cost audio codec already built in smartphones, tablets, PCs and widely available for our stimulation controllers, shall result in inventive controllers that not only can deliver on demand personalized treatment waveform not possible with current close-ended controllers to achieve highly effective stimulation results, but to lower greatly the cost of the controllers.

212 in FIG. 3B shows a general digital signal processor software that may synthesize high quality digital stimulation waveform. 213 takes the output of 212, adds needed preamble and/or post-amble segment and select the proper time duration for the Snippet of that particular digital stimulation waveform dosage and output the digital waveform in the specified file format. The output 213 is thus digital stimulation waveform in commonly used audio file formats so that any standard digital to analog converter built in today's PCs, smartphones and tablets and in our stimulation controllers may readily convert our digital stimulation waveform into analog stimulation electrical waveform sent to our skin Carriers to effect physical stimulation treatments.

210 is pre-processor for 212. Based on the waveform parameters from B1, it does some needed digital pre-processing for 212. An embodiment example is to create in real time a rhythmic TENS waveform from a sensory digital music prescribed by the Clinician Software B1 or selected by the User. 212 in this case, as shown in FIG. 3C, include a frequency follower and an envelope follower.

Using 214 "frequency follower" digital signal processing software (as used by many media player to display a software "discrete frequency equalizer bands" or "discrete frequency spectrum bands") and 215 "envelope follower" digital signal processing software, 210 may perform the followings, in real time and offline, to create a randomized digital stimulation waveform and send it to 212 to be streamed or saved into our database library of rhythmic randomized stimulation waveform, start with the music and take a "frame" of the digital music file, perform a needed decompression (such as from .mp3 to .wave) of that frame.

take the converted uncompressed digital audio file of that frame and feed it into "frequency follower" 214 and "envelop follower" 215. Frequency follower DSP is a group of narrow band band pass digital filters and it will convert each time domain frame of the digital audio waveform into the intensity of each frequency hand. Take the average of the intensities in all the band pass digital filters and call it "frame frequency FFx where n is frame x". Envelope follower is a well designed narrow band low pass digital filter that will convert the frame of the digital audio wave file into a collection of digital intensity values of the envelope. Take the average of all these envelope intensity values inside the frame and call it "Frame Intensity FIx where x is frame x" so that, for each frame of the music waveform 211, for example in one embodiment, the average frequency FFx and signal intensity FIx of that frame may be determined in real time, which are then used by 212 to output a TENS waveform frame with, as an example of an embodiment, the pulse train frequency and intensity proportional to these averaged FFx and FIx from 214 and 215.

This embodiment is inventive so that the User receives indirectly the benefits of efficacy and reduced adaptation from a rhythmic electrical stimulation treatment but is not subject to the uncontrollable intensity and frequency in a rhythm audio waveform. Such a safe rhythmic electrical stimulation may also promote sensory resonance when the User also listens to the same audio during the rhythmic stimulation. Even though we use electrical stimulation to explain this inventive embodiment, the same may be applied to other forms of physical stimulation treatments.

FIG. 3F shows another embodiment of B2.2 in B2 to create and store generic rhythmic physical stimulation waveform.

Another inventive process in dispensing the dose of stimulation waveform is that, our pharmacy software does not need actual music to synthesize the stimulation waveform. All we need is for the User to provide us a list of the names of the songs he or she favors, or genres of music he or she prefers, and our expert system inside the pharmacy software B2 will be able to access our database of rhythmic pre-created digital stimulation waveform where rhythmic digital stimulation waveform are categorized based on different genres and themes. For example, if a user selects classic music category as his or her favorite, and if he or she may indicate further favorite composers, our pharmacy software may then pick the type of rhythm that is representative of the rhythm favored by the user and integrate such a rhythm into the synthesized waveform prescription for that user.

How our Pharmacy software create offline rhythmic digital stimulation waveform is another inventive method and system we will provide below further explanations on. This embodiment is applicable for pre-analyzed and stored rhythmic digital waveform dosage.

According to Wikipedia, there are over 1000 music genres and, for example, just for rock music there are about 150 genres within that group. There are also a large amount of genres for literature, visual arts, film, games etc. Therefore, we have devised an inventive method and system, called "stimulation waveform compression" (SWC), to produce rhythmic digital stimulation waveform that is bandwidth efficient for data transmission and storage space efficient while preserving the main rhythm of each genres to have beneficial effects during the physical stimulation.

For randomized digital stimulation waveform (RDSW), including rhythmic (Rhythm Driven Randomized Stimulation Waveform RDRSW) to, for example, a music, the total waveform has to be stored and transmitted to effect stimulation treatment. There is no data compression for these waveform.

RDSW or RDRSW=time domain sum of (FRAME1($FF1,FI1$)+FRAME2($FF2,FI2$)+ . . . +FRAMEx($FFx,FIx$)

where x is the number of the last FRAME.

For a genres driven randomized stimulation waveform (GDRSW), a waveform compression is possible and see FIG. 3B, for an embodiment of SWC for classic symphony genres:

218 will first analyze this genres and separate the genres into N representative rhythm patterns (RRP).

For example, in a symphony, usually it is expressed in four major movements:
an opening sonata or allegro;
a slow movement, such as adagio;
a minuet or scherzo with trio;
an allegro, rondo, or sonata;
for a finer categorization, we can use N=8 instead of N=4.

219 then uses 210, 211 and 212 to take a representative music piece and create a representative FRAMEx(FFx,FIx) for each RRP(RRP FRAMES).

220 then create a digital mapping table DMT for each Frame from these 8 basic Frames.

DMT and 8 Frames of basic digital stimulation waveform are combined for storage or for transmission.

GDRSW=time domain sum of FRAME1($FF1,FI1$)+FRAME3($FF3,FI3$)+ . . . +FRAME6($FF6,FI6$)+FRAME8($FF8,FI8$)+ . . . +FRAME3($FF3,FI3$), where the time domain sequences of all FRAMES are arranged based on the table DMT.

Assuming it is a 40 minute symphony, and each FRAME is 30 seconds with a file size of around (50M/(4*60=240 seconds))×30=6 MB for .mp3 format, the total file size of the RDSW to be stored or transmitted is no more than 50 MB, significantly less than the possible file size of 500 MB for a 40 minute symphony in .mp3 format. This is a significant saving in the file size that need to be stored and transmitted.

GDRSW can be TENS waveform (assuming pulse width remains the same throughout this RDRSW), BMAC waveform (assuming carrier frequency remains the same throughout this RDRSW) or IFC waveform assuming carrier frequency remains the same throughout this GDRSW), tDCS, tACS, MENS and any type of stimulation waveform.

Once a stored GDRSW digital packet shall be real time sent to the Client device on, for example, a smartphone, the Nurse software receives the GDRSW packet and will:

3.1 if the stimulation controller such as C1 is connected to the audio jack port directly, GDRSW will be assembled by the Nurse Software and sent by the Nurse Software to the DAC inside the smartphone and out comes the analog stimulation electrical signal sent directly to the analog audio port C1 is connected to for it to be used by the controller C1 as the source of stimulation waveform for stimulation treatment.

3.2 if the controller is connected, such as C2, to the Client device through a lighting or micro USB data port, or wirelessly connected to the Client Software in the smart phone such as C3, then digital RDRSW will be streamed directly through the digital port or witlessly to the controller and the DAC (Digital to Analog Converter) inside the controller will start converting the digital RDRSW into continuous analog stimulation electrical waveform, based on the DMT table, and send it to the carrier(s) to stimulate the body.

Note that the signal synthesizer software shall be a signal synthesizer software engine that can multi task to synthesize multiple stimulation waveform dosages concurrently, and all parameters of the dosage waveform shall be compared with each prescription in 205 before it is dispensed to the Client device for the dosage to be used by the Nurse software for stimulation.

Also our algorithm includes not only matching the rhythm of stimulation to the rhythm of favorable songs, but it may also use the opposite approach of balancing the rhythm of stimulation against the rhythm of favorable songs. For example, if the favorable songs are hard rock or raps, then if a sleep disorder treatment is sought by the user, then more steady soothing rhythm of opposite groups of music styles may send unique messages to the brain for certain healing and calming effects effective for the target treatment.

Notes: if someone likes Mozart, then maybe just use the rhythm of one of the Mozart music in this treatment and use the rhythm of another Mozart's music in the next treatment Another inventive step in our rhythm selection and decision is that our system will be able to decide on the proper rhythm to use based on favorable pictures and videos by a user.

For pictures, either send us some pictures and based on an image/pattern recognition algorithm we use, such as redundancy decoding algorithm (see U.S. Pat. No. 4,761,782 by one of the inventors of this patent application for details), we will be able to get an idea the type of visual rhythm favored by a user.

For example, ocean or blue sky has very high redundancy and so pictures of these types means that the person favors easy rhythms. Added color recognition, our expert system will be able to further distinguish certain scenes such as sky, ocean, forest, prairie, etc. Facial pattern recognition, aided by the genres information, can also tell if the user favors males, females which translates into the rhythm types likely effective for that user.

Movies and videos are other important traits for personalities which in turn are correlated to the rhythm that may be the most effective for that user. Our inventive process will use the audio portion that goes with the video to better understand the genres and type of rhythms favored by a user. The same we proposed in FIG. 3B for music genres driven rhythmic stimulation waveform may be applied to genres for films, movies, games, visual arts and others.

This is particularly useful if the user undergoes a stimulation treatment while using either audio, pictures or video to create a sensory stimulation to resonate with the physical stimulation of nerves, muscles and vital points to improve treatment efficacy. Our app can take the picture, audio track of the video and audio and on demand vary the rhythm of the stimulation to effect a better treatment result.

FIG. 3F and FIG. 3H show another embodiment of B2.1 in FIG. 1.

Another embodiment described herein is an inventive step we propose to overcome the need of matching the bandwidth of the stimulation signal generated by general digital signal processor 212 and 213 residing in the Host and the bandwidth of both the signal processing software and circuits such as audio Digital-to-Analog-Converter(DAC) used in the Client (see A in FIG. 1) and the bandwidth of the software and circuits such as audio DAC used in the Controller (see C in FIG. 1).

The stimulation waveform of a traditional stimulator is usually predetermined so the bandwidth of the software and electronic circuit used in that stimulation controller is designed to match the signal bandwidth of the stimulation waveform. But in our inventive PSaaS system, the generation of the stimulation waveform at the Host by 212 and 213 may be done on demand and its bandwidth has to be, also on demand, be adjusted based on the Controller C to be used, so that the fidelity of the stimulation waveform is optimally preserved till it is delivered to the Skin Carrier (see D in FIG. 1). Our inventive step described in FIGS. 3G and 3H is proposed to make this happen in an on-demand way.

In essence, our inventive step proposes that the stimulation waveform prescribed by the Clinical Software be pre-distorted, if needed based oil a built-in algorithm, by 210, 2012 and 213, so that, after this pre-distorted stimulation waveform passes through the processing of the software and the circuits of both the Client and Controller, the stimulation waveform is as close to the prescribed stimulation waveform by the Clinician Software as possible, before it is delivered to the Skin Carrier for stimulation uses.

Please see FIG. 3G for an embodiment. 223 inside 210 will first check if the Controller type is an audio type or a customized type as provided by the Clinical Software. If it is an audio type controller, the standard out-of-band frequency component adjustment table for an audio type stimulation controller, either C1, C2 or C3, denoted as SOOB (222), will be used and sent to 212 and 213. If it is a customized type stimulation controller such as C2 or C3 in FIG. 1, then the Customized Out-Of-Band frequency component adjustment table, denoted as COOB (221) for that controller type will be used and sent to 212 and 213.

In the simplest embodiment, 210 will not perform a frequency domain digital Fourier transform to decide if there are appreciable out-of-band frequency components based on the waveform parameters sent from B1. This simplifies the software operation based on the assumption that, if there is little or no out-of-band frequency components, boosting a very low level frequency component by multiplying its levels with an adjustment factor AJ(fx) (see FIG. 3H) will still yield a very low level of frequency component, resulting in a negligible distortion for the stimulation waveform, However, if high level of signal fidelity is needed, then an additional step in 212 of transforming the time domain signal based on the waveform parameters from B 1 into the frequency spectrum, determine, based on a pre-set threshold for fidelity, if there are appreciable out of band frequency components, and, If not, then steps in 221 to 223 are not needed to avoid introducing any distortion into the stimulation waveform.

We will use a standard audio type controller as an example.

For example, the bandwidth of a standard audio player, in a smartphone or tablet, or an MP3 player, is from 20 Hz to 20 KHz. Therefore, frequency range below 20 Hz to DC 0 Hz, and frequency range higher than 20 KHz are considered Out-Of-Band (OOB) frequency components. Please see curve Y in FIG. 3H for such a depiction.

If the stimulation waveform has a frequency spectrum such as curve Z in FIG. 3H, those frequency components below 20 Hz and above 20 KHz are OOB frequency components. Since the frequency components in the OOB range will be attenuated more than those frequency components Inside of the bandwidth (IOB), the output stimulation waveform in the time domain will therefore be distorted once the stimulation waveform goes through the audio controller circuits. Our inventive step is proposed so that we can solve this problem of waveform distortion.

In the SOOB or COOB, the adjustment at each OOB frequency component, AJ(f(x)) could be, as an embodiment example, the ratio of the IOB level A to the level B at that OOB frequency fx, as seen in FIG. 3H: $AJ(f(x))=m*(A/B)$ where m is a constant coefficient that can be set in order to achieve the best result.

FIG. 4 shows an embodiment of the prescription packet.

Shown in FIG. 4 is an embodiment of the accompanying digital prescription data packet (see 206 in FIG. 3A). This is merely an example of the embodiment and an example only. The actual content of the prescription packet may vary greatly depending on the type of the physical treatments and many other considerations. But this example of the embodiment may provide a good overview of the structure of this digital prescription in our proposed PSaaS system—

301 shows a patient ID data block and this may include many important information for the Nurse Software to make sure the intended User of this prescription matches the actual User.

302 shows the stimulation treatment modalities.

Under 302, there are three main data section in this embodiment:

303 shows the number of skin Carriers that will be used for this stimulation treatment:

for each Carrier, 304 shows the main content of the prescription type of the Carrier for example, transcutaneous (electrical, magnetic, compression, etc), percutaneous (electrical, magnetic, laser, heat, localized pressure, etc h). hybrid, specialized, etc stimulation waveform identification, including if it is streamed, digitally saved in a Client device, etc dosage of the stimulation by the said Carrier (intensity, duration of each stimulation, how many treatments per day, how many days of a complete treatment session. Etc, similar to the information one receives from the pharmacy when one picks up the prescription drug.)

how the dosage will be administered (for example, where to apply on the body, for how long, intensity level (such as it is fixed, or tolerable by the User, etc).

305 shows the sensory waveform dosage prescription, audio, picture, video, etc.

306 shows if any vital sign monitoring is needed for the stimulation treatment session.

Figure 5:
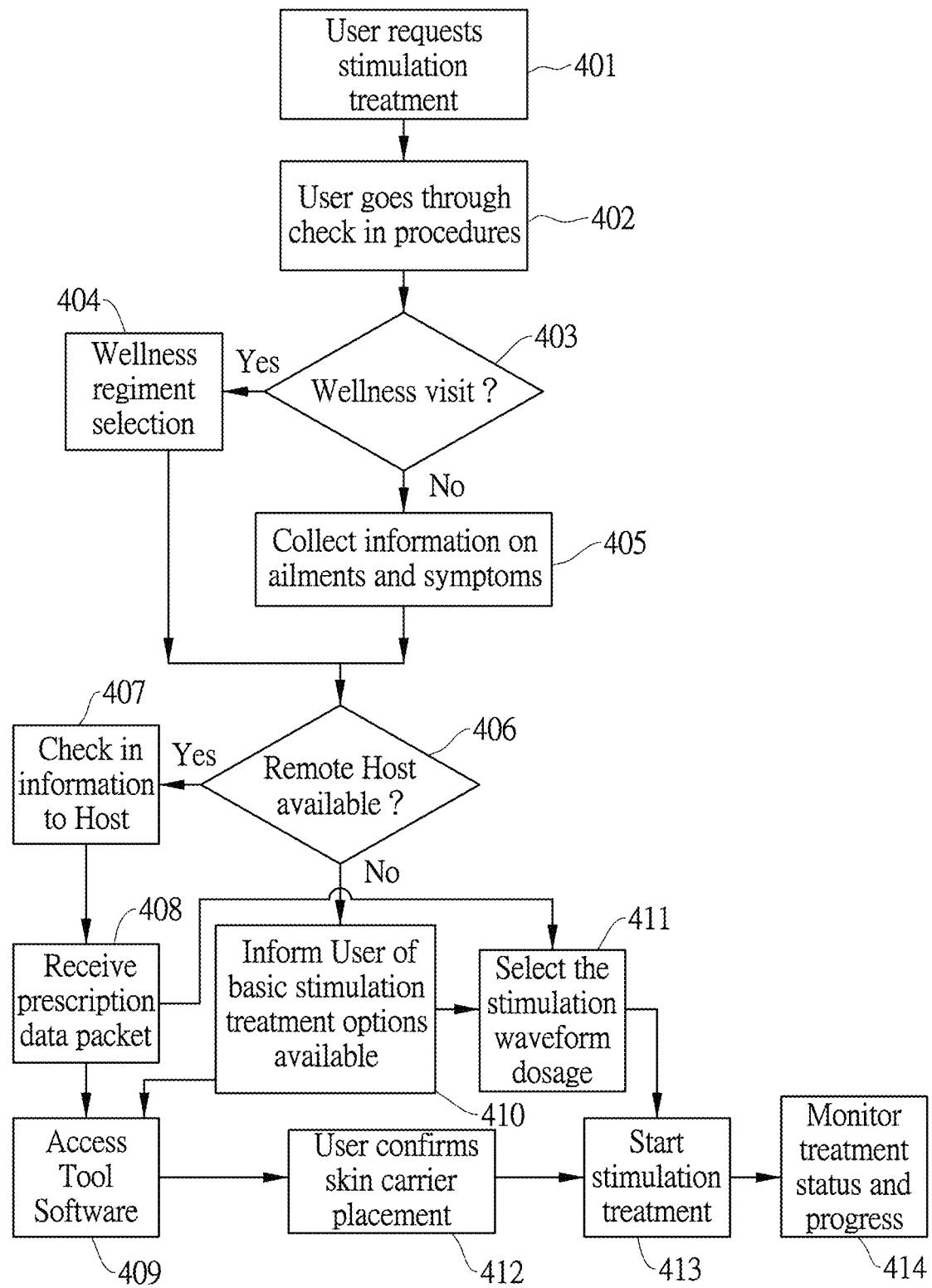
FIG. 5 shows the flow chart of an embodiment of the Nurse software.

FIG. 5 shows an embodiment of the flow chart for the Nurse Software.

401 shows the first step Nurse software interacts with a User

402 shows how the Nurse software checks in the User. just like the patient profile form someone has to fill out completely when she/he sees a new doctor the first time, such as including gender, age, medication currently taken, other medical conditions. These data will be periodically updated by the user.

In addition to the above standard personal profile, in order to effect better and safe stimulation treatment, we will also ask user to provide further information on, for example, if he or she has a pacemaker, if she is pregnant, etc, particularly related to electrical, magnetic or electromagnetic stimulation.

What type of skin Carriers the User has (Please see Tool Software section for more information how this is done.)

what type of stimulation controllers the User has (Please note that our PSaaS may support third party physical stimulation devices as it is a general service and knowledge platform to help broaden the uses of physical stimulation treatments to better User's overall wellness or health.)

vital sign devices User has.

And Others

403 may try to decide if User is seeking a treatment for wellness purposes or for ailment relief or disease and pain relief treatment.

404 shows a section for choices of wellness regiments. This is an important purpose of our PsaaS service, to provide an intuitive and easy to use service platform and inventive software tools and, with inventive hardware stimulation controllers and skin contacting Carriers, so that, for the first time, a User and Clinician may work together to effect safe and personalized physical stimulation treatments for Users to achieve wellness and disease prevention.

if the User is seeking treatment for certain aliment; 405 shows a step where the Nurse software shall collect important information about symptoms and conditions of the ailment from the User.

Since our proposed PSaaS service has to meet basic stimulation treatment needs with or without the Host server, 406 shall check if the Host is accessible during the check in process.

If not, in 410 Nurse Software shall access A3 in FIG. 1 and inform User basic physical treatment modalities available, and User shall make a selection. All these modalities are medically safe and within the FDA guidelines.

Figure 6A:
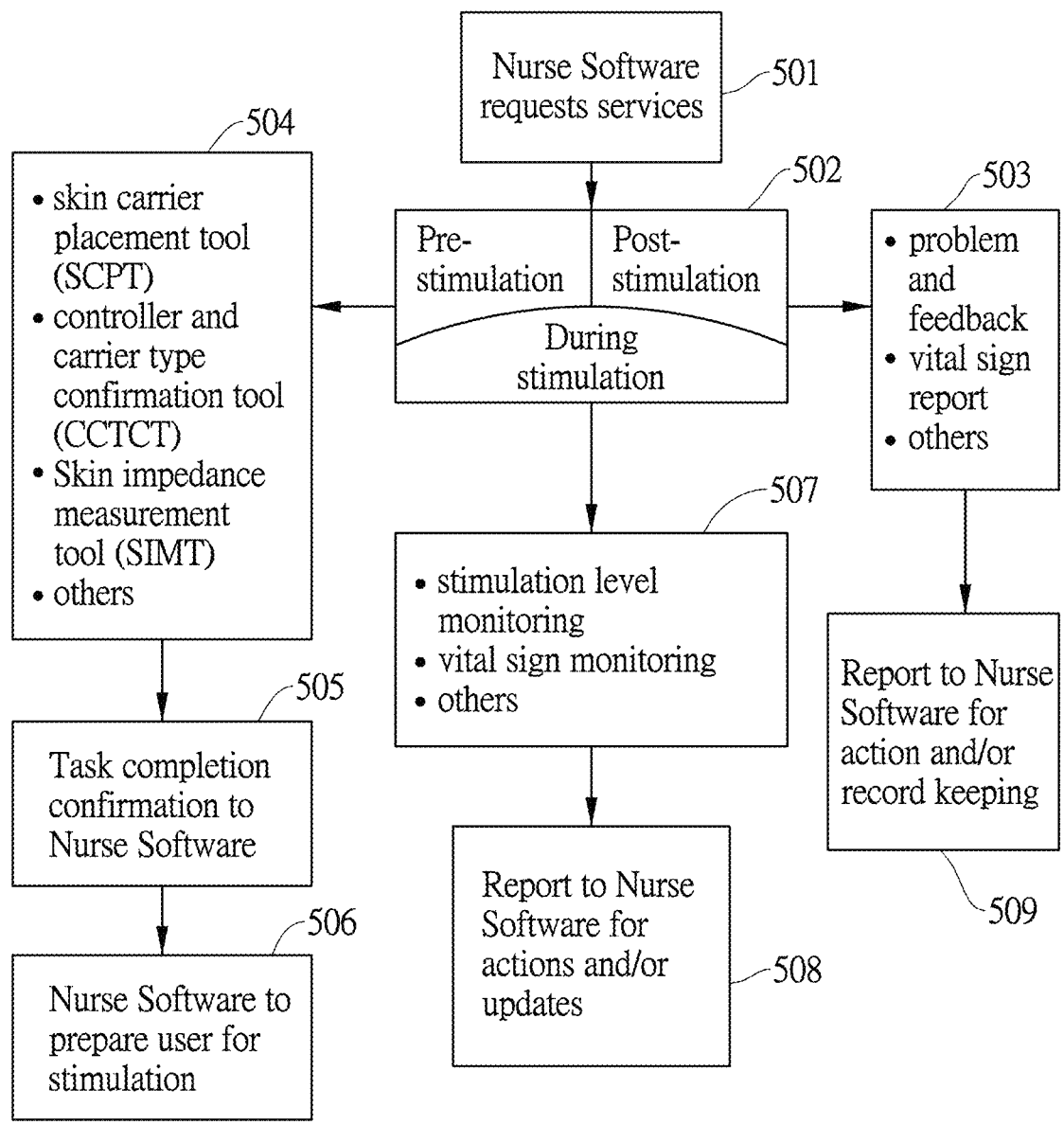
FIG. 6A shows the flow chart of an embodiment of the Tool software.

After 410, the Nurse Software shall in 409 access The Tool Software described in FIG. 6A to select the skin carriers to use, and to guide the User to place the selected skin carriers on the correct places on his or her body. The User will confirm to the Nurse Software the skin carriers have been successfully placed in 412.

Then in 411, the Nurse Software shall select and prepare the stimulation waveform dosage selected for this treatment.

Once both 411 and 412 are completed, physical stimulation in 413 starts, with continued monitoring by the Nurse software done in 414. If the Host is available in 406, the Nurse software in 407 send the collected check-in information and send them to the Clinician Software on the Host B1.

Once the prescription data packet (B3 in FIG. 1) is received by the Nurse software in 408, the Nurse Software shall go through processes 409 to 412, as above, to reach 413 and 414 when the stimulation treatment starts and the Nurse Aware continues to monitor the treatment.

FIG. 6A shows an embodiment of the Tool Software.

Tool Software is a very important part of our PSaaS service, in order for the Clinician Software to prescribe correct stimulation treatment modalities that may effect relief of pain of discomfort, or to effect maximum wellness benefits, for a User, for the Nurse Software to assist the User to properly apply the skin carriers onto the body, to deliver the correct stimulation waveform dosage to the User and to monitor the progress and status of the physical stimulation treatment session, and provide reports, feedback and needed followups after the stimulation treatment.

FIG. 6A show a high level flow chart of an embodiment of the Tool Software.

The Tool Software 502 is to decide if the tools shall be used before, duration or after a stimulation treatment when a request from the Nurse Software is received in 501.

If the Tool Software is requested before a stimulation session, a menu of Tool Software that are available will be shown in 504.

More tools shall be made available over time, but listed in herein 504 are three basic Tools that include inventive methods, systems and processes that we will explain in further details Skin Carrier Placement Tool (SCPT): Where to apply the skin carriers may affect greatly the treatment outcome. Unless the physical treatment is administered by a Clinician who will be able to apply the skin carriers correctly, a User himself or herself may not be able to do that relying only on user manuals that come with the stimulation controller or skin carriers. To make our PSaaS service effective and useful for Clinicians and Users, we have to use inventive methods and processes to provide a SCPT tool to Clinicians and Nurse Software. Please see FIG. 6A for explanations of an embodiment.

Skin Carrier and Stimulation Controller Type Confirmation Tool (CCTCT):

The Clinician Software has to know the type of stimulation controller and skin carriers a User has in order to prescribe the proper stimulation treatment modality.

User selects from the menu the type of carrier(s) he or she has.

If not sure, take a picture of the serial number and/or barcode of the controller and carrier set and our CCTCT Software shall be able to decide what stimulation controllers and skin carriers the User has. If the stimulation controller or the skin Carrier set has a built in wireless NEC tag, our CCTCC Software shall be able to read off the tag and determine its type, if the Client device has a built in NEC scanner and reader, which are found already in many current smartphones and tablets. For PCs and other devices, a connected external NFC scanner will be needed.

Skin impedance Measurement Tool (SIMT):

This tool shall be very useful for the Clinician Software to prescribe the correct dosage of the stimulation waveform and important for stimulation safety requirements. Please see FIGS. 15A to 15D for more detailed descriptions of some embodiments.

Vital Sign Collection Tool (VSCT):

Our overall Client Software in the Client device may work compatibly with software and Apps of other vital sign monitoring devices, so that, if any vital sign information is needed and compatible vital sign collection software and Apps exist, they can be collected by our VSCT and used by the Clinician Software to better prescribe the stimulation treatment modality and stimulation waveform dosage.

505 is a process where the Tool Software shall report to the Nurse Software when it completes the requested tasks and provide the Nurse Software the data, and the Nurse Software may start the stimulation as indicated in 506.

If the request by the Nurse Software is during the stimulation session, the Tool Software available will also increase over time, but shown here in 507 are some useful basic tools that will make PSaaS service effective and safe:

Physical Stimulation Level Monitoring (PSLM): Using sensors built in the skin carriers, physical stimulation level, such as current level in electrical stimulation, magnetic field strength in magnetic stimulation, temperature in heat stimulation, pressure level in the pressure and compression stimulation, and others. Please see our descriptions in this patent application how PSLM may be accomplished for different types of stimulation controllers.

Vital Sign Collection Tool (VSCT):

At this stage, VSCT is to collect vital sign data from the software and Apps in the Client device of the compatible vital sign collection devices to ensure efficacy and safety of our stimulation treatment by the Nurse Software.

And others.

In 508, the process of these data from monitoring activities be sent to the Nurse Software for updates and actions when needed.

If the request from the Nurse Software is after the physical stimulation session, 503 shows a couple general tools that are useful: problem and feedback report tool, vital sign report tool, and many others that may be added.

509 shows that these reports are then sent to the Nurse Software for actions and record keeping purposes.

Figure 6B:
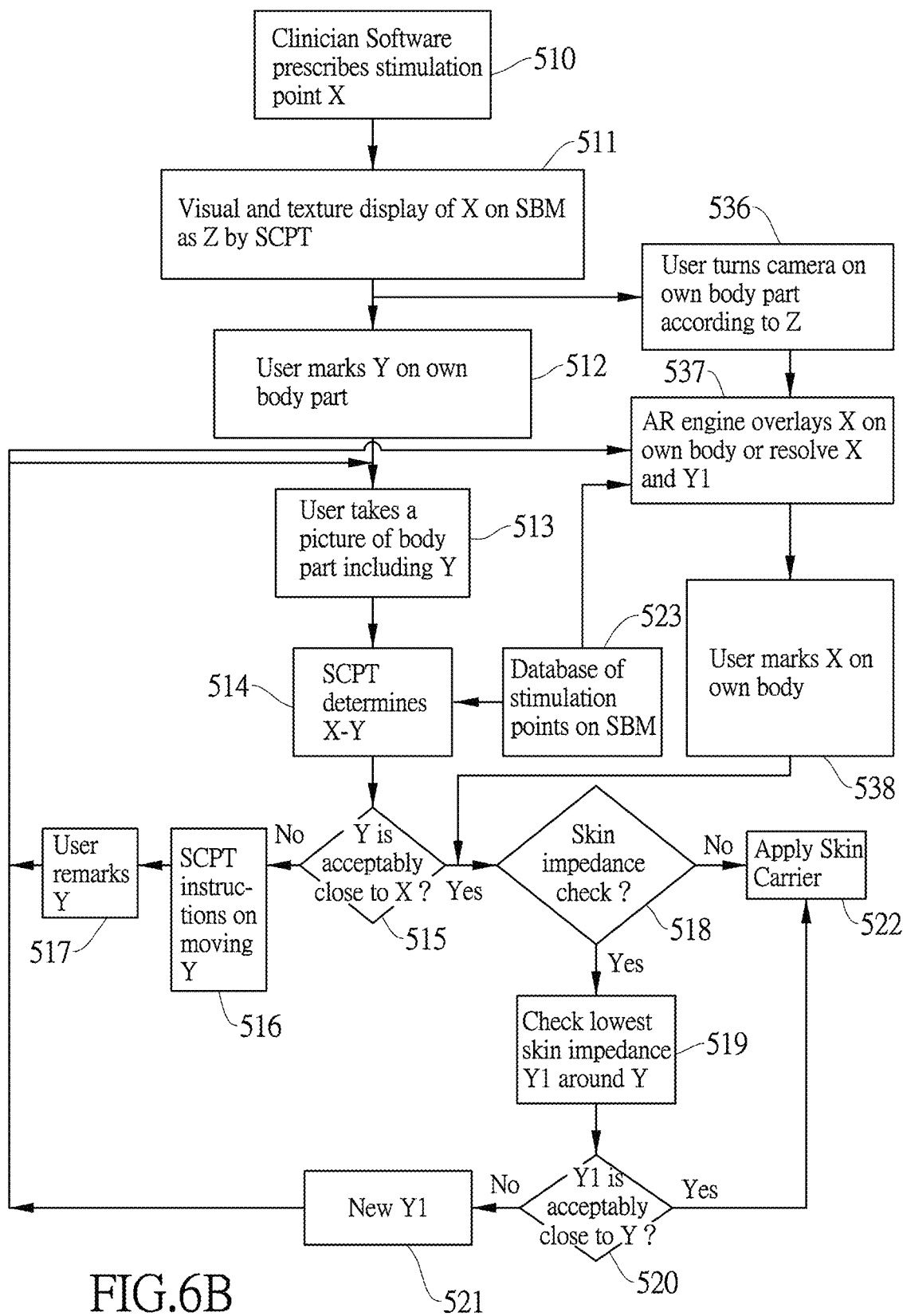
FIG. 6B shows the flow chart process of localizing points of stimulation for the User based on Clinician Software prescriptions.
Figure 6C:
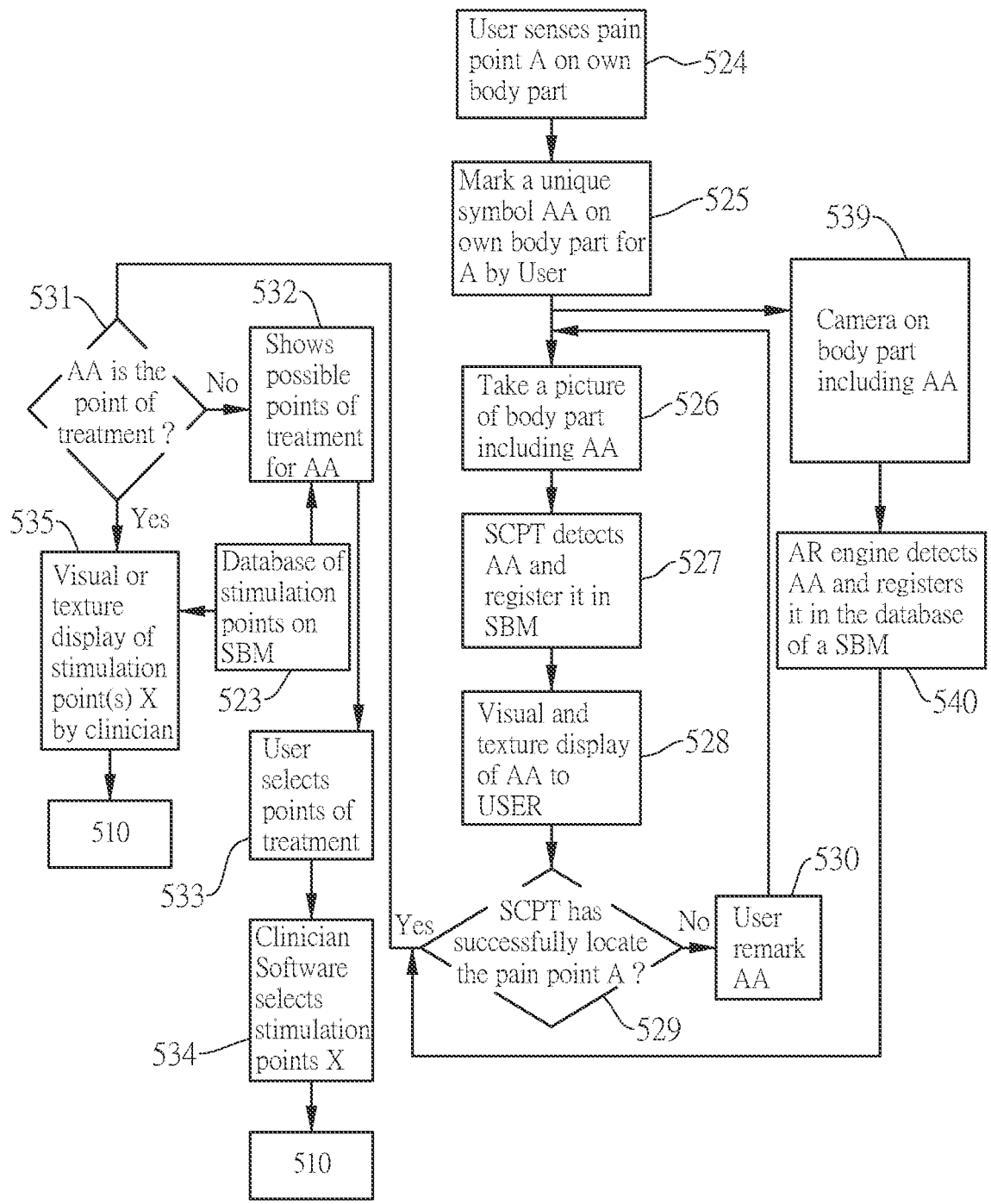
FIG. 6C shows the flow chart process of localizing points of stimulation for the User based on pain points.

FIGS. 6B and 6C show an embodiment of our imaging and sensing Tool Software to assist User place Carriers on the body (SCPT).

SCPT is a core Tool Software and very important in the efficacy and safety of each stimulation treatment.

First shown in FIG. 6B is an inventive routine we devised to locate a stimulation point X prescribed by the Clinician Software:

510 shows the Clinician Software to prescribe a stimulation point X on the body.

In 511 our SCPT software make a visual and/or texture display of X on a standard body model (SBM) and represents the display by Z.

Based on 511, User shall in 512 use, for example, an erasable marker, to mark a unique symbol instructed by SCPT on his or her body part he or she believes is the X on a SBM. Call this marked location Y.

User in 513 takes a picture of own body part including Y. In order to assist SCPT software with body part recognition, pattern recognition, scaling and matching, and other image processing needs, a reference sticker or marker may need to be placed in the target body part so SCPT software may use the size, angle and orientation and other geometrical information of the reference sticker/marker to determine camera angle and distance between the camera and the target body part, so it is easier for SCPT to scale and adjust the picture of the body part to match SBM in order to better register the stimulation point X on the picture of the User's body part. We call this process Scaling Reference (SR) and may refer to this term in other places when the same process shall be used.

SCPT software then, based on 523 the database of the standard body map of stimulation points (for example, sensory nerve endings, peripheral nerve points, acupuncture/acupressure acu points, reflex zones/points, etc), and built-in body part recognition, scaling based on estimated camera angle and distance relative to the intended body part, pattern recognition and smart algorithms, determine the degree of X-Y.

If SCP 17 determines that X-Y is not acceptable, which means Y is not the acceptable point of stimulation on the User's own body, SCPT shall issue an instruction in 516 to User how to move the marked Y closer to X.

In 517, User shall erase Y and remark Y in a new location based on 516.

The process then goes back to 513 to repeat the same process until SCPT in 515 determines Y is acceptably close to X.

Once SCPT determines the correct stimulation point Y, the process moves to 518 to decide if a skin impedance measurement is needed to verify the stimulation point Y. This decision may be made by the Clinician Software, or may be left for the User to decide.

Figure 15A:
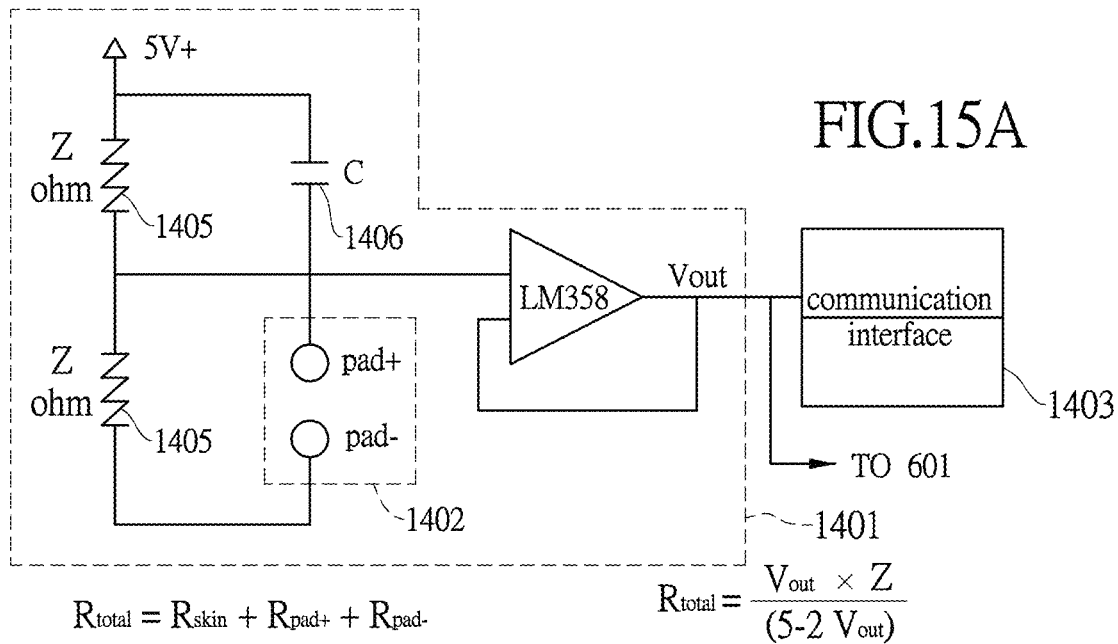
FIG. 15A shows an embodiment of a circuit for measuring skin impedance.
Figure 15B:
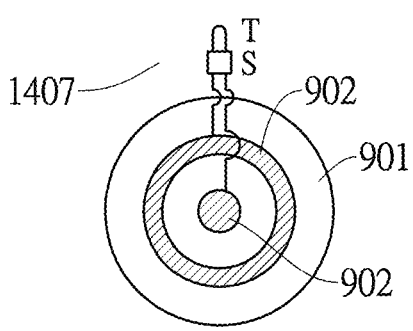
FIG. 15B shows an embodiment of a skin carrier for measuring skin impedance.
Figure 15C:
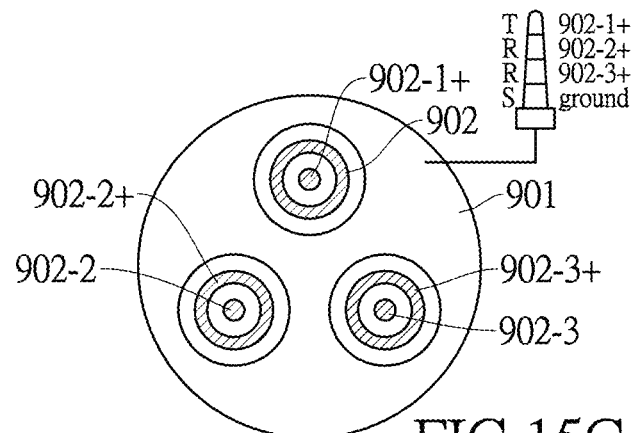
FIG. 15C shows an embodiment of a skin carrier for measuring minimum skin impedance.
Figure 15D:
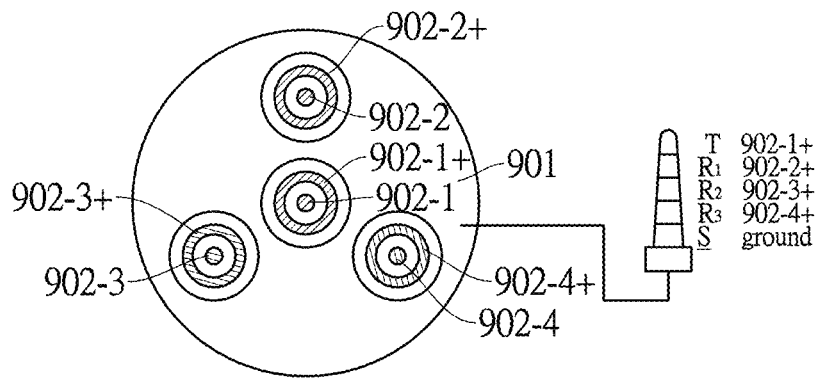
FIG. 15D shows another embodiment of a skin carrier for measuring minimum skin impedance.

If a skin impedance measurement is needed by 518, then using the skin impedance setup including the stimulation controller and the skin carrier shown in FIGS. 15A to 15D is used around Y in 519. For example, the measurement using a 4 pad skin carrier as shown in FIG. 15D may indicate Y1 where the lowest impedance was obtained.

If Y1 is acceptably close to Y based on instructions by the SCPT software and the Clinician Software, then stimulation point Y is confirmed and the process moves to 522 where the skin carrier shall be applied to. Please note that the size of a regular skin carrier is usually at least several millimeter wide or long, so unless the stimulation treatment prescribed a custom skin carrier that is much smaller than millimeter, usually at this stage Y and Y1 are acceptable in most cases.

Following 519, if Y1 appears to be sufficiently far away from Y, then on the instruction of SCPT to repeat the point localization process, User may erase Y and mark Y1 on own body part with again the unique symbol acceptable to SCPT for pattern recognition uses, and the process returns to 513 to reconfirm Y1.

FIG. 6B is an inventive and pragmatic method to locate a point of stimulation based on the reference stimulation point maps on an SBM. The recent emergence of Augmented Reality may be applied to our process to make it potentially faster, simpler and even more accurate. What makes Augmented Reality useful are built in object recognition, scaling based on camera angle, distance, orientations, etc, pattern recognition, local location (such as a pointer coordinate inside the camera view) recognition and general location recognition and tracking (such as GPS like location tracking, etc) and it is our intention that our inventive process shall be equally applicable to an AR based process.

For a quick reference, if AR is used, after 511, the process moves to 536, where User turns the Client device camera on the body part Z shown in 511.

In 537, AR software engine shall overlay, after object recognition, scaling based on camera angle, distance, orientations, etc, pattern recognition, local location (such as a pointer coordinate inside the camera view) recognition and based on the database 523, X on the live camera image.

In 538, the User, holding the Client device steady or using a holder to hold the Client device and the camera steady, may use a marker to mark X right on his or her body part where the overlaid X from AR is.

As long as the camera and the body part is held steady in the processes 536 to 538, the marked X should be the correct X SCPT intended, and the process moves on to 518.

As one can see, AR routine appears a lot simpler and efficient than the image based process from 512 to 518. However, AR is still an emerging technology and may need more time for its perfection. Therefore we describe the practical imaging process of SCPT for immediate practical application and for its inventive process to be equally applicable to the AR process.

FIG. 6C shows another important process how to locate stimulation point X from pain points indicated by a User.

Traditionally, a User describes his or her symptom and Clinician Software shall, as part of the stimulation treatment prescription, prescribes the group of stimulation points X's.

However, in physical stimulation, it is possible that the User may indicate "pain point(s)" to the Nurse Software first. There are two types of pain points:

Pain points that are also points of treatment. For example if one feels pain in the lower back, then he or she may try to show that pain point and that is also the point for treatment.

Pain points that are not points of treatment. For example, one may gently apply pressure on, for example, some pain spots on the back of the hand between the middle and small finger, and that pain point actually indicates a sore shoulder. This is common for treatment regiments based on eastern modalities such as using meridian theories for acupuncture and acupressure treatment, and for such treatment modality such as reflex zone stimulation on feet, hands and ears.

Therefore, we put together in FIG. 6C an inventive process to determine stimulation points X's based or pain points.

In block 524, pain point A is located by User.

User in 525 shall use an erasable marker to mark A on own body part with a unique symbol, called AA, acceptable to SCPT for pattern recognition uses.

User then in 526 take a picture of the body part including marked AA. SR technique described in 513 shall also be used.

SCPT shall in 527 recognize the body part and perform pattern recognition and they try to register AA in its database of stimulation points.

In 528 SCPT will display AA back to the User visually and/or in text form.

User in 529 decides if SCPT has successfully locate the pain point A.

If not, in 530 User shall erase the original AA and remark AA, and return the process to 526, till in 529 User agrees that SCPT has locate the pain point correctly.

Once the pain point is located successfully by SCPT in 529, process moves to 531 where User indicates if AA is a point of treatment or not.

If yes, then in 535 the Clinician Software, along with the database 523 in FIG. 6B, shall prescribe a group of stimulation point X's to treat this pain point and the process then returns to 510 in FIG. 6B to locate X's.

If no, then in 532, with the database 523 in FIG. 6B, the Clinician Software shall indicate and display to User possible points of treatment or possible ailments or wellness regiments associated with the pain point AA.

In 533, User then may indicate what points of treatment or ailments or wellness regiments that may benefit the User. This process is based on that the User knows his or her body conditions and therefore may have a good idea what types of treatment points, ailments and wellness regiments that may be useful for him or for her. Clinician Software shall also contribute to the final conclusion in 533.

Clinician Software then confirms in 534, based on selected points of treatment, ailments and wellness regiments, a group of stimulation points X's.

And the process returns to 510 in FIG. 6B to locate X's.

Just like the process in FIG. 6B, our inventive process to convert pain points to points of stimulation may also be implemented by Augmented Reality (AR).

We will show one embodiment of how AR may be used in certain processes described above for FIG. 6C.

After 525, for AR based processing, the process moves to 539 wherein the User aims the camera of the Client device onto the body part including pain point AA.

In 540, the AR engine shall recognize that marked AA after all the AR imaging, pattern and object recognition and scaling processing and register AA in the database of a SBM.

The process then moves on to 531. As one may see, if all goes well, processes 526 to 530 in the image recognition based process described above may be simplified to processes 539 to 540.

Process 532, with AR, may be done with the User aiming the camera on the body parts containing suggested points of treatment where AR shall overlay those points X's on the body part and all the User has to do is to use a marker to make marks on those points of treatment the User is interested in, as done in process 533. Note that with AR, it is possible that the Clinician Software may already indicate, for example using a different colors, those points of treatment out of all the overlaid points of treatment the Clinician Software suggests, so when the User also select those points, then process 534 may also be completed.

AR may also be used in process 535 and the next processes 510 and on to streamline and speed up the process. For example, in 535, the User may aim the camera on body parts where AR has overlaid on those body parts suggested points of stimulation. With a marker, the User can then go through processes 510 and 535 to 537 to mark on his or her body each needed stimulation points.

Now that the Nurse App has guided the user to select the right type of carriers to use, and helped the user to locate where to place the carrier pair(s), our inventive method and system moves on to how the nurse app shall deliver the stimulation waveform dosage to the controller(s) to start the stimulation treatment.

Since a preferred embodiment of our inventive PSaaS service is built on using standard digital audio formats for all our digital stimulation waveform dosage, our stimulation controllers, in their simplest and easiest to use forms, shall work with the Client device just like a passive audio device, such as an ear set, a headset, a speaker set etc. An ear set or headset, for example, may need no built in source of power and controlling volume, skipping tracks, fast forwarding, and others may be done from a media player software inside the Client device. The audio device may be a simple slave device to the Client device (a smartphone, for example) and of the lowest possible cost to build and be afforded by a User.

While This type of open waveform format design makes it possible for us to offer, on the one hand, the lowest cost possible stimulation controllers every one can afford, and, on the other hand, add unrestricted flexibility in the digital stimulation waveform dosage to effect the best possible treatment outcome, it also creates the following limitations and challenges that require inventive methods and systems to solve them.

First, if a User bypasses our Client Software and intentionally uses a regular media player inside the Client device to playback, for example, a regular audio file to a stimulation controller to try to effect physical stimulation, we need to build in some methods to prevent this for safety considerations.

In most of our stimulation controllers where a digital microprocessor is used, this safety measure may be easily implemented using many commonly practiced digital and analog protocols. The challenge is for a passive/slave stimulation controller that contains no microprocessor.

One of the measures include a limiting circuit at the output stage of our stimulation controller.

Another inventive solution is that, while our digital stimulation waveform data conforms with the standard data format for, say, .mp3, .wav, .midi, .jpg, .mpg, .mov, etc, we may employ a file extension that is not the same as that used for these common digital music, picture, video or other productivity file format. For example, we may use .dps and:

A: When this file is played in a PC or any smartphones, pads, wearables, the OS shall not be able to play and need to find out what player is needed to play such a file. This may prevent, for example, for a data file with the .dps extension by a music player, for example, directly to an analog, digital or wireless ports bypassing our Client Software. Our Client Software will have to be used to deliver the digital stimulation waveform data file to compliant stimulation controllers. This is especially useful for our analog stimulation controller without a built in microprocessor.

B: Our stimulation controllers with a microprocessor will also deliver incoming digital stimulation waveform data to skin carriers by checking the data file extension first. This way, incompatible data file may not be accepted by our stimulation controllers to ensure the safety of our proposed PSaaS services.

Once someone is aware of this, a User may find a way to edit the file extension so it can be used without our Client Software regulating or managing it for stimulation safety consideration. So we may employ a dynamic and encrypted file extension method and system so that this file extension is dynamically changed and not constant at all times. There are off the shelf security tools we can use to implement this inventive methods and systems for our PSaaS service to ensure only the compliant digital stimulation waveform is used in the physical stimulation treatments and all physical stimulation treatment shall be conducted under the supervision of our Client Software to ensure the safety and efficacy of our treatment services under PsaaS.

Yet another inventive solution is to add, to our digital stimulation waveform, a unique ID sine waveform.

Please see FIGS. 3B to 3E for embodiments of the waveform formatting and the detection circuit inside a stimulation controller.

If we select the frequency of the ID sine wave to be, for example, 10.150 KHz, for most of our periodic stimulation waveform, the amplitude of the frequency component at 10.150 KHz is usually very low. The narrow-band band pass filter at 10.150 KHz will only let the frequency at 10.150 KHz pass and the rectifier will produce a DC voltage V accordingly, which is then used to turn on an analog switch at the output stage of the stimulation controller and stimulation waveform will be delivered to the connected skin Carriers. This analog switch may be a simple transistor that is turned on with a base to emitter bias above 0.6V, for example. This is just an example and there are other ways to implement an electronic analog switch.

The narrow band notch filter at 10.150 Khz, on the other hand, will remove this ID sine wave from the stimulation waveform and be delivered to the attached skin Carriers for stimulation treatment. The notch filter will also remove the 10.150 KHz frequency component from the original stimulation waveform, resulting in certain degree of distortion of the stimulation waveform. It is the reason why we will select the ID sine waveform at a frequency that is different from the discrete frequency components created by the period of a periodic stimulation waveform. For example, see FIG. 3D, if the period of the stimulation waveform is 10 msec, with a pulse width of 100 micro second, the frequency spectrum of this stimulation waveform includes frequency components at integer multiples of 100 Hz, and they are the highest at DC, and gradually decrease toward higher frequency components. Usually, as a rule of thumbs, for a pulse width of 100 micro seconds, the bandwidth of this pulse is defined as 10 KHz, and frequency components beyond 10 KHz are considered residues and cutting them off results in acceptable waveform distortion only.

Therefore, if we select the frequency of the ID sine waveform to be 10.150 Khz, you may see in FIG. 3D that the discrete frequency component of this ID sine waveform does not overlap with any frequency components of the normal digital stimulation waveform, so the 10.150 KHz notch filter will not affect any frequency components of the normal stimulation waveform, resulting in theory no distortion of the normal stimulation waveform. The 10.150 KHz narrow band band pass filter will also in theory will only let the ID waveform frequency component to pass and does not let any frequency components of the normal stimulation waveform to pass, so the rectifier after the 10.150 KHz narrow band bandpass filter will have a voltage exactly the same as the envelope value of the incoming 10.150 KHz ID sine waveform, which then may be used to reliably to turn on the analog switch at the outputs of the stimulation controller.

For medium frequency periodic waveform such as BMAC, IFC, the highest waveform medium carrier frequency used are less than 5 KHz, so selecting an ID waveform frequency as high as possible but within the overall bandwidth of the stimulation controller is probably a good design rule.

For rhythmed or completely randomized stimulation waveform, adding such an ID sine waveform will result in a small degree of distortion of the normal stimulation waveform due to the notch filer used and the rectified DC voltage level may vary slightly from the voltage level from the ID sine waveform, but as long as we select the frequency of this ID waveform as high as possible, both the distortion and DC voltage variation may be reduced to acceptable level.

Another inventive methods is to add ID sine waveform where there is no stimulation waveform in a periodic stimulation waveform, so the ID sine waveform does not appear when the stimulation waveform is active. In time domain, this is a viable approach to limit the ID sine waveform where there is not stimulation waveform for a periodic stimulation waveform. But signal processing in the frequency domain is a bit more complicated than an ever present ID sine waveform. A continuous sine waveform has one frequency component, while a periodic ID sine waveform will have multiple frequency components at integer multiples of the frequency of the periodic pulse train, making it harder to be separated from the frequency components of the normal stimulation waveform. More filtering circuits may be needed to remove as much as we can the ID sine waveform frequency components from those of the stimulation waveform.

If we decide not to adopt the ID sine waveform approach but still want to prevent a User from playing unauthorized audio waveform to effect a stimulation, then either a limiter or clipping analog circuit may be added before the stimulation output, so that the unauthorized stimulation will be at such a low level that it is completely safe.

Secondly, dominant operating systems are Microsoft Windows for PC and IOS and Android for smartphones and tablets. They all allow only one audio output at all times. That is, if our stimulation controller is active and connected to the Client device through the 3.5 mm analog audio jack, or through the lightning to 3.5 mm audio pack adapter for IOS Client device or through Bluetooth wirelessly, and there is an incoming call during the physical stimulation, either our Nurse Software has to temporarily suspend our stimulation in order for the User to take the call, or we have to build inventive solutions in our stimulation controller and in our Client Software so that the User may take the call and the stimulation needs not be suspended. These inventive solutions shall be explained in the detailed explanations below But one inventive design common to all our controllers is that, we will take advantage of the two channel stereo audio format supported by the audio subsystem of all the operating systems to provide either a two channel stimulation system, or to use one audio output for stimulation and the other audio output for playing back sensory waveform or for supporting concurrent incoming voice call during the stimulation. This inventive design is common to all our controller designs but methods of implementations may vary and will be explained below in each embodiment of the controller design.

Before we begin to explain in greater details controller embodiments C1, C2 and C3 in FIG. 1, these inventive methods and steps generally applicable to all these embodiments are explained here first.

This inventive method and system makes possible a cost effective two-channel physical stimulation via wires or via Bluetooth.

For example, we can use the same stereo audio device profile for BT to transmit two different or same stimulation waveform to the two channels in a stereo sound profile. That is, our Nurse Software, once it receives the stimulation waveform dosage for each carrier pair for a two channel stimulation, it will arrange one waveform dosage as audio signal for the left channel and one for the right channel and these two channels of waveform are send to the DAC in the smart phone to be converted to analog left and right channel audio signal, and through the audio jack, delivered to the connected stimulation controller type C1, or digitally through the data port delivered to controller type C2, or digitally though Bluetooth delivered wirelessly to the BT stimulation controller type C3.

Also note that in such a system design, our stimulation controller may also use the data layer for microphone in a audio device profile to transmit analog data such as the analog voltage measured from a serial resistor to the two polarities of our carrier, which when it is sent back via the emulated mic channel to our clinical office App, the App will send this analog waveform, like an analog audio waveform from a microphone, to the ADC (Analog to Digital Converter) to convert it into a digital data and the App can then use the digital data to effect various control or stimulation tasks, such as converting this digital data, based on the known resistor value, into current value of the physical stimulation at that moment to, for example, determine the skin resistance, or to monitor the stimulation current and decide if it is proper, too low (where there may be a need to adjust the stimulation voltage to boost the stimulation current) or too high (where the stimulation voltage may need to be lowered or stimulation may have to be stopped.)

We will begin to explain in greater details our inventive stimulation controllers C1, C2 and C3 shown in FIG. 1. Before we do so, we want to provide some useful information common to all our inventive controllers.

Figure 7:
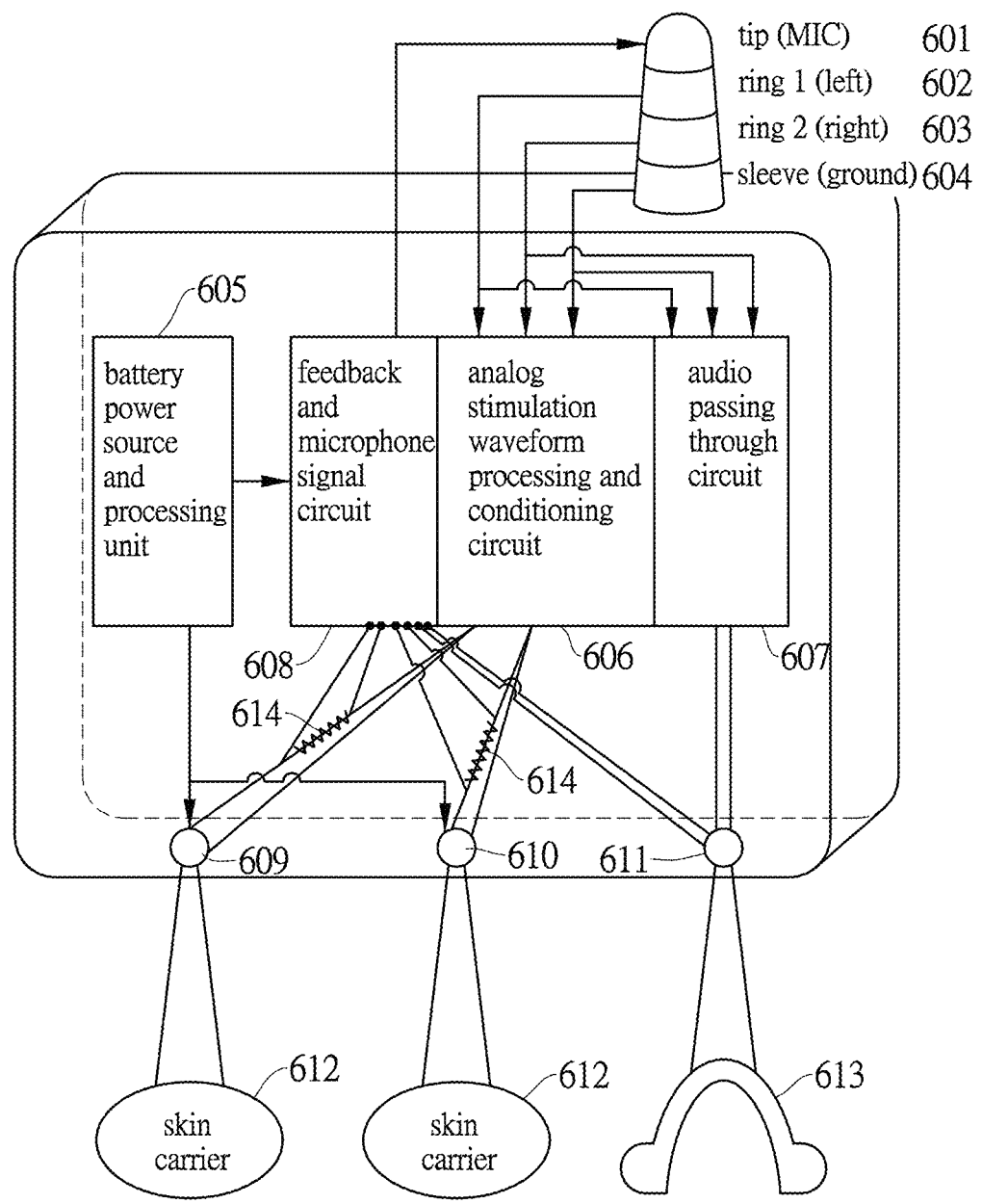
FIG. 7 shows an embodiment of a stimulation controller C1 connected to a Client device through an analog audio port.

FIG. 7 for Controller 1

In the past the controller for the stimulation is usually a portable or fixed electronic device with built in micro processor, digital signal processor and stimulation control and transmission circuit to deliver one of the stored stimulation waveform to the associated skin Carriers to conduct intended stimulation, be it electrical, magnetic, electromagnetic, laser, ultrasound, infrared heat and others.

In our inventive system, the inventive controller has a very different design framework than the traditional one. One of the embodiments shown as C1 in FIG. 1 is further described in FIG. 7.

In our inventive system, there will be no digital signal processor needed. Instead, the front end of the device is designed like an MP3 player to receive mp3 or similar digital music files, from connected wires, or from a connected port between a PC/smart phone/tablet and the stimulation controller or wireless from Bluetooth or Wifi or digital cellular channel such as 3G, 4G and future higher speed. The digital file is converted by an audio codec (encoder and decoder) to convert the digital information into analog electrical signal. For a regular music player, such a electrical signal is then processed and sent to speakers or a headset to convert such an electrical signal to audio or music waveform for listening or for conversation. But for our stimulation controller, the analog electrical signal is so processed that it is ready to be sent to stimulation skin Carriers applied on the body skin to create stimulation of the right intensity and for the right duration.

In its simplest form C1, the controller has a built in audio plug, such as as shown in an embodiment, 4 segment 3.5 mm audio plug used commonly in all multimedia devices from PC to smart phones to tablets to DVD players, etc (collected called Client in this article). The controller is plug into the Client device and the Client software in the Client device will, direct the prescription waveform dosage in the proper file format to a resident media player or to a specialized media player inside the Client Software, which in turn converts the waveform dosage into analog electrical signal and send it to the audio plug. It is received by the stimulation waveform processing and conditioning circuits 606, and the output waveform from 606 is sent to the carriers 612 that are attached to the skin and start the stimulation. Users can use the Client Software of the Client device to adjust intensity, duration of treatment and any other treatment parameters that users may have access to.

Recently, the newest iPhone 7 has eliminated the standard analog audio jack and use the wireless bluetooth to play back music but also is bundled with a lighting port to 3.5 mm audio jack adapter so Users can continue to use their current 3.5 mm audio jack based audio devices. Our C1 type analog port based controller, therefore, may be connected to an Apple Lightning port to 3.5 mm audio jack adapter. The adapter adds additional cost and the Client Software of the said. Client device needs to be written to work with the added communication layer of the adapter. Otherwise, stimulation controller C1 shall work in the same way as described above.

605 is the source of power and it usually is a battery pack. Please note that, in the simplest form of C1, it is possible that 605 and 606 may not be needed, just like a headset used for PCs, smartphones, tablets, etc. The output voltage from the common audio jack, be it 3.5 mm or 2.5 mm, is low, enough to drive the coil in the earpiece to create sufficient audio level for in-ear, on-ear or over-the-ear ear pieces. This is probably not enough to generate stimulation current level exceeding, say 1 mA, for 1K Ohm skin Carrier pair for, for example, a TENS type electrical stimulation. But for certain percutaneous skin Carrier (see examples in FIGS. 10A-10C, 11A-11D and 15A-15D) where the electrodes are very close to each other and skin impedance is sufficient low, or if the planned stimulation is a MENS type of microcurrent low level electrical stimulation, then with our audio file based waveform architecture, it is possible, that, it is the first time a User may try certain physical stimulation without the need to download an App software in their Client device, and without the need for a stimulation controller. All they need is a skin Carrier set.

We will describe an embodiment below using a 3.5 mm audio plug.

7.1. Connect the skin Carrier with a 3.5 mm audio plug to the 3.5 mm audio port on the Client device, 7.2. Go to the music store such as iTune, Google Music or others, or our website, and download compatible digital stimulation waveform in .mp3. .wav, etc.

7.3. Apply the skin Carriers to the body, 7.4. Use the built in generic music player software in the Client device to play the digital stimulation files of 7.2.

7.5. User may use the music player to start/stop, adjust the intensity of, fast forward, fast rewind, loop playback, the digital stimulation waveform, or, control these functions from the stimulation Carrier set, if the specialized skin Carrier also include control buttons, such as those found in premium headsets/earphones, to effect the above control functions.

This inventive system shall encourage the usage of physical stimulation as it is not only easy to use but cost very little to try, showing the benefits of our inventive system.

Also shown in FIG. 7 is 607 where the standard audio waveform not for the physical stimulation may be passed directly to an output port 611 on C1. This allows the User to connect their regular headset to C1 to listen to the audio or for phone calls.

Please note that there are several ways to connect the two input segments on the audio plug and one output segment on the audio plug Case 1:

For example, shown in FIG. 7 input segments 602 and 603 are connected to 606 and 607. The output segment 601 is connected to 608. This arrangement will allow EITHER two independent channel physical stimulation using stimulation waveform from 602 and 603, with any feedback analog signal from the stimulation session and control signal to be sent from 601 to the Client device ADC, OR stereo audio signal pass through using audio waveform from 602 and 603, with analog signal from mic in the headset plus control signal sent from 601 to the Client device ADC, but not at the same time for both.

Case 2:

If, for example, 602 is connected to 606 only and 603 is connected to 607 only and 601 is still connected to one 608, this arrangement is then to support BOTH one channel stimulation with feedback signal from the stimulation and control signal AND mono audio signal pass through with MIC and support control. That is, for example, the User may take an incoming call without suspending or stopping the physical stimulation. The User may also listen to audio as sensory stimulation when the physical stimulation is under way.

In our embodiment we designate 604 (sleeve segment) as ground. This is for illustrative purposes and actual assignments of the four segments (Tip 601, Ring 1 602, ring 2 603 and sleeve 604) in a real product shall comply with the prevailing standard for the audio port to ensure compatibility of the stimulation controller C1 with the general and our special Software of the Client device.

Please also note that the embodiment shown in FIG. 7 is a design without a microprocessor. It is the simplest design possible and also cost the least. However, for safety and function considerations, there may be a need to add a digital microprocessor into the Stimulation controller C1.

A1:

For example, we have described a method above adding an ID sine waveform to our digital stimulation waveform in order for C1 to prevent a User use a regular audio file to effect physical stimulation. With a digital microprocessor, other methods to prevent this is possible too. For example, an inventive method may be as follows:

Once a stimulation waveform is received at 602 and/or 603, the microprocessor may send, using a built in DAC and through 601, an analog command string to our Client Software.

Our Client software polls the MIC input digital port and analyze the command string, and since our Client Software did not send the said waveform, it will send a short command string in, for example, .wav file to the 3.5 mm audio port and it will arrive at the Controller C1 in analog waveform.

The microprocessor receives the said analog waveform, and use the internal ADC to convert it into the command strings. The command string indicates the said waveform did not come from our Client Software, so the microprocessor turns off the stimulation output.

Another implementation using a built in microprocessor inside C1 to prevent a User to use a regular audio file to effect physical stimulation is as follows:

We will add a unique digital preamble data to our digital stimulation waveform file.

The microprocessor shall use the internal ADC to convert the beginning segment of an arriving stimulation analog waveform and match that segment with the preamble data format.

If there is no match, the arriving stimulation waveform is considered unauthorized and the stimulation output shall be turned off to prevent the stimulation from happening.

B1:

Also as stated in Case 1 above, when an incoming call comes in and the physical stimulation has to be suspended, with a microprocessor, the following is possible so the physical stimulation may continue when the User is taking the call:

solution 1:

The microprocessor shall use its internal ADC to convert a frame or a segment of the stimulation waveform back into digital waveform format and store them in a nonvolatile memory inside or outside of the microprocessor.

When the call comes in and the User decides to take the call, the microprocessor will direct the input from 602 and 603 to the pass through sections 607 and 613, and use the internal DAC to convert the stored digital stimulation waveform into analog stimulation waveform and send them to 606 to continue the physical stimulation. The microprocessor will repeat the same stimulation waveform frame/segment till the User hangs up the call.

Then the microprocessor shall wait for the stimulation waveform to come from our Client Software, and resume the stimulation using the waveform again.

Solution 2:

Also note that, for periodic stimulation waveform, as we stated above in detailed descriptions for FIG. 3A, our PSaaS service shall use only the "Snippet" of the digital stimulation waveform. In this case, the Snippet of the digital stimulation waveform may be stored in the internal memory above so the stimulation waveform used during the phone call by the User shall be the same as those before and after the phone call.

614 shows a resistor connected serially at, for example, one polarity of the output to 609 and 610. It is used, on the one hand, as a current limiting resistor in case of a short circuit between the two polarities of a skin Carrier. It is also used in our inventive method to measure the skin resistance between the two polarities of a skin Carrier, which is further explained in FIGS. 15A-15D.

Figure 8:
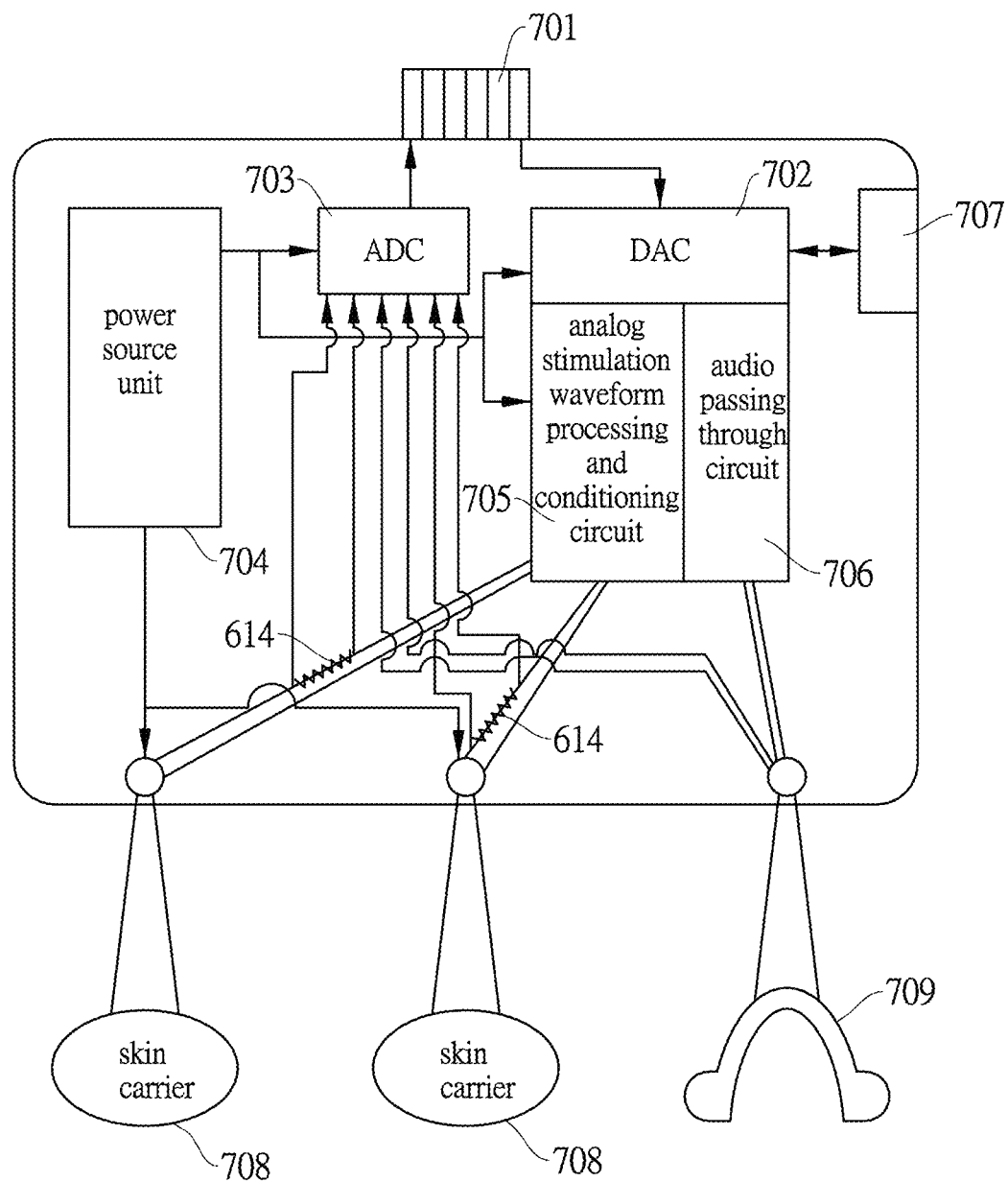
FIG. 8 shows an embodiment of a stimulation controller C2 connected to a Client device through a digital data port.

FIG. 8 for C2 digital port controller

The most commonly used digital ports today are USB ports for PCs, micro USB ports for all Android based smartphones, tablets and wearables, and Lightning port for Apple smartphones, tablets and wearables.

FIG. 8 show an embodiment of a digital port stimulation controller shown as C2 in FIG. 1.

Compared to C1, since the port 701 is digital and not analog, there is a need for a built in microprocessor including DAC 702 and ADC 703. Power source unit 704 may be optional, as usually ample 5V power is available from the digital port 701. The added source of power, however, may lessen the power drain of the Client device.

706 shall be similar to 607 in C 1, and 705 shall be similar to 606 in C1.

707 is either an internal nonvolatile memory, or can be a memory card slot to accept external memory cards such as SD, microSD cards and others.

Since the port is digital, supporting the basic requirements stated above for safety and function considerations preventing a User to use unauthorized digital stimulation waveform to effect stimulation, concurrent call taking and physical stimulation and concurrent audio sensory waveform playback and physical stimulation, based on various inventive methods and systems we discussed above, may be accomplished.

Also note that, except for iPhone 7 and future smartphones from Apple wherein there is no longer a 3.5 mm audio jack, our C2 controller may not be detected as an audio device and therefore, if a phone call comes in during the stimulation, the User may use the internal speaker and mic in the Client device, may use the headset connected to a 3.5 mm audio jack, or use a Bluetooth headset to take the call and the stimulation effected by controller C2 will not be affected.

For iPhone 7 and future smartphones, tablets or wearables wherein there is no longer a 3.5 mm audio port, our Lightning port based controller C2 may not be treated as an audio device by the IOS operating system, even though we use common audio file formats for our digital stimulation waveform. Therefore, the User may use the internal speakers and microphones or a Bluetooth headset to take incoming or make outgoing calls and the stimulation effected by our controller C2 will not be affected. User also may not use the built in music or media player in the Client device to send the unauthorized digital audio file to the controller C2 for physical stimulation.

Due to the high data through out rate for these digital ports, this type of digital controller may support higher number of independent stimulation channels than the maximum 2 independent channels possible in controller C1 shown in FIG. 7. For example, certain Client device may support 5.1 channel surround sound compression software, so that, up to 6 channels of independent physical stimulation is possible with C2. Digital stimulation waveform for each stimulation channel shall be individually prescribed by the Host Clinician software, synthesized by the Host Pharmacy Software and then they will be combined and compressed using the compression software either at the Host or at the Client software. The microprocessor inside C2 shall include the corresponding decompression software to decompress the combined digital waveform back into up to 6 independent digital stimulation waveform, and they will be processed at 702 and 705 and then delivered to the skin Carriers 708.

Please also note that, a DAC is needed for the Client device to control the stimulation controller. If there will be two way communications between the Client Software and the controller, such as taking a voltage across a load resistance to measure the current through the carrier pair and try to feed that voltage information back to the Clinical office App to calculate the equivalent current, then a ADC is also needed, like the ADC that is needed for the analog mic input from the headset to be sent back digitally to the Client in order for the Host to send it to, for example, a remote personal making a phone call or VoIP call with the said Client user. The great thing is that the DAC and ADC pair used for voice and music applications by the Client is equally applicable for our two way stimulation controller too, simplifying the design and lowering the cost.

Figure 9:
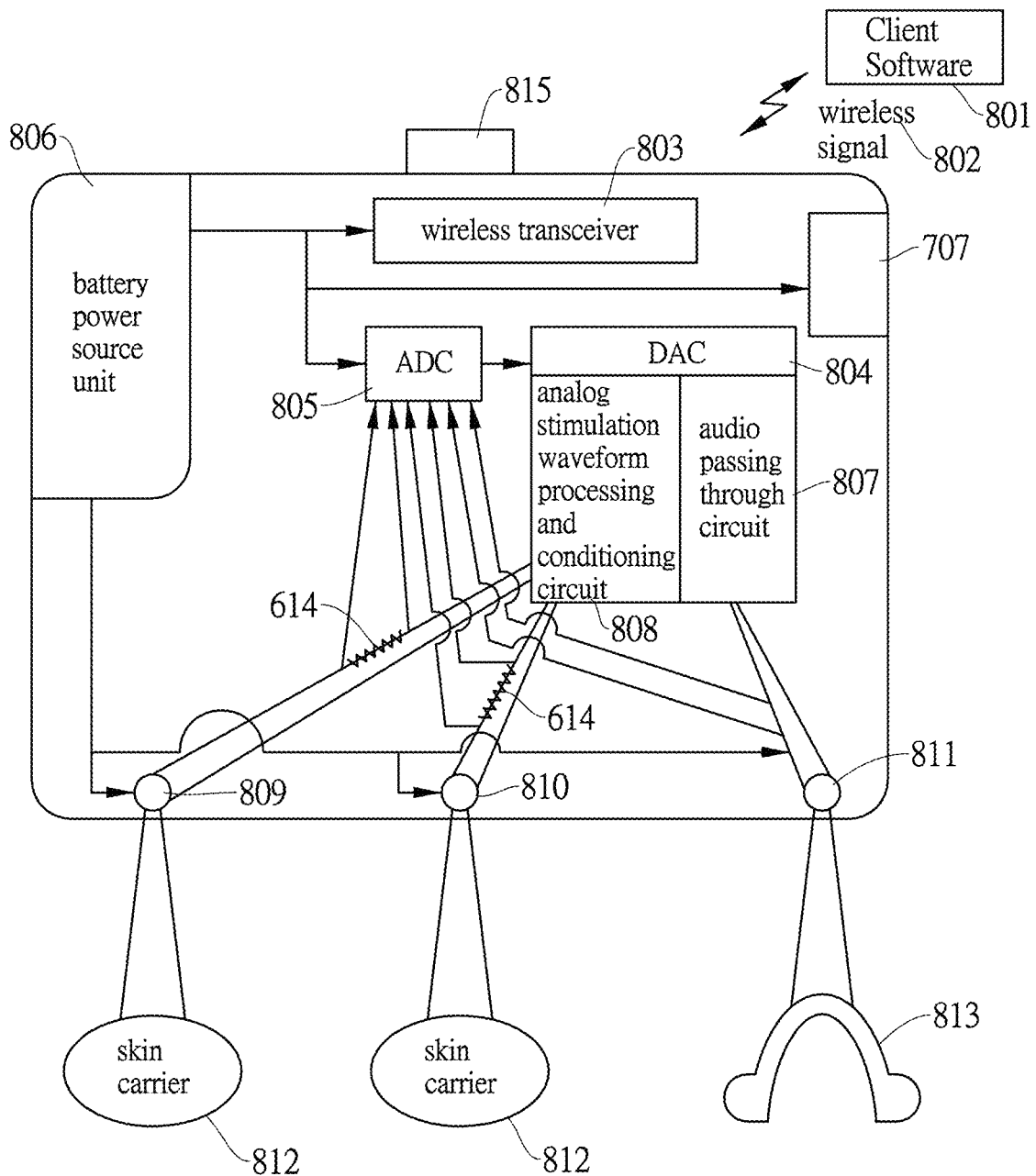
FIG. 9 shows an embodiment of a stimulation controller C3 with a wireless connection.

FIG. 9 for C3 wireless controllers

Although wireless connections include, in addition to Bluetooth, NEC (Near Field Communications), Cellular, satellite, and many proprietary cellular network used in places such as a hospital, a company or other places, Bluetooth and Bluetooth Low Energy continue to be the most widely used and most cost effective way to connect a smart phone to many consumer accessories such as keyboards, mice, headsets, speakers, vital sign monitors, fitness trackers, etc.

Usually a Bluetooth enabled health related devices, such as blood pressure monitoring, weight scale, heart rate tracking and others use Bluetooth Low Energy for low rate data communications and for command control. The volume of data, such as the weight number, or three blood pressure numbers, systolic, diastolic and heart rate data, are all very limited and fit well with the limited date rate of Bluetooth Low Energy.

In our application, for periodic stimulation waveform, only the Snippet of the digital stimulation waveform has to be sent one time from the Client Software 801 to the stimulation controller C3. Due to the relative small data file size of one Snippet, BILE may be sufficient. Once 803 received the Snippet, it will send it to the DAC 804 and from there it is sent to 808 for further processing and conditioning ready for the stimulation treatment. The microprocessor in C3 shall then repeat the Snippet playback during the entire stimulation treatment. This demonstrates how our inventive Snippet data format help to reduce data streaming requirements which lead to lower power consumption of the Client device and the controller C3.

For non periodic digital stimulation waveform, it will have to be streamed from the Client device to the stimulation controller throughout the stimulation session. Therefore, Bluetooth Low energy is not sufficient for this requirement and a regular Bluetooth transmission channel is needed. If the non periodic stimulation waveform is a rhythm driven non periodic stimulation waveform and SWC is used, then again this will result in lower volume of data to be sent, one time, from the Client device to the controller C2. Bluetooth Low Energy may be sufficient for this mode of stimulation resulting in again lower power consumption of both the Client device and the controller C3.

With SWC enabled digital stimulation waveform, the microprocessor inside the controller C3 shall assemble the continuous digital stimulation waveform based on the RRP FRAMES and DMT (see FIG. 3F) and stream them to DAC 804 and then to 807 for analog waveform processing and conditioning ready for physical stimulation.

Based on our waveform architecture, each C3 controller may support up to two independent stimulation channels, just like C1 and C2. C3 may be integrated with one set of skin Carriers so they can be applied on a body part away from the Client device. However, if C3 shall provide physical stimulation simultaneously to two independent sets of skin Carriers, then one set of skin Carriers has to be connected to controller C3 by wires.

Also note that if C3 uses Bluetooth audio device profile, it will be treated as an audio device and once it is paired with the Client device, all audio playback or voice call will go to C3, resulting in the same challenge C1 faces—(1) physical stimulation with unauthorized digital stimulation waveform prevention and (2) how to support concurrent physical stimulation and voice call/audio playing.

Solution for (1) will be similar to C1 with an added microprocessor (see A1 and B1 section for detailed description for controller C1.)

Another alternative for C3 not to use Bluetooth audio profile. This requires additional work with the Bluetooth standard setting association but it is technically feasible.

Please also note 815 dummy connector. This can be a dummy connector sized just like either lightning port or microUSB port or even a 3.5 mm audio plug, so when C3 is not used, it may be clicked onto the port of the Client device so it is not lost. The dummy connector may be made of plastic material so the Client device OS may not mistaken it as a valid connected functional device.

Several Embodiments of Inventive Carrier Designs

In part B of the prescription, just like a drug may be taken orally, by injection, through medical patches (such as nicotine patch), inhalation, intravenous injection, spray and others, the dosage of stimulation may be administered mainly invasively or non invasively to the body. For explanation purposes, we will use the non-invasive administration of the stimulation to describe our inventive systems and methods. The same principle shall be applicable to invasive physical stimulation treatments.

Once the dosage of stimulation waveform is determined by the Clinician Software of the Host and synthesized by the Pharmacy Software of the Host, the physical stimulation is completed by the Nurse Software of the Client device assisting the User to place the prescribed carrier(s) or multiple carriers on the prescribed areas of one's body and then delivering the dosage of the stimulation waveform to these Carriers to start the stimulation treatment Commonly used carriers range from the standard electro gel pads for transcutaneous skin electrical stimulation, to needles in acupuncture, to needles wired with electricity for percutaneous electrical stimulation, to braces or conductive clothing with built in skin stimulation objects to shoes or gloves with built in magnets to stimulate reflex points with magnetic fields and active pressure, and many others.

We have several inventive skin carrier devices and designs that may work well with our inventive digital stimulation waveform dosage to expand the options of the physical stimulation treatment and to make commonly used current physical stimulation treatment more effective than with the conventional skin carriers.

For commonly used transcutaneous or transcranial physical stimulation, wherein the stimulation waveform travels from one polarity of the skin carrier through the epidermal or dermal skin layer of the body or head skull to the other polarity of the skin carrier. For example, electrical gel pads used in all popular TENS, ENMS, BMAC and IFC electrical stimulation devices use a pair of reasonable sized electro gel pads for transcutaneous electrical stimulation between two large pads. Usually these pads are placed close to the area to be treated for pain, discomfort or muscle training so the current mesh created fully cover the area of pain. The pads usually are of a reasonably large size to reduce contact resistance between the pad and the body, and to allow the current mesh cover a broad area of the skin covering the area of pain or discomfort.

What we see as deficient in this type of carrier is that single purpose electropads for electrical stimulation misses the additive benefit of applying needed physical stimulation such as heat, cold, pressure/compression, etc on the point for treatment or throughout the area of the electrical current mesh. The physiological benefits of these additional physical stimulation may act to relax the muscle or regulate or stop any microscopic damage to blood veins or muscle or sensory nerve tissues, making the electrical stimulation more effective.

For invasive implant of electrical stimulation to stimulate nerves for disease treatment, the wire/lead has to be placed precisely on or over the target nerve segment. But for non invasive stimulation of vital points or nerve branches or nerve endings, electrical, magnetic, electromagnetic, laser, ultrasound, pressure or even Infrared heat stimulation all need to have stimulation waveform travel perpendicularly through epidermal layer into dermal and even deeper layer. Transcutaneous stimulation, instead, travels horizontally and transversely mainly on the epidermic and shallow dermal layer.

For example, acupuncture is a treatment modality commonly used and accepted nowadays by both eastern and western medical practices at least as an effective complimentary treatment modality. Its mechanism is not yet fully established but cumulative evidences of efficacy over the past many years have made it part of medical treatment modalities for many acute and chronic ailments. But needling is minimally invasive and needs to be done by certified clinicians due to risks involved. Therefore, there is a continued interest in replacing needles with percutaneous electrical, magnetic, electromagnetic, laser, ultrasound or pressure stimulation in order for the treatment be safely done by trained clinician assistant or at home by consumers. Relief Band, an FDA cleared class II device, is an example of such a successful consumer product. It stimulates, using a two closely spaced electrodes, percutaneously the acupuncture point (Acupoint) P6 located close to the wrist to treat nausea and motion sickness.

There is also an increasing interest in non invasively and percutaneously stimulating target nerve branch or nerve endings to treat certain ailment. A successful example is a product called Quell, which is strapped around the side of the calf of the lower leg so electrical stimulation may be directed at sciatic nerve to relief certain types of lower back pain.

We have invested for past many years in many novel stimulation carrier designs for nerves, muscle and vital points to treat disease or relief pain. These inventive carrier designs also work well with our inventive stimulation waveform dosage to expand the possible modalities of physical stimulation and to make current physical stimulation more effective than with current conventional skin carriers.

Figure 10A:
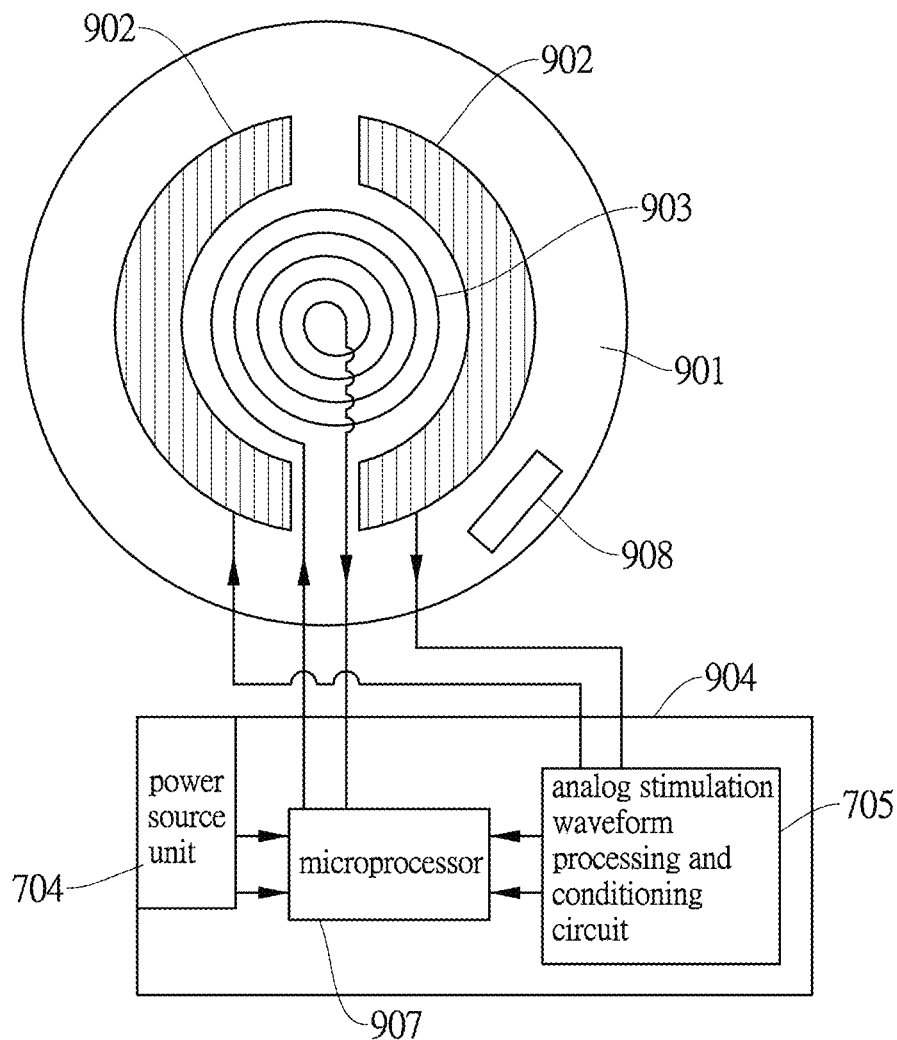
FIG. 10A shows an embodiment of a combinational skin carrier for electrical and magnetic stimulation.

Please see FIG. 10A for a carrier design embodiment that offer individual electrical or magnetic stimulation or both at the same time. Electricity and magnetism are inter-related and a carrier design to enable both stimulation treatment may bring added efficacy to stimulation treatments.

901 is a skin carrier substrate. 902 are a pair of electrical conductive areas and usually with conductive gel layer between them and the skin to conduct current and to affix the carrier to the skin. 903 is a conductive concentric electrical wire and with a DC or AC current it will generate a magnetic field whose polarity may vary depending on the direction of the current but always in the percutaneous direction.

904 is a stimulation controller and many be C1, C2 or C3 described in this patent application or other types. Just for explanation purposes, in this graph, we use 705 and 704 for controller type C2.

907 in 904 represents a microprocessor or a controller that may decide if a DC power source will be connected to 903 to generate a constant stimulating magnetic field of given strength and polarity, 705 will be connected to 903 to generate an alternating stimulating magnetic field with the field strength and polarities varying with the stimulation waveform.

This inventive carrier design may be useful for percutaneous stimulation application, if the size of substrate is small, but by changing independently the size of the pair 902 relative to the size of 903, it may be used to provide both transcutaneous electrical and percutaneous magnetic stimulation.

Also note that 908 represent a tag on the carrier substrate that can be an NFC (Near Field Communication) tag, can be a printed serial number or a printed barcode label or a QR code. This way there is an easy way for the User to provide or for the Tool Software module in the Client Software to identify the skin carrier type to ensure safe and effective physical treatment. Please see further explanations for FIG. 6A.

Figure 10B:
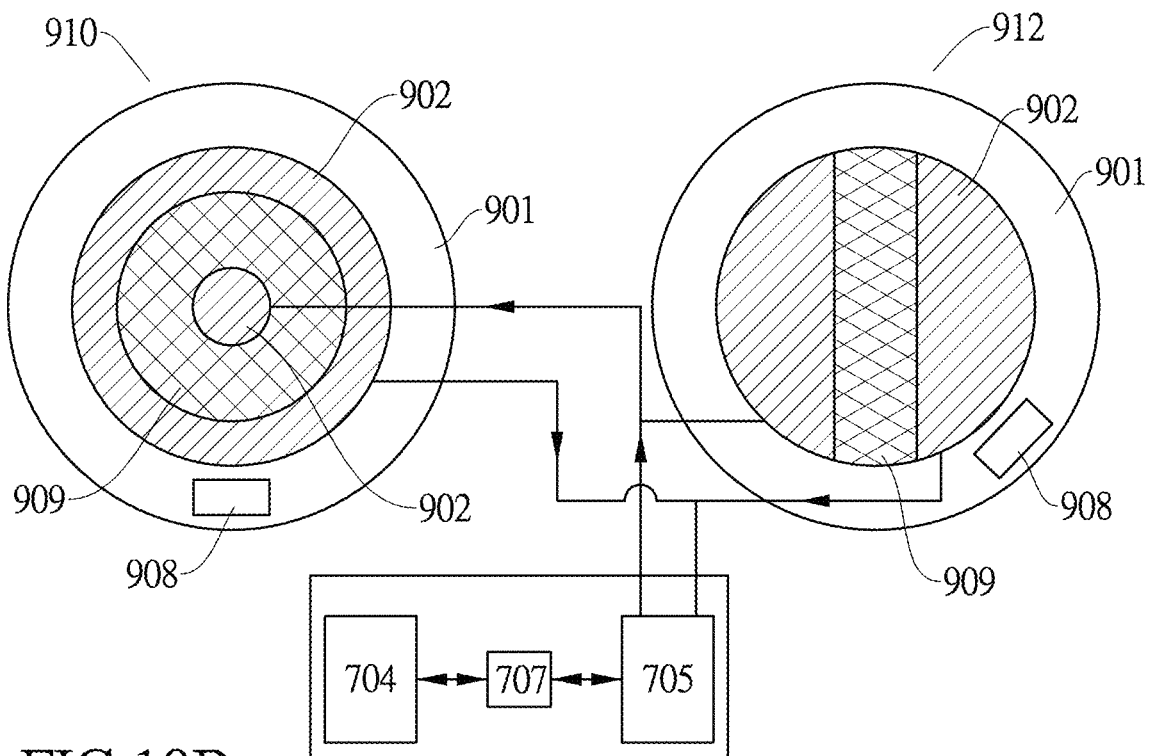
FIG. 10B shows two embodiments of combinational skin carriers for electrical and heat stimulation.
Figure 10C:
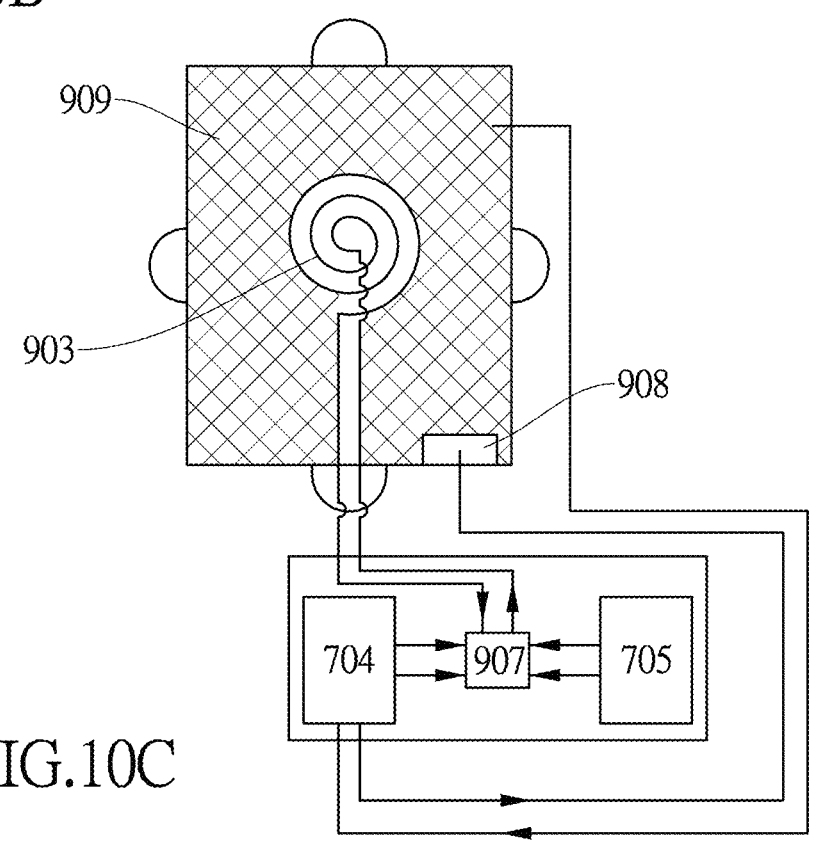
FIG. 10C shows an embodiment of a combinational skin carrier for magnetic and heat stimulation.

FIGS. 10B and 10C show the embodiments of another inventive skin carrier designs. Except for those not shown in FIG. 10A, we use the same denotation as in FIG. 10A for consistent and simple explanations.

FIG. 10B shows a skin carrier 910 for a combined electrical and heat stimulation. 909 is an area covered by material that may be heated via a proper source of power such as 704. For example, carbon fiber may generate infrared heat with a 5V DC power. Wherein the electrically conductive region is electrically stimulated to 902, and electrical stimulation of 902 from the electrically conductive region can be a primary physical stimulus and can be complementary to the thermal stimulus of 909.

FIG. 10B shows a skin carrier 912 for a combined electrical and heat stimulation. For the skin carrier 912, heat may be the primary percutaneous physical stimulation and can be complementary to the electrical stimulation of 902 from the electrically conductive region.

FIG. 10C shows a combinational skin carrier with a percutaneous magnetic stimulation carrier with the conductive concentric electrical wire 903 and a skin carrier with the heat stimulation pad 909 surrounding 903. This heat stimulation may come from the carbon fiber material mentioned above for 10B, as it may be heated with only DC 5V voltage source and the heat is infrared type of heat which may be very effective for deep and therapeutic skin stimulation.

Figure 11A:
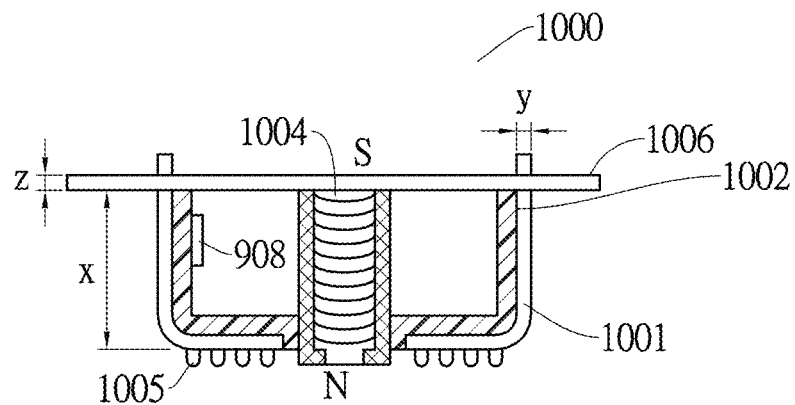
FIG. 11A shows a side view of an embodiment of a combinational skin carrier for percutaneous electrical, magnetic and heat stimulation

FIG. 11A shows another embodiment of an inventive skin carrier design.

FIG. 11A shows a side view of this carrier 1000. 1001 is an outer conductive hollow structure with certain height X and a wall of a certain thickness Y. It is conductive so it can be certain conductive metal such as copper or gold or silver, can be a metal coated with conductive metal such as gold, silver or copper, etc, or it may be made of a conductive rubber. On the top there is an opening so a fastening strap, tape, Velcro tape 1006 etc may go through and is tied tightly in order to securely affix the carrier to the body and to apply a proper level of pressure as part of the physical stimulation. On the bottom of 1001 is an opening so the element 1004 may fit through and contact the skin as 1004 shall form another polarity of the 1001 for electrical stimulation. On the bottom of 1001 one will find dimple points or small bumps 1005 and their purpose is:

to allow the current to reach certain body parts such as the head scalp area with a lot of hair and/or to allow the pressure to be more effectively applied on the body parts. A gel layer may be applied on the bottom of 1001, with or without 1005, so this carrier may be affixed to the skin without the strap. The only downside is the loss of the pressure stimulation but the rest physical stimulation is not affected.

An insulating layer 1002 shaped just like 1001 with certain wall thickness and height is placed and tightly fit with 1001, so the element 1004 and the hollow structure 1001 are insulated from each other.

1004 may be a conductively coated soft magnetic material with insulated electrical wires coiled on it and wrapped optionally with a heating fabric such as a carbon fiber layer. So not only 1004 is the polarity and if the electrical wire is powered by a DC or AC power source, it can also generate a percutaneous magnetic field.

The purpose of this inventive general purpose carrier design came from our needs to affix skin carriers to places such as the scalp with a full head of hair, or for a skin carrier that may emulate acupressure or reflex pressure treatments. The strap for a single carrier like this may be replaced with, for example, a brace, inflatable cuff, a cap, a sock, a glove or others with multiple carriers like this built in, so the carriers stay closely contacted with the skin while delivering all of or portion of pressure, electrical, magnetic and heat stimulation at one time.

Figures 11B, 11C:
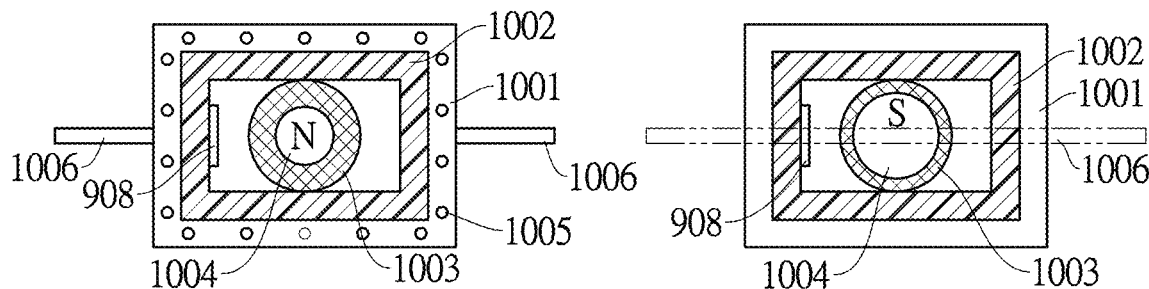
FIG. 11B is a bottom view of the combinational skin carrier in FIG. 11A.
FIG. 11C is a top view of the combinational skin carrier in FIG. 11A.

FIG. 11B shows a bottom view of this carrier design.

FIG. 11C shows a top view of this carrier design.

Figure 11D:
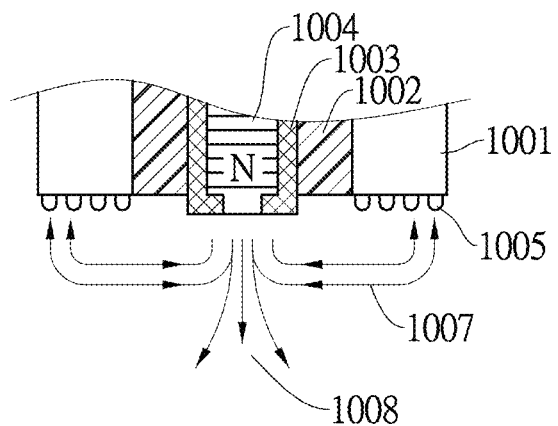
FIG. 11D shows the current and magnetic field flow and polarity of the combined skin carrier in FIG. 11A and how heat is applied to the body.

FIG. 11D shows how the flow of electrical current 1007 and the flow and polarity of the magnetic field 1008 and how local heat may be applied to the point of stimulation on the body.

Figure 12:
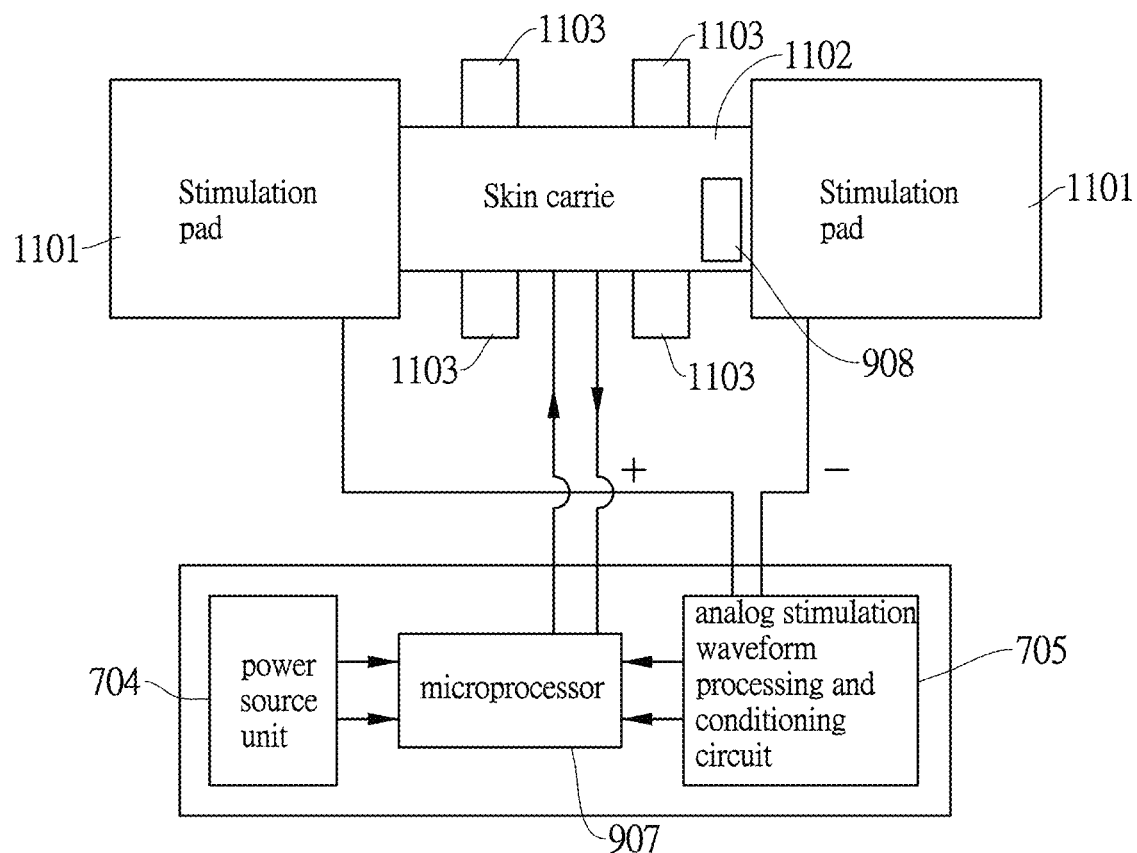
FIG. 12 shows another embodiment of a combinational skin carrier.

FIG. 12 shows an embodiment of another inventive carrier design.

We came up with the design due to the needs not only to provide transcutaneous physical stimulation, but to add percutaneous stimulation near the point of pain or discomfort to speed up the effect of the stimulation treatment.

1101 may be conventional stimulation pad pair such as a pair of electro-pads for transcutaneous stimulation.

Added between 1101 is a section 1102 that may be powered heat or magnetic or multiple pressure type carriers as shown in FIG. 11A, to effect local and possible percutaneous stimulation near or at the point of pain or discomfort. This added stimulation near or at the point of pain or discomfort has shown in our internal trials to improve the treatment efficacy, or non powered heat or cold stimulation such as a cold or heat pack. For example, there are chemical based hand warmer packs of various sizes that can provide effective and instant heat. Likewise for instant cold packs of various sizes. Carrier design such as shown in FIG. 11A may be used without any powered electrical, magnetic or heat elements but just its ability to exert some proper mechanical pressure at or near point of pain or discomfort.

1103 are pads that use gel material to affix 1102 securely to the body.

FIG. 13A to 13D show another inventive skin carrier design and show an embodiment of a carrier set using multiple carriers which are similar to but modified from the carrier disclosed in FIG. 11A. For illustration purposes, we use a head carrier set as an example. This is also a carrier set we designed and used in our internal clinical study of physical stimulation of the head scalp to treat sleep disorder.

Figure 13A:
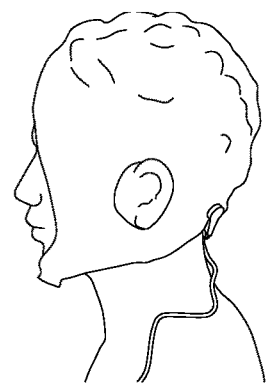
FIG. 13A shows a scalp skin carrier set wrapped over the scalp.

FIG. 13A shows how this carrier set was securely wrapped around the whole head scalp.

Figure 13B:
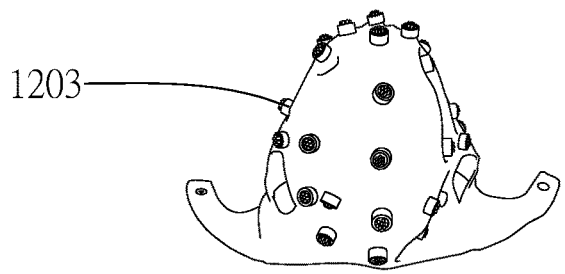
FIG. 13B shows a scalp skin carrier set with many independent carriers inside.

FIG. 13B shows the inside of this carrier set how the multiple individual stimulation carriers 1203 are distributed and connected. Each individual carrier 1203 is expanded and shown in FIG. 13C with its side view.

The skin carrier 1203 is very similar to the overall carrier 1000 described in FIG. 11A, but 1203 is a single polarity carrier, not like 1000 which is a dual polarity carrier. Therefore, a pair of 1203 need to be used together to form, for example for electrical stimulation, a current path.

Figure 13C:
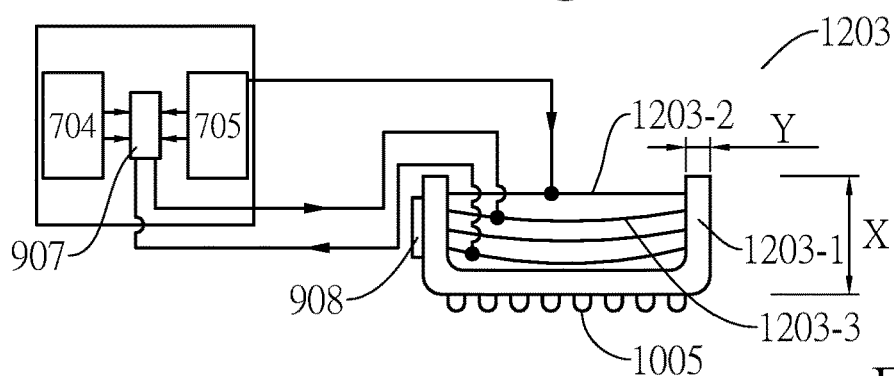
FIG. 13C shows an enlarged side view of a separate carrier.

1203-1 in FIG. 13C is an outer conductive hollow structure with certain height X and a wall of a certain thickness Y. It is conductive so it can be made of a conductive metal such as copper or gold or silver, can be a metal coated with conductive metal such as gold, silver or copper, etc, or it may be made of a conductive rubber. On the top there can be an optional opening (Not shown in FIG. 13C) so a fastening strap, tape, Velcro tape etc may go through and is tied tightly in order to securely affix the carrier to the body and to apply a proper level of pressure as part of the physical stimulation. On the bottom of 1203-1 one will find dimple points or small bumps 1005 and their purpose is to allow the current to reach certain body parts such as the head scalp area with a lot of hair and/or to allow the pressure to be more effectively applied on the body parts. A gel layer may be applied on the bottom of 1203-1, with or without 1005, so this carrier may be affixed to the skin without the strap. The only downside is the loss of the pressure stimulation but the rest physical stimulation is not affected.

1203-2 may be a conductively coated permanent magnet tightly fit inside and in contact with 1203-1, or 1203-2 may be a conductively coated soft magnetic material with insulated electrical wires 1203-3 coiled/wrapped on 1203-2 but the bottom of 1203-2 needs to be contacting closely 1203-1.

This inventive carrier arrangement effects both 1203-1 and 1203-2 to form together an efficient conductor for electrical stimulation, and 1203-3 may generate, at the same time, percutaneous magnetic field of constant polarity or alternating polarity. Since 1203-1 is just one polarity of a pair of the same type of carriers, it is connected to one polarity of the controller module 705. But 1203-3 shall be connected to 907 fully to receive either DC power from 704 or alternating power from 705 to generate constant or alternating magnetic field.

Figure 13D:
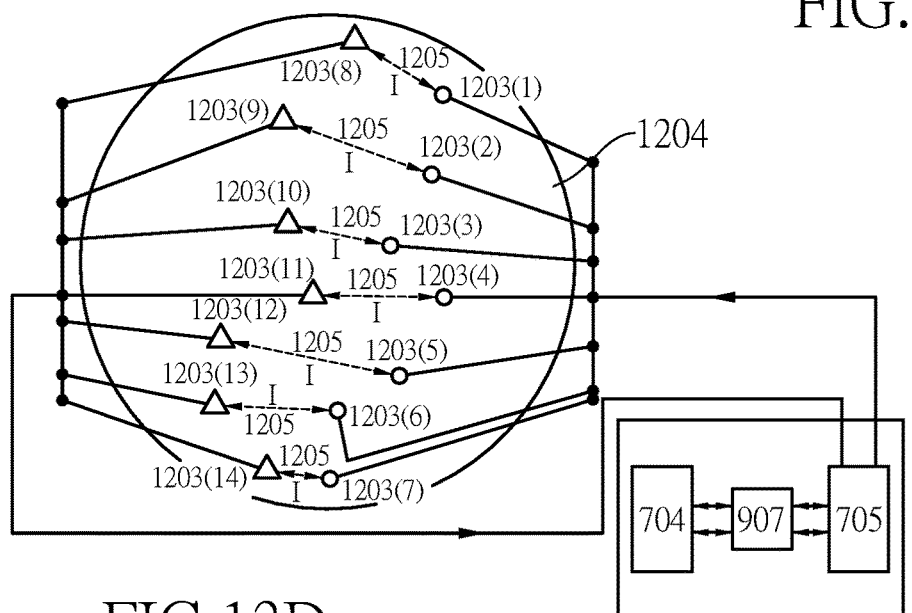
FIG. 13D shows an embodiment of a scalp skin carrier set for electrical and magnetic stimulation.

Shown in FIG. 13D is an embodiment of a full carrier set using fourteen 1203 carriers with seven carriers connected to one output polarity of 705 and seven carriers connected to the other output polarity of 705. 1203-2 shown in this embodiment is a coated permanent magnet each generating independently a constant fixed polarity percutaneous magnetic field.

Primary transcranial current mesh is shown as 1205. The main transcranial current usually flows from one polarity to the other polarity with the lowest resistance/impedance between these two carriers. So this carrier set will be able to provide a broad transcranial current mesh and percutaneous (or percranial) magnetic field stimulation.

This carrier design is very inventive as it successfully integrate percutaneous magnetic field into an electrical transcutaneous or transcranial carrier sets. It may lead to many effective physical stimulation modalities for body parts rich in nerve endings, acupuncture points and reflex zones so a more comprehensive multi-point electrical, magnetic and pressure physical stimulation may be effected.

Figure 14:
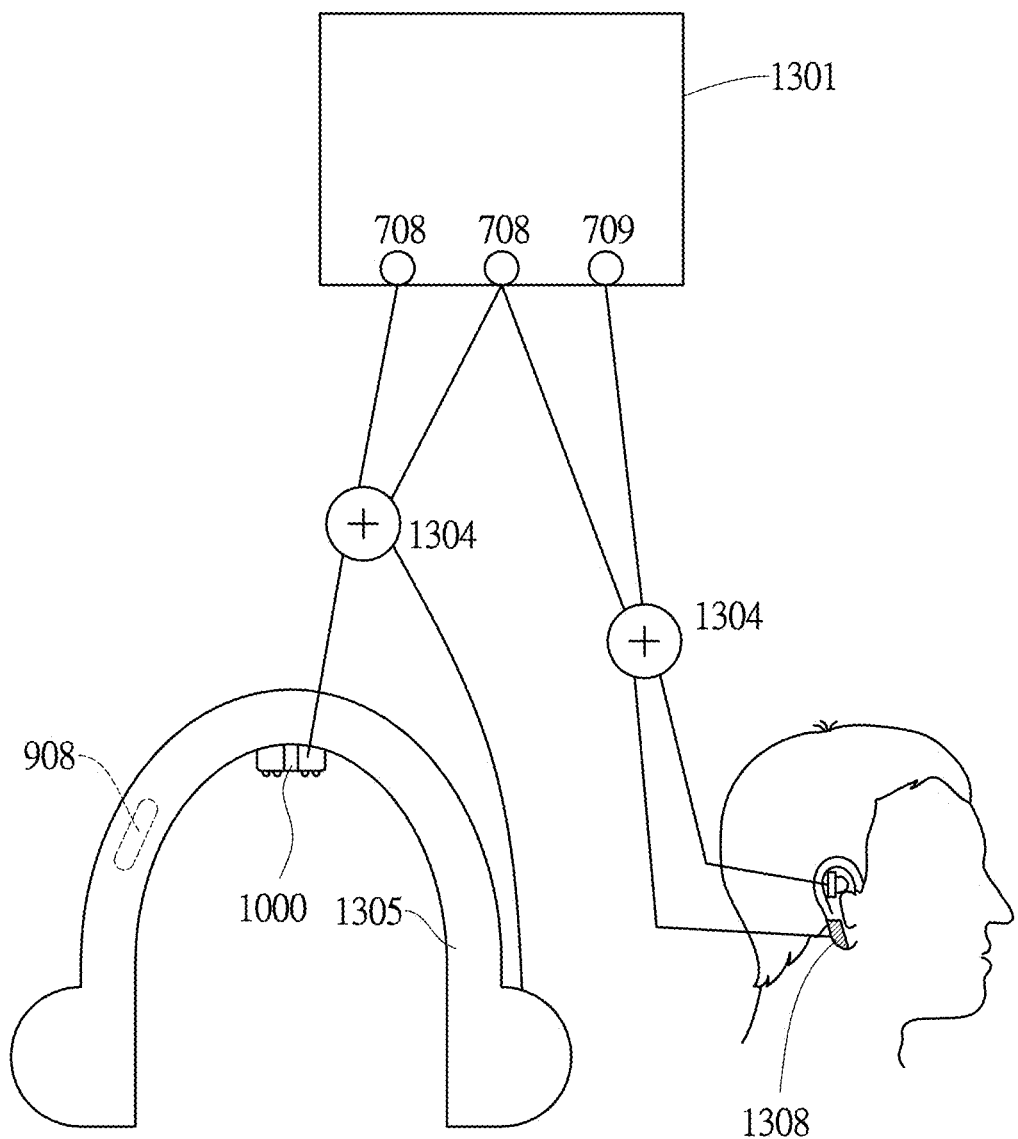
FIG. 14 shows an embodiment of a combinational skin carrier for physical stimulation and sensory stimulation.

FIG. 14 shows an embodiment of a physical stimulation carrier that include a concurrent audio sensory stimulation. Stimulation controller 1301 in this example uses controller C2. Any stimulation controller may be used in its broad application.

As an example, a special stimulating headset 1305 is shown to include an integrated percutaneous stimulating carrier 1000 as shown in FIG. 14. Two pairs of wires are available from 1305 to connect 1305 to both physical stimulation output and regular audio output. If the User chooses not to connect the stimulation output, stimulation carrier 1000 can still provide a pressure stimulation along with the audio sensory stimulation. If 1000 may be made adjustable manually or electromechanically so it may be adjusted to apply the pressure to a useful stimulation point, be it an acupuncture point or a nerve ending, the effect will be even more pronounced. If the User chooses to connect carrier 1000 to a physical stimulation output, then the benefits of physical stimulation should increase too.

Shown in 1307 is another embodiment of an in-ear headset with an integrated carrier 1308, such as a simple ear clip or a small carrier such as those disclosed in our FIGS. 10A to 10C and FIGS. 11A to 11D, where a miniature carrier may be applied on one side of the earlobe, or as the one disclosed in FIG. 12 where a miniature one may be applied to both sides of the earlobe, etc. Also for someone with a hole for earrings, a carrier with a proper earring post like attachment design may be used to better secure the carrier for better skin contact While FIG. 14 uses controller C2 and carrier 1000 as an example, this overall inventive design is not limited to the examples used but broadly applicable to various stimulation skin carriers and controllers. For example, controller C1 may be built as part of 1305 and 1305 in plugged into a 3.5 mm audio jack of a Client device.

Please see FIG. 15A for how we propose inventive methods and systems in the stimulation controller and skin Carrier designs to make measuring skin resistance/impedance easier, which can provide the following benefits:

prior to stimulation, to determine the best place to apply the percutaneous skin carrier in order for maximum electrical current to flow into the skin layer to achieve best possible results;

during the treatment, to afford a periodic monitoring of stimulating current to make adjustment for both efficacy as well as safety.

1401 in FIG. 15A shows an embodiment of an electronic circuit inside a stimulation controller. It is a simple example of outputting a voltage which varies based on the skin resistance measured 1402. The output from 1401 is sent to the tip 601 for controller C1 (see FIG. 7), or to 1403, which is 703 for stimulation controller C2 (see FIG. 8) and 805 for stimulation controller C3 (see FIG. 9).

A pad pair connected to skin 1402 is connected in parallel to one 1405 resistor. When the skin carrier is not applied to the body, 1402 is an open circuit so the output voltage of 1401 is 2.5V. But if a skin carrier pair are applied to the body and, for example, if the skin resistance is, 1000 ohm, and 1405 is 1000 Ohm resistor, then the output voltage of 1401 becomes 1.77V, not 2.5V any more. This voltage will be converted to a digital number either by the internal ADC of the Client device if stimulation controller C1 is used, or by the internal ADC if stimulation controller C2 or C3 is used, and the Tool Software of the Client device will use the digital number to calculate the skin resistance as follows, $R_{total} = (V_{out} \ast Z)/(5 - 2 \ast V_{out})$ where Z is the resistance value of 1405 and Vout is the output voltage of 1401.

And $R_{skin} = R_{total} - (R_{carrier\ polarity\ 1} + R_{carrier\ polarity\ 2})$ Since Rcarrier polarity 1 and Rcarrier polarity 2 may be measured as part of the skin Carrier specifications, Rskin may thus be decided.

FIG. 15A is merely one embodiment of the circuit design and our inventive method is not limited to this particular embodiment.

FIG. 15B shows an embodiment of a skin carrier for skin resistance measurements. Use the same denotations as in FIG. 10A for ease of references, this is a basic skin carrier and connector 1407 may be a simple plug with two segments, tip and sleeve and may be plugged into any of our stimulation controllers.

For this simple skin electro-pad with dual polarities like a dot in the middle and an circular ring of a certain width and diameter, the total resistance Rtotal is Rinside+Routside+Rskin (wherein Rinside+Routside is the value of Rtotal measured when Rskin is zero) and if a User is to use this method to look for a stimulation point with a lower resistance than surrounding area of that stimulation point, the simplest way to do so is for the User to place the dual polarity pad on point 1, and the Tool software in the Client device shall determine and record Rskin-1. The user then move the skin carrier to 2-3 other places close to point 1 so Rskin-2, Rskin-3 and Rskin-4 are determined and recorded by the Tool Software. Then a comparison may be made by the Tool Software among 3-4 measurements or an average may be calculated. Based on these results, the Tool Software may work with the Imaging Software in the Tool Software to decide where the stimulation point with the proper resistance is for the Nurse Software to guide the User apply the skin Carrier accordingly. For an explanation of these additional steps, see detailed explanations for FIGS. 6B and 6C.

Additionally, as shown in FIGS. 15C and 15B, a set of three electro pad pairs in a big pad substrate 901, we may use a conventional 4 segment TRRS audio plug 1408 with one ground and three segments for each of the three pad pair positive input 902-1, 902-2 and 902-3. Commercially available off the shelf audio plugs offer the most a 5-segment TRRRS audio plug. Therefore, as an embodiment, shown in FIG. 15D, we can have 4 pad arrangement.

If skin carriers such as those shown in FIGS. 15C and 15D, are used, inside any stimulation controller, added connecting circuit may be designed and the microprocessor in that stimulation controller may connect, for example, the multiple electro-pad skin carrier in FIG. 15D. The controller may connect the test digital waveform to 902-1 pair first, measure and record Rskin-1, and then repeat the same for 902-2, 902-3 and 902-4 pairs. After that, the Tool software may decide where the stimulation point with the lowest resistance may be, based on an algorithm of decision making from the current measurement results and from the database of standard resistance values of past measurements or clinical results.

Figure 16A:
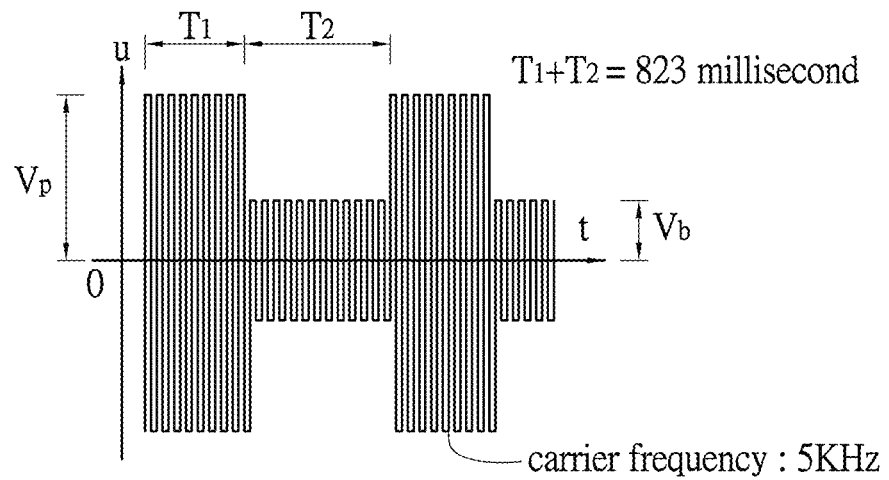
FIG. 16 A and FIG. 16 B shows an embodiment of an stimulation modality for treating low back pain using a unique stimulation waveform (FIG. 16 A) to stimulate points on foot holes (FIG. 16 B).

FIG. 16A shows an embodiment of an inventive stimulation treatment modality our PSaaS can support well Products such as TENS, ENMS uses baseband pulse trains to stimulate epidermal sensory nerves with appreciable yet tolerable intensity to relieve local pain. BMAC and IFC uses amplitude modulated medium carrier frequencies to train or reeducate muscles with as high intensity as tolerable to the user in order to obtain maximum effects on intended muscle exercises. They also were shown from user results and clinical studies to provide pain relief too, which is an indication allowed by FDA.

Using a low level amplitude modulated medium carrier frequency with based band pulse train of varying pulse widths and pulse frequencies, without the patient or user feeling the stimulation, to stimulate extremities of a body, including hands, foot soles and ears, where rich amount of sensory peripheral and major autonomous nerves, major muscle groups and reflex zones/vital points are found, in order to treat ailments, symptoms or pain in the body parts outside of the area covered by the current mesh generated by the pre arranged electrodes, is a technique that has not been practiced and found in current electro muscle and neural stimulation.

Acupuncture is a widely acceptable treatment modality that apply needles on vital acupuncture points to treat ailments, symptoms and pain in body parts or organs away from the points of needles. ACU-TENS are also practiced where base band TENS pulses replace the needles and are applied at the same vital acupuncture points. Waveform uses are baseband TENS type of stimulation waveform with appreciable intensities.

Acupressure works similarly to acupuncture and ACU-TENS but intensive pressure instead of needles or electrical signals are used.

Reflexology is another widely acceptable treatment modality with pressure or massage of reflex zones on foot soles, hands and ears to treat or relief ailments, symptoms, and pain. It is different from acupressure in that reflex zones are limited to foot soles, hands and ears while vital acupuncture points are found throughout the whole body.

Our investigations are centered on very low level stimulation of the whole or majority of extremities such as foot soles, hands and ears, without the stimulation felt by the patient or user, to effect pain relief outside of the extremities covered by the current mesh of the stimulation.

Our treatment modality is based on the following inventive treatment theorems:

physiologically, our composite stimulation waveform with medium carrier frequency goes deeper than epidermal layer and further into the dermal area and create the same effect as a deep massage type pressure on reflex zones and vital points used by acupressure, which then achieve treatment results for body parts or organs connected to the said extremity via muscle groups, nerve fibers, eastern meridian channels, reflex zones and even circulating blood vessels.

Additionally, low level electrical stimulation may have the following therapeutic effects:

if a user does not feel the stimulation or the muscle or nerve endings are minimally evoked, it means that brain command center is not aware of any external intrusion, is relaxed and the ambient electrical stimulation shall work compatibly with sensory nerves, any acupuncture points and muscle groups on that part of the body extremity that are connected to the pain point or point of discomfort, resulting in cellular level therapeutic effects to not only reduce pain but to provide certain degree of treatment. While TENS treatment may want to attract the attention of the brain to generate pain reducing agent such as Endorphins, we theorized that letting low level electrical stimulation work on cellular level without intervening brain with sensory nerves, muscle groups and possible acupuncture points to effect treatment results is a potential pain relief and symptom treatment for connected body parts or even internal organs.

Our invention physical stimulation modality, due to its low level of physical stimulation, is also safe and can be used by users for a longer period of time than high intensity TENS, ENMS, BMAC or IFC treatments. High intensity massage of reflex zones and acupressure vital points are extremely labor intensive and physically demanding and may not last if it is administered by a User himself or herself or by a third party helper.

So even though the BMAC waveform used is not new, but using it at such a low level on only extremities such as foot soles, hands and ears, so mentally the user is not aware of or minimally aware of, and is not distracted by the stimulation, in order to effect treatment results for ailments, symptoms and pain outside of the current mesh area covered by the pre-arranged electrodes, are new and not obvious to the practitioners in the present art.

After we developed our treatment theories, we conducted many in house pre clinical studies to verify our theory and to determine from a broad range of parameters the frequency for the carrier frequency and the pulse width and frequency of the modulating baseband waveform, for different target ailments, symptoms and pain. The main waveform group was found very effective is a 5 KHz medium frequency amplitude modulated by a 1.2 Hz square waveform with a varying pulse width and Vb in FIG. 16A may not be zero but with a small intensity which is a fraction of the full stimulation waveform amplitude Vp.

After these internal clinical studies to determine the carrier frequency, the pulse width, duty cycle and frequency of a baseband pulse train that amplitude modulates the medium carrier frequency, we decided to conduct a formal clinical trial in a major hospital in Taiwan to validate the our theorem.

Figure 16B:
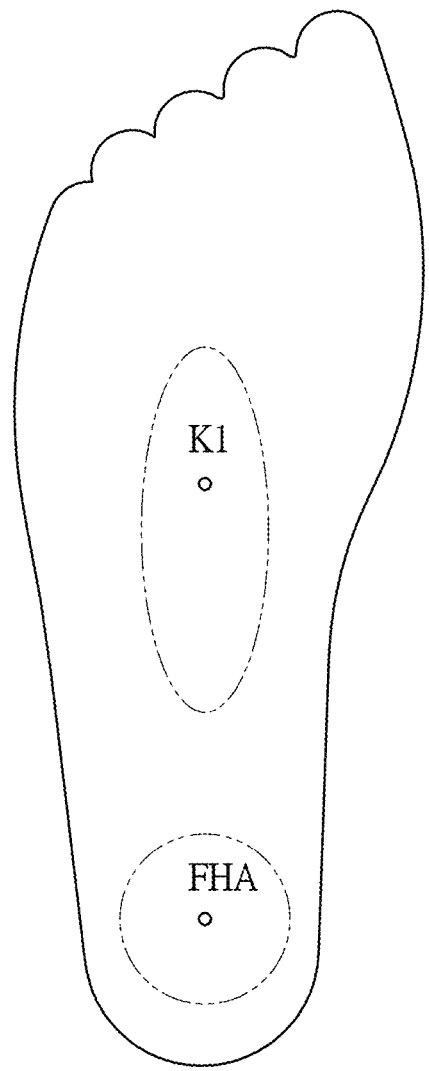

The waveform that finally was selected for the clinical trial was a 5 KHz carrier frequency modulated by a baseband pulse train of 1.2 Hz with pulse width T1 in FIG. 16A of 278 msec and Vb is 35% of Vp. Detailed waveform is shown in FIG. 16A. Placement of the skin carriers are shown in FIG. 16B.

The clinical study was a double blind study on 66 total study subjects, with 33 subjects receiving no actual stimulation (sham stimulation) and 33 subjects receiving actual stimulation of the above waveform with low enough intensity that each subject does not feel the stimulation (prior to each stimulation session, skin resistance of each subject was measured so the intensity of the stimulation may be determined during that session to ensure that the subject did not feel the stimulation, this on the one hand made the trial truly double blinded, and on the other hand, conformed to our clinical trial protocol that the stimulation shall not be felt by each subject (this is so designed so that the product from this clinical trial may be worn for a long period of time to effect safe yet useful stimulation to relief lower back pain). This is a treatment protocol that is inventive as all electrical stimulations use the intensity of stimulation that can be felt by and tolerated by the User under treatment. Additionally, two large electro-pads were applied onto the front and back of the foot sole (see FIG. 16B) to treat lower back pain far away from both feet. Therefore, the combination of a type BMAC waveform, not placed as in the current known art at or near the treatment point or area, but placed on the soles of both feet to treat lower back pain far away from the foot soles, and stimulation at the intensity not felt by the subject, are inventive and not obvious to practitioners skilled in this art.

The final results of the clinical trial showed clinically significant improvements over the Placebo subjects and the device won the approval of Taiwan Food and Drug Administration for the indication of pain relief of lower back pain.

During the full course of the clinical trial, the waveform and the whole protocol were not disclosed to any test subjects, any clinical assistants performing treatments on the test subjects, or any other third party or publicly Participating government reviewing committee, hospital clinical trial committee and lead investigator physicians and the CRO (clinical Research Organization) hired to organize the full clinical trial all signed non disclosure agreement. Test subjects were not informed of the waveform used and all the treatments were done by clinical assistants in a hospital so the waveform information and the whole clinical trial protocol remained confidential and were not available publicly. After the completion of the clinical trial, no commercial device has been made or marketed as we want to file the patent application first before marketing of the product based on this clinical trial protocol starts.

We also want to demonstrate how our PSaaS service shall be used successfully to provide Users this stimulation modality.

If the Clinician Software on the Host server prescribed this treatment modality, Pharmacy Software shall synthesize the basic stimulation waveform per FIG. 16A, and may use our SWC module to add any rhythm driven random stimulation to effect better stimulation results and to effect reducing adaptation and fatigue.

Nurse Software shall access the Tool Software to use the proper skin carrier, such as those from FIGS. 15A to 15D, to measure and record the skin resistance of the User.

Based on the personal information of the User, the proper intensity of the stimulation shall be set, because for this treatment modality, the stimulation level shall be so set that it is not felt or minimally felt by the User. User may make only limited intensity adjustment in order to comply with the intensity and duration of this treatment modality. For example, we discovered from a lot of past experiences, from example, a User with long term diabetes, or an old aged User, may have trouble sensing the stimulation, resulting in potential skin burning without the User being aware of it, if we let the User adjust the intensity as long as it is "tolerable" to him or her.

Figure 17:
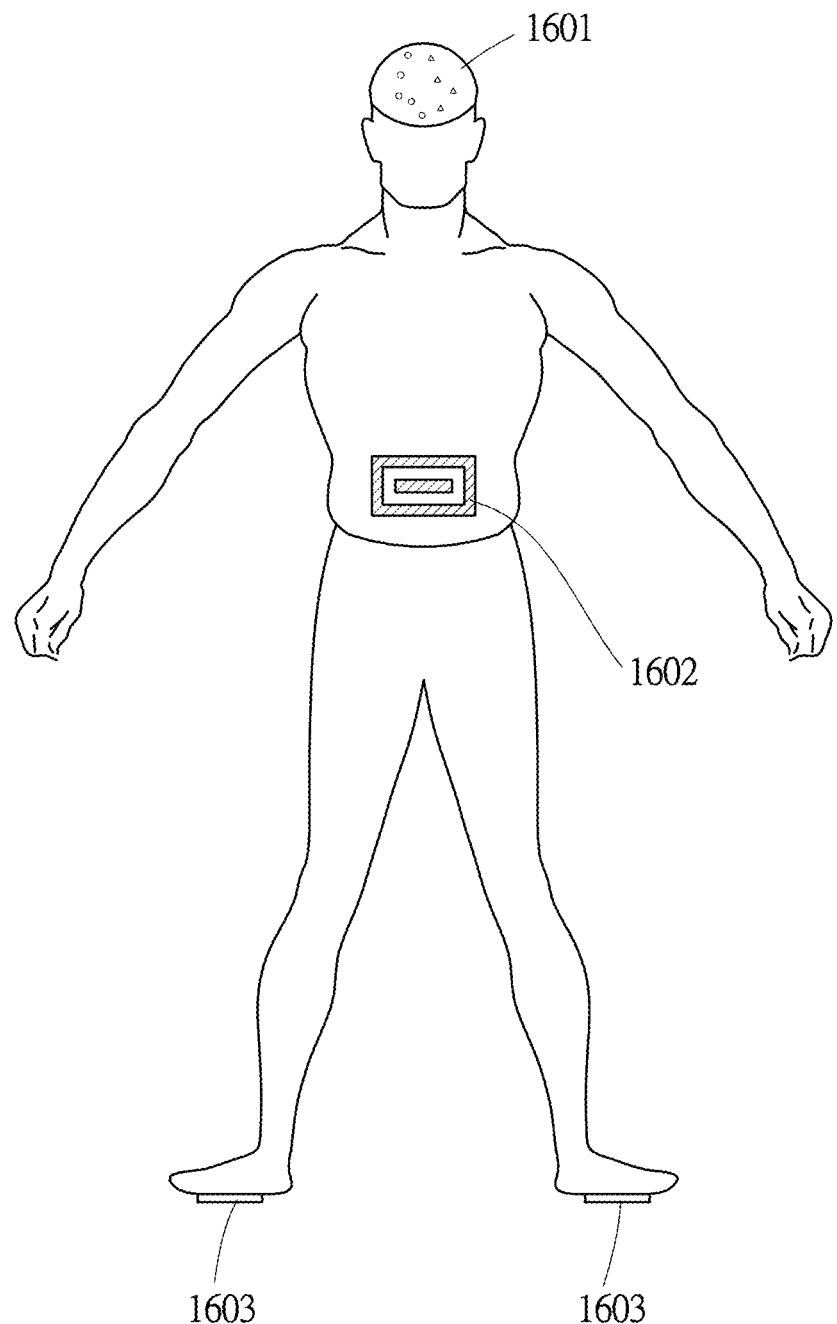
FIG. 17 shows an embodiment of a stimulation prescription using multiple skin carrier sets to effect sleep disorder and/or restoration of foot movement and brain function after stroke.

FIG. 17 shows another embodiment of an inventive physical stimulation treatment modality.

For efficacy consideration, it has been discovered by us that, as part of our inventive process, in many our internal clinical studies, for certain types of pain or chronic or acute ailments such as sudden or prolonged sleep disorder, a stimulation with pulse intensity and frequency of the pulse train rhythmic with music genres favored by that patient may add to efficacy and reduce greatly adaptation and fatigue to the stimulation.

There are commercial products such as a music massage chair that synchronizes the rhythm of massaging rollers with the music rhythm. However, there was not any proposal to apply the rhythm to electrical stimulation waveform. We tested amplitude limited (for safety reason) direct baseband music signal, from 10 Hz to 22 KHz, to body stimulation. We also tested TENS pulse train of varying intensity and pulse frequency synchronized with the music for body stimulation. All these produce pronounced treatment efficacy improvement and fatigue reduction.

It was also discovered in our clinical trial above shown in FIG. 16A, that subjects reported that they felt sleepy more easily than usual during the stimulation treatment and that was also what the clinical assistant observed.

Based on how the peripheral nerves send stimulation signal through the spinal cord Central Nerve System to evoke reactions from nerves and muscle groups, it is also theorized that a skin stimulation carrier placed right around the lumbar spinal cord area with the stimulation waveform dosage similar to that used on the foot soles, it is likely that the stimulation waveform may be reinforced through this intermediate stimulation setup, and reach the brain with higher level of intensity to effect better treatment results, Likewise for the stimulation waveform from the head area to extremities such as foot soles.

Based on the above theorems, two internal clinical studies were conducted in the past to verify them and preliminary results were very encouraging. These past clinical studies were conducted using conventional single-purpose closed ended stimulation controller designs. To articulate how these inventive stimulation treatment modalities may be implemented for future formal clinical trials with greater flexibility, safety and efficacy, we have put together three processes below to explain how the embodiment of these inventive stimulation treatment modalities may be implemented using the proposed PSaaS:

17.1 Embodiment 1 Treating sleep disorder with a scalp skin carrier 1601 using amplitude limiting rhythm waveform or rhythm driven randomized stimulation waveform (RDRSW, see description for FIG. 3F) or Genres Driven Randomized Stimulation Waveform (GDRSW, see descriptions for FIG. 3F)

17.1.1 The Clinician Software on the Host server shall prescribe this treatment modality and specify the skin carrier to use is that shown in FIG. 13D. Pharmacy Software B2 shall synthesize, using our SWC module, either RDRSW or GDRSW stimulation waveform dosage.

17.1.2 Nurse Software shall access the Tool Software to use the skin carrier as shown in FIG. 13D and measure and record the skin resistance of the User with the said skin carrier.

17.1.3 Since this treatment modality is on the User's scalp and the Clinician Software may take the skin impedance information and set an upper limit of the intensity of the stimulation and inform the Nuser Software.

17.1.4 The Nurse Software shall access the Stimulation Point Location Tool and use a proper skin carrier to locate, as taught in descriptions for FIGS. 6B and 6C, a stimulation reference point. Then the User may place the skin carrier properly onto the scalp and the Nurse Software shall start the stimulation.

17.2 Embodiment 2 Treating sleep disorder with a scalp skin carrier 1601 using amplitude limiting rhythm waveform or rhythm driven randomized stimulation waveform (RDRSW, see description for FIG. 3F) or Genres Driven Randomized Stimulation Waveform (GDRSW, see descriptions for FIG. 3F) and a pair of foot sole skin carriers 1603 as shown in FIG. 16B using the stimulation waveform shown in FIG. 16A.

17.2.1 The Clinician Software on the Host server shall prescribe this treatment modality and specify that the skin carrier to use on the scalp is that shown in FIG. 13D and on the foot soles is that shown in FIG. 16B with where to place the pair of electro pads on the foot soles. Pharmacy Software B2 shall synthesize, using our SWC module, either RDRSW or GDRSW stimulation waveform dosage for the scalp skin carrier and prepare the Snippet waveform for the foot sole stimulation waveform in FIG. 16A.

17.2.2 Nurse Software shall access the Tool Software to use the skin carrier as shown in FIG. 13D and FIG. 16B and measure and record the skin resistance of the User on the scalp and on both foot soles with these said skin carrier.

17.2.3 Since this treatment modality is on the User's sensitive scalp and FDA may impose more strict limitations on the allowed intensity of the stimulation. Therefore, the Clinician Software may take the skin resistance information and set an upper limit of the intensity of the stimulation and inform the Nuser Software. For stimulation intensity on both foot soles, the Clinician Software shall also prescribe the guideline on the intensity based on the User's personal information, treatment history and other considerations.

17.2.4 The Nurse Software shall access the Stimulation Point Location Tool and use a proper skin carrier to locate, as taught in descriptions for FIGS. 6B and 6C, a stimulation reference point on the scalp and stimulation points on both foot soles. Then the User may place the skin carrier properly onto the scalp and onto both foot soles, and the Nurse Software shall start the stimulation.

17.3 Embodiment 3 Effecting foot rehabilitation for stroke patient with a scalp skin carrier 1601 using amplitude limiting rhythm waveform or rhythm driven randomized stimulation waveform (RDRSW, see description for FIG. 3F) or Genres Driven Randomized Stimulation Waveform (GDRSW, see descriptions for FIG. 3F), with a skin carrier 1602 on the lower lumbar spinal cord area, such as as an example shown in FIG. 1.03 using the waveform shown in FIG. 16A, and a pair of skin carriers 1603 such as shown in FIG. 16B on both foot soles using the waveform shown in FIG. 16A. This is merely an example and an embodiment and the combination of the skin carriers and the stimulation waveform that may be used are not limited to the examples and embodiments used here in and its inventive methods and systems are not limited by the limited embodiment in this example.

17.3.1 The Clinician Software on the Host server shall prescribe this treatment modality and specify that the skin carrier to use on the scalp is that shown in FIG. 13D, on the lower lumbar is a standard two polarity electro gel pads (called Standard Pad herein) and on both foot soles is that shown in FIG. 16B, with where to place the pair of electro pads on the lower lumbar and on the foot soles. Pharmacy Software B2 shall synthesize, using our SWC module, either RDRSW or GDRSW stimulation waveform dosage for the scalp skin carrier and prepare the Snippet waveform for the lower lumbar and foot sole stimulation waveform per FIG. 16B.

Nurse Software shall access the Tool Software to use the skin carrier as shown in FIG. 13D, FIG. 10A and FIG. 16B and measure and record the skin resistance of the User on the scalp, lower lumbar and on both foot soles with these said skin carriers.

Since this treatment modality is on the User's sensitive scalp and FDA may impose more strict limitations on the allowed intensity of the stimulation. Therefore, the Clinician Software may take the skin resistance information and set a upper limit of the intensity of the stimulation and inform the Nurse Software. For stimulation intensity on the lower lumbar and on both foot soles, the Clinician Software shall also prescribe the guideline on the intensity based on the User's personal information, treatment history and other considerations.

The Nurse Software shall access the Stimulation Point Location Tool and use a proper skin carrier to locate, as taught in descriptions for FIGS. 6B and 6C, a stimulation reference point on the scalp and stimulation points on the lower lumbar and on both foot soles. Then the User may place the skin carrier properly onto the scalp and onto the lower lumbar and onto both foot soles, and the Nurse Software shall start the stimulation.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A system for effecting physical stimulation as a Service comprising:
  a server side service subsystem including a server,
  a client service subsystem including a client device that can be a mobile phone or a pad,
  at least one stimulation controller, and
  at least one skin carrier;
  wherein the client service subsystem further includes:
  an AR software engine executed by the client device; and
  a skin carrier placement tool software executed by the client device, which helps place the at least one skin carrier on a stimulation point X on a body prescribed by a prescription and which includes:
  making a visual and/or texture display of the stimulation point X on a standard body model, and representing said display of the stimulation point X by Z;
  aiming a camera right on the body shown by Z to generate an image, overlaying the stimulation point X on the image by the AR software engine, and marking on a body position Y where the overlaid X from AR is.

2. The system for effecting physical stimulation as a Service as claimed in claim 1, further comprising:
  a physical stimulation level monitoring that monitors stimulation states of the physical stimulation with a sensor built in the skin carriers and the states include current level in electrical stimulation, magnetic field strength in magnetic stimulation, pressure level in the pressure and compression, or temperature level in temperature stimulation.

3. The system for effecting physical stimulation as a Service as claimed in claim 1, wherein the skin carrier is a skin carrier having heat stimulation, electrical stimulation and magnetic stimulation, wherein
  a pair of electro-pads that provides the electrical stimulation;
  a skin carrier powered heat or magnetic or multiple pressure, or non-powered heat or cold stimulation, magnetic or mechanical pressure, which is located between the pair of pads to increase stimulation at or near points of pain or discomfort to improve treatment; and,
  a plurality of fixing pads that affixes the skin carrier securely to the body.

4. The system for effecting physical stimulation as a Service as claimed in claim 3, wherein the skin carrier further comprises:
  an identification tag that may be a NFC tag, a printed serial number, a printed bar code tag, or a QR code to provide the type of skin carrier to the user or the client service subsystem.

5. The system for effecting physical stimulation as a Service as claimed in claim 1, wherein
  measuring the lowest skin impedance around the body position Y to get a body position Y1 is performed by a measuring minimum skin impedance tool, having at least one resistance measuring circuit and a plurality of dual polarity skin carriers, which is for measuring all skin impedance values of the plurality of dual polarity skin carriers, wherein a position of a dual polarity skin carrier with the lowest skin impedance is the body position Y1.

6. A system for effecting physical stimulation as a Service comprising:
  a server side service subsystem including a server,
  a client service subsystem including a client device that can be a mobile phone or a pad;
  at least one stimulation controller, and
  at least one skin carrier;
  wherein the client service subsystem further comprises:
  an AR software engine executed by the client device; and a skin carrier placement tool software executed by the client device, which helps a user register custom pain points in a database of stimulation points on a standard body model, and which includes:

marking a pain point on a body part with a unique symbol called AA;

aiming a camera right on the body part containing AA to get an image; and recognizing the marked AA and the body part where the AA is, by performing AR imaging, pattern and object recognition and scaling processing on the image by the AR software engine, and registering AA and the body part where the AA is in the database of stimulation points on the standard body model.

7. A system for effecting physical stimulation as a Service as claimed in claim 6, wherein the skin carrier placement tool software further includes:

guiding the user to determine whether the pain point AA is a point of treatment;

if the pain point AA is a point of treatment, a clinician software executed by the server, along with the database of the stimulation points on the standard body model, prescribes a group of stimulation points to treat the pain point AA.

8. A system for effecting physical stimulation as a Service as claimed in claim 6, wherein the skin carrier placement tool software further includes:

guiding the user to determine whether the pain point AA is a point of treatment;

if the pain point AA is not a point of treatment, a clinician software executed by the server, along with the database of the stimulation points on the standard body model, displays possible points of treatment related to the pain point AA;

guiding the user to select points of treatment from the possible points of treatment;

the clinician software prescribing a group of stimulation points X's to treat the pain point AA, based on the selected points of treatment.

9. A system for effecting physical stimulation as a Service as claimed in claim 6, wherein the scaling processing on the image by the AR software engine is further assisted by placing a reference sticker or a marker on the target body part for scaling or adjusting the image of the body part containing AA to match the standard body model.

10. A system for effecting physical stimulation as a Service comprising:

a server side service subsystem including a server;

a client service subsystem including a client device that can be a mobile phone or a pad;

at least one stimulation controller; and at least one skin carrier;

wherein the client service subsystem further comprises:

a skin carrier placement tool software executed by the client device, which assists placing the at least one skin carrier on the body by a stimulation point X prescribed by a prescription and which includes:

making a visual and/or texture display of the stimulation point X on a standard body model;

guiding a user to mark a particular symbol at a body position Y considered to be the stimulation point X;

taking a picture of the body part including the body position Y with a camera;

placing a reference sticker or a marker on the body position Y for scaling or adjusting the picture of the body part to match the standard body model in order to register the stimulation point X on the picture of the body part;

comparing whether the body position Y is close enough to the stimulation point X, if not close enough, restarting from the above-mentioned marking the body position Y and repeating the process until the body position Y is close enough to the stimulation point X.

11. A system for effecting physical stimulation as a Service as claimed in claim 10, wherein the skin carrier placement tool software utilizes a size, an angle and an orientation of the reference sticker or the marker on the body position Y to determine a camera angle and a distance between the camera and the body position Y, to assist scaling or adjusting the picture of the body part to match the standard body model.

\* \* \* \* \*